(12) United States Patent
Connely, IV et al.

(10) Patent No.: US 11,942,197 B2
(45) Date of Patent: *Mar. 26, 2024

(54) SYSTEMS AND METHODS FOR SURFACING CONTEXTUALLY RELEVANT CONTENT INTO THE WORKFLOW OF A THIRD PARTY SYSTEM VIA A DISTRIBUTED ARCHITECTURE

(71) Applicant: SNAPS Solutions LLC, Alpharetta, GA (US)

(72) Inventors: Robert Emmitt Connely, IV, Roswell, GA (US); Bryant Paul Castleton, Alpharetta, GA (US); James Tropauer, Marietta, GA (US); Saurabh Mathur, Cumming, GA (US)

(73) Assignee: SNAPS Solutions, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/677,081

(22) Filed: Feb. 22, 2022

(65) Prior Publication Data

US 2022/0180985 A1 Jun. 9, 2022

Related U.S. Application Data

(63) Continuation of application No. 17/194,426, filed on Mar. 8, 2021, now Pat. No. 11,568,971, which is a (Continued)

(51) Int. Cl.
*G16H 10/60* (2018.01)
*G06F 16/26* (2019.01)
(Continued)

(52) U.S. Cl.
CPC ............. *G16H 10/60* (2018.01); *G06F 16/26* (2019.01); *G06F 16/27* (2019.01);
(Continued)

(58) Field of Classification Search
CPC ........ G16H 40/67; G16H 10/60; G16H 40/20; G16H 30/20; G16H 20/00; G16H 20/10;
(Continued)

(56) References Cited

U.S. PATENT DOCUMENTS 5,664,109 A 9/1997 Johnson et al.
5,974,389 A 10/1999 Clark et al.
(Continued)

FOREIGN PATENT DOCUMENTS

WO 2016100073 A1 6/2016
WO 2016137682 A1 9/2016

OTHER PUBLICATIONS

Kart, Firat, et al., A Distributed e-Healthcare System Based on the Service Oriented Architecture, IEEE International Conference on Services Computing, 2007.
(Continued)

*Primary Examiner* — Peter H Choi
*Assistant Examiner* — William T. Monticello
(74) *Attorney, Agent, or Firm* — Morris, Manning & Martin, LLP; Daniel E. Sineway, Esq.; Daniel T. Begasse, Esq.

(57) ABSTRACT

Systems and methods for surfacing contextually relevant data into the workflow of a third party system are discussed herein. The system implements a near-real-time method of detecting activity corresponding to particular electronic health records associated with particular patients in third-party systems using specifically configured software systems. A cloud-based micro-services architecture is communicably coupled to the third-party systems and is operable to transmit contextually relevant data to the third-party system in response to particular detected activities, such as accessing a patient's electronic health record. The contextually-relevant data is identified by comparing electronic health
(Continued)

EXEMPLARY MEDICARE ADVANTAGE RISK REDUCTION OVERVIEW record data from various third-party systems, each third-party system associated with the particular patient, to determine gaps in the records. The contextually relevant data is transmitted to the third-party system and visually integrated into the third-party system's pre-existing clinical workflow.

18 Claims, 29 Drawing Sheets

Related U.S. Application Data continuation of application No. 15/796,391, filed on Oct. 27, 2017, now Pat. No. 10,984,897.

(60) Provisional application No. 62/413,615, filed on Oct. 27, 2016.

(51) Int. Cl.

| | | |
|---|---|---|
| *G06F 16/27* | (2019.01) | |
| *G06Q 10/0633* | (2023.01) | |
| *G06Q 40/08* | (2012.01) | |
| *G16B 20/10* | (2019.01) | |
| *G16H 20/00* | (2018.01) | |
| *G16H 20/10* | (2018.01) | |
| *G16H 30/20* | (2018.01) | |
| *G16H 40/20* | (2018.01) | |
| *G16H 40/63* | (2018.01) | |
| *G16H 40/67* | (2018.01) | |
| *G16H 50/30* | (2018.01) | |
| *H04L 9/40* | (2022.01) | |
| *H04L 67/10* | (2022.01) | |
| *H04L 67/12* | (2022.01) | |
| *H04L 67/53* | (2022.01) | |
| *H04W 12/02* | (2009.01) | |

(52) U.S. Cl.
CPC ......... *G06Q 10/0633* (2013.01); *G06Q 40/08* (2013.01); *G16B 20/10* (2019.02); *G16H 20/00* (2018.01); *G16H 20/10* (2018.01); *G16H 30/20* (2018.01); *G16H 40/20* (2018.01); *G16H 40/63* (2018.01); *G16H 40/67* (2018.01); *H04L 67/10* (2013.01); *H04W 12/02* (2013.01); *G16H 50/30* (2018.01); *H04L 63/02* (2013.01); *H04L 63/0227* (2013.01); *H04L 63/08* (2013.01); *H04L 67/12* (2013.01); *H04L 67/53* (2022.05)

(58) Field of Classification Search
CPC ........ G16H 40/63; G16H 50/30; G06F 16/27; G06F 16/26; G16B 20/10; G06Q 10/0633; G06Q 40/08; H04L 67/10; H04L 67/53; H04L 63/02; H04L 63/0227; H04L 63/08; H04L 67/12; H04W 12/02
See application file for complete search history.

(56) References Cited

U.S. PATENT DOCUMENTS

| | | |
|---|---|---|
| 6,523,009 B1 | 2/2003 | Wilkins et al. |
| 7,233,938 B2 | 6/2007 | Carus et al. |
| 8,250,045 B2 | 8/2012 | Er et al. |
| 8,311,854 B1 | 11/2012 | Stanley et al. |
| 8,533,004 B1 | 9/2013 | Grady et al. |
| 8,578,076 B2 | 11/2013 | Van Der Linden et al. |
| 8,650,045 B2 | 2/2014 | Baldock et al. |
| 8,689,008 B2 | 4/2014 | Rangadass et al. |
| 8,966,074 B1 | 2/2015 | Richards et al. |
| 9,183,064 B2 | 11/2015 | Ahmed et al. |
| 9,208,284 B1 | 12/2015 | Douglass |
| 9,262,127 B2 | 2/2016 | Patrick |
| 9,354,998 B2 | 5/2016 | Hyland et al. |
| 9,501,624 B2 | 11/2016 | Vishnubhatla et al. |
| 9,703,927 B2 | 7/2017 | Chaudhri et al. |
| 9,710,600 B1 | 7/2017 | Dunleavy et al. |
| 9,766,955 B2 | 9/2017 | Ahmed et al. |
| 10,468,126 B1 | 11/2019 | Harding et al. |
| 2005/0262193 A1 | 11/2005 | Mamou et al. |
| 2008/0040151 A1 | 2/2008 | Moore et al. |
| 2009/0024416 A1* | 1/2009 | McLaughlin et al. |
| 2009/0048869 A1 | 2/2009 | Tyler |
| 2009/0216558 A1 | 8/2009 | Reisman et al. |
| 2010/0106547 A1 | 4/2010 | Adi et al. |
| 2011/0110568 A1 | 5/2011 | Vesper et al. |
| 2011/0288877 A1 | 11/2011 | Ofek et al. |
| 2012/0215560 A1* | 8/2012 | Ofek et al. |
| 2012/0240195 A1 | 9/2012 | Weiss |
| 2013/0110547 A1 | 5/2013 | Englund et al. |
| 2013/0191157 A1 | 7/2013 | Eiden et al. |
| 2013/0290020 A1* | 10/2013 | Brush |
| 2013/0311653 A1 | 11/2013 | Hernandez et al. |
| 2014/0032242 A1 | 1/2014 | Laborde et al. |
| 2014/0032259 A1 | 1/2014 | Lafever et al. |
| 2014/0058750 A1 | 2/2014 | Fotsch et al. |
| 2014/0088985 A1 | 3/2014 | Grant et al. |
| 2014/0095180 A1 | 4/2014 | Venkat et al. |
| 2014/0222444 A1 | 8/2014 | Cerello et al. |
| 2014/0278511 A1 | 9/2014 | Fielding et al. |
| 2014/0358584 A1 | 12/2014 | Worden et al. |
| 2014/0365232 A1 | 12/2014 | Sadeghi |
| 2015/0081332 A1 | 3/2015 | Casper et al. |
| 2015/0161328 A1 | 6/2015 | Callahan et al. |
| 2015/0213195 A1 | 6/2015 | Blechman et al. |
| 2015/0379214 A1* | 6/2015 | Valentine et al. |
| 2015/0193583 A1* | 7/2015 | McNair et al. |
| 2015/0331995 A1 | 11/2015 | Zhao et al. |
| 2015/0356246 A1 | 12/2015 | D'Souza et al. |
| 2015/0363563 A1 | 12/2015 | Hallwachs |
| 2016/0098533 A1 | 4/2016 | Jackson et al. |
| 2016/0110523 A1 | 4/2016 | Francois |
| 2016/0132645 A1 | 5/2016 | Charpentier et al. |
| 2016/0147946 A1 | 5/2016 | Von Reden |
| 2016/0283662 A1 | 9/2016 | Batta |
| 2016/0357912 A1 | 12/2016 | Morris et al. |
| 2017/0011196 A1 | 1/2017 | Arshad et al. |
| 2017/0076046 A1* | 3/2017 | Barnes |
| 2017/0109472 A1* | 4/2017 | Dominick et al. |
| 2017/0212989 A1 | 7/2017 | Laborde, Jr. et al. |
| 2017/0344716 A1 | 11/2017 | Abou-Sayed et al. |
| 2018/0018428 A1* | 1/2018 | Coifman |
| 2018/0300124 A1 | 10/2018 | Malladi et al. |
| 2020/0098472 A1 | 3/2020 | Hickle et al. |

OTHER PUBLICATIONS

Orbeta, Philip, A Service-Oriented Approach to Electronic Medial Records in Developing Countries, Carnegie Mellon University, 2008.

Juneja, et al., Improving Performance of Healthcare Systems with Service Oriented Architecture, InfoQ, Mar. 7, 2008, https://www.infoq.com/articles/soa-healthcare.

Baum, et al., Oracle SOA Suite for Healthcare Integration, Oracle White Paper, Oct. 2013.

Webster, Chuck, From APIs to Microservices: Workflow Orchestration and Choreography Across Healthcare Organizations, the Healthcare Business Process Management Blog, Nov. 11, 2016.

Wullianallur, et al., Interoperable Electronic Health Records Design: Towards a Service-Oriented Architecture, E- Service Journal 5.3, 2007.

Awad, et al., Patient-Centric Secure-and-Privacy-Preserving Service-Oriented Architecture for Health Information Integration and Exchange, George Mason University, Center for Health Information Technology, 2011.

Wells, Brian J., et al., Strategies for Handling Missing Data in Electronic Health Record Derived Data, eGEMs (Generating Evidence & Methods to improve patient outcomes): vol. 1: Iss. 3, Article 7, 2013.

(56) References Cited

OTHER PUBLICATIONS

MicroStrategy, Business Intelligence Solutions for Healthcare Providers, Dec. 14, 2016, https://www.microstrategy.com/Strategy/media/downloads/solutions/MicroStrategy-Mobile-Healthcare-Providers-Brochure.pdf.
International Search Report and Written Opinion dated Jan. 26, 2018 in International Appl. No. PCT/US17/58818.
Extended European Search Report dated Jul. 21, 2020 for European Patent Application No. 17864753.3.

* cited by examiner

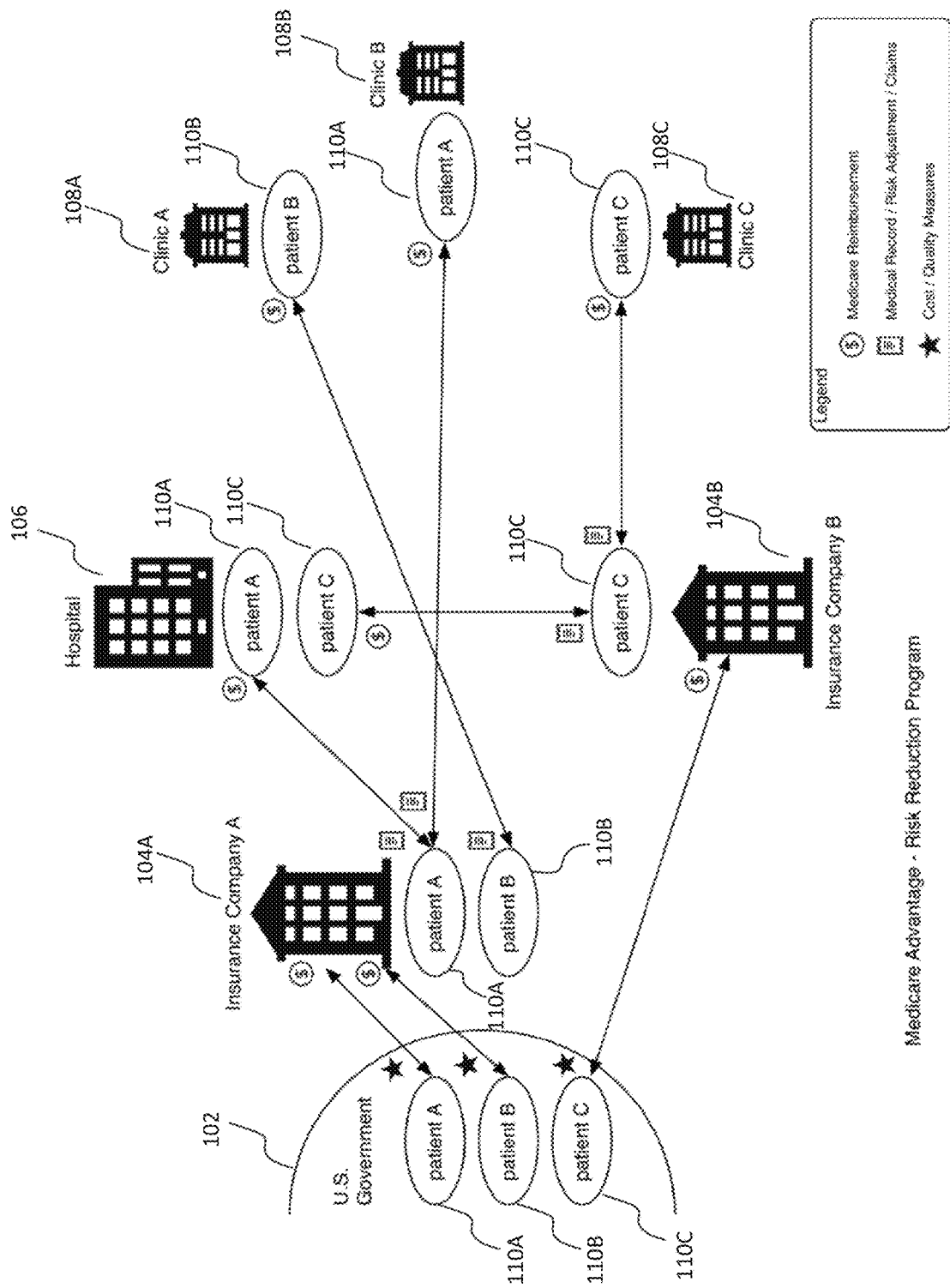
FIG. 1: EXEMPLARY MEDICARE ADVANTAGE RISK REDUCTION OVERVIEW

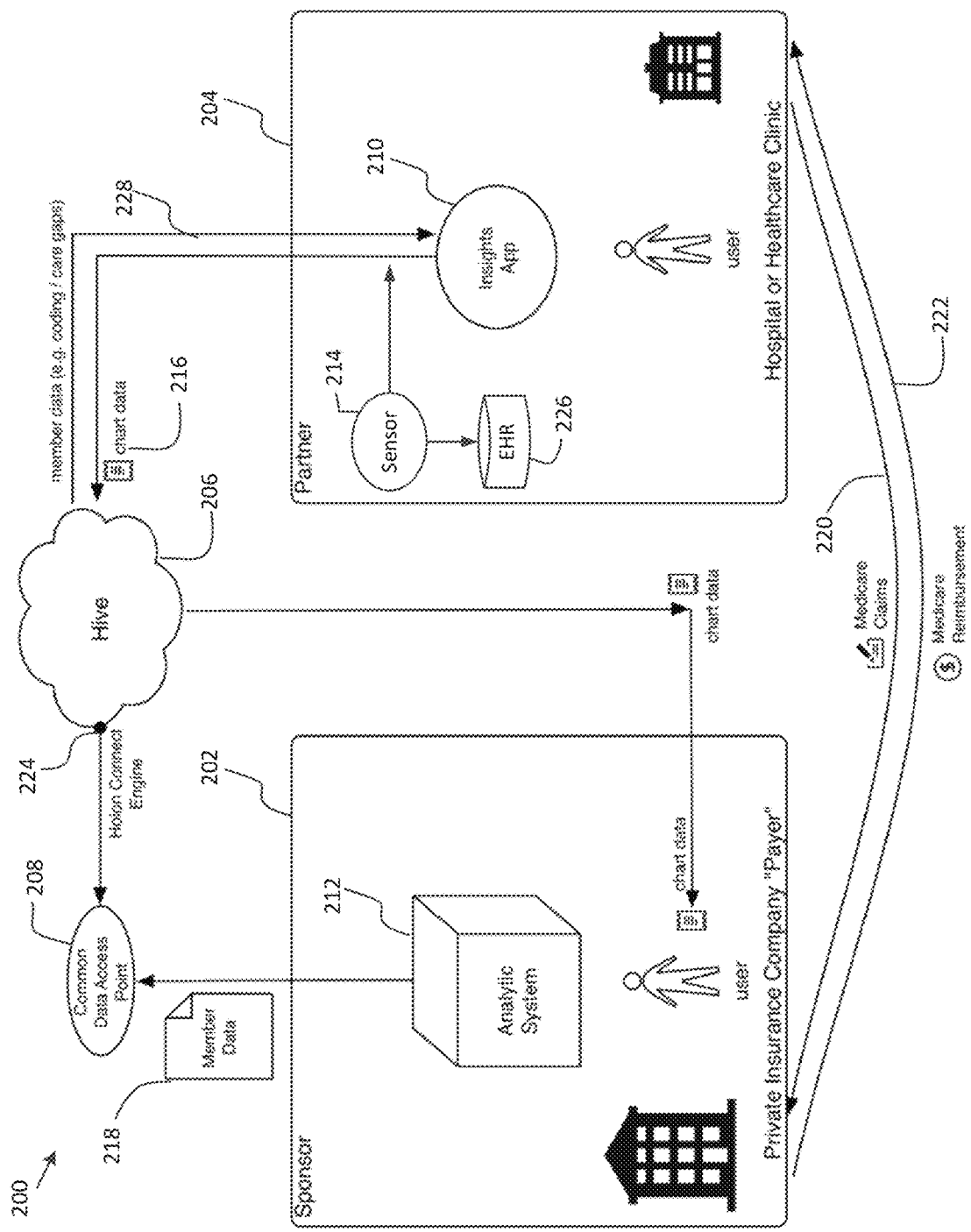
FIG. 2: EXEMPLARY SYSTEM OPERATIONAL ENVIRONMENT

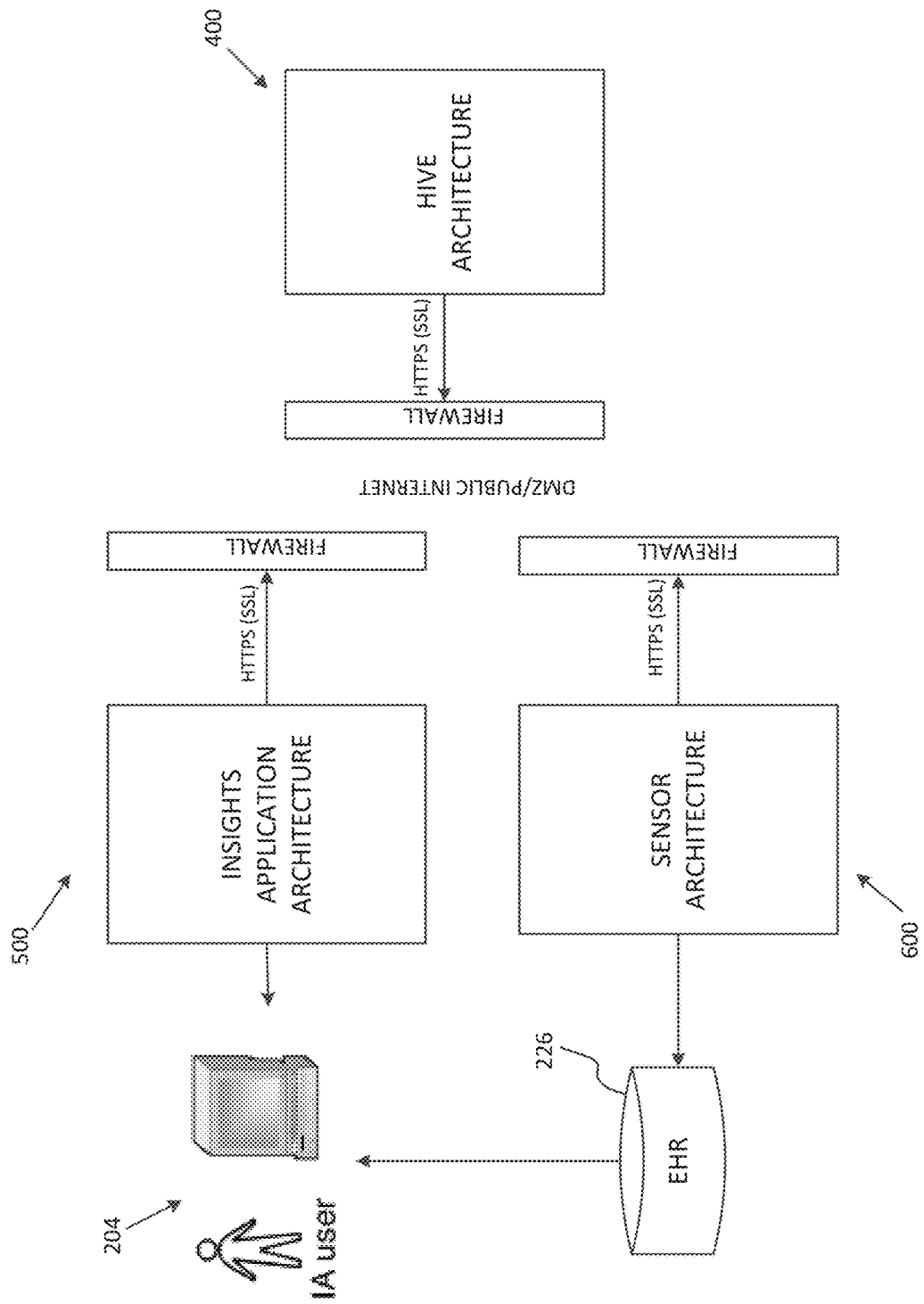
FIG. 3: EXEMPLARY SYSTEM ARCHITECTURAL COMPONENTS

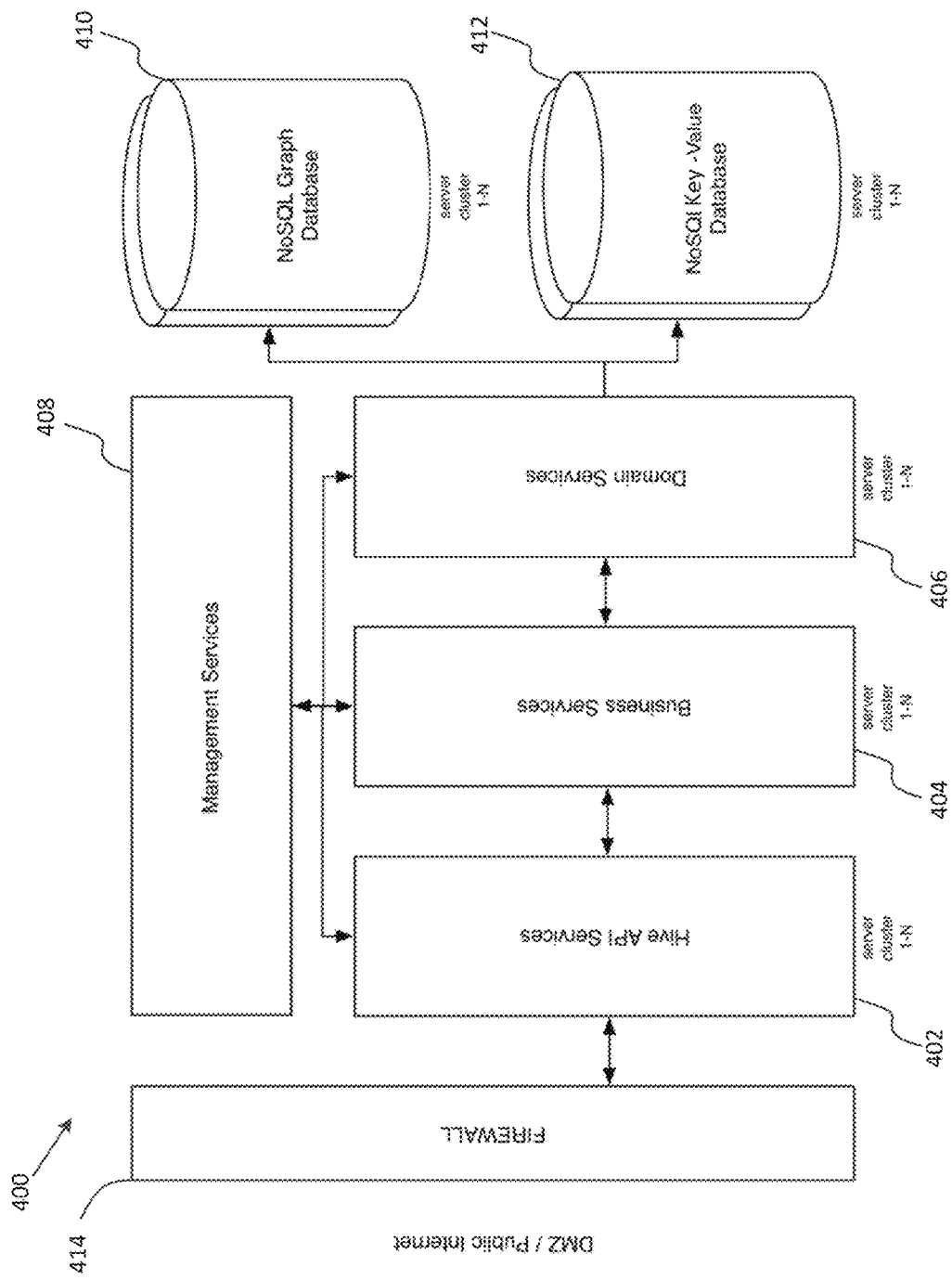
FIG. 4: EXEMPLARY HIVE ARCHITECTURAL COMPONENTS

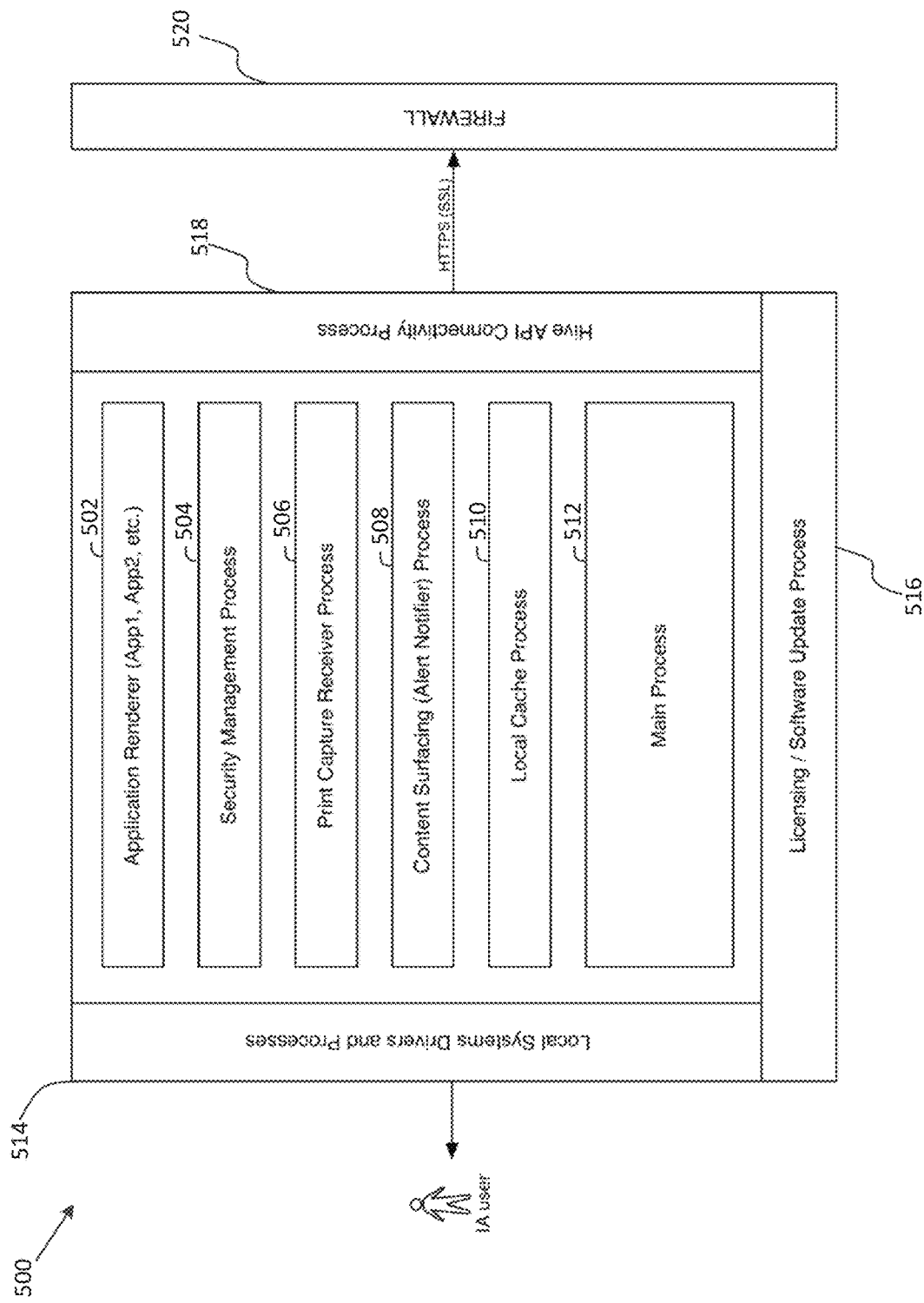
FIG. 5: EXEMPLARY INSIGHTS APPLICATION ARCHITECTURAL COMPONENTS

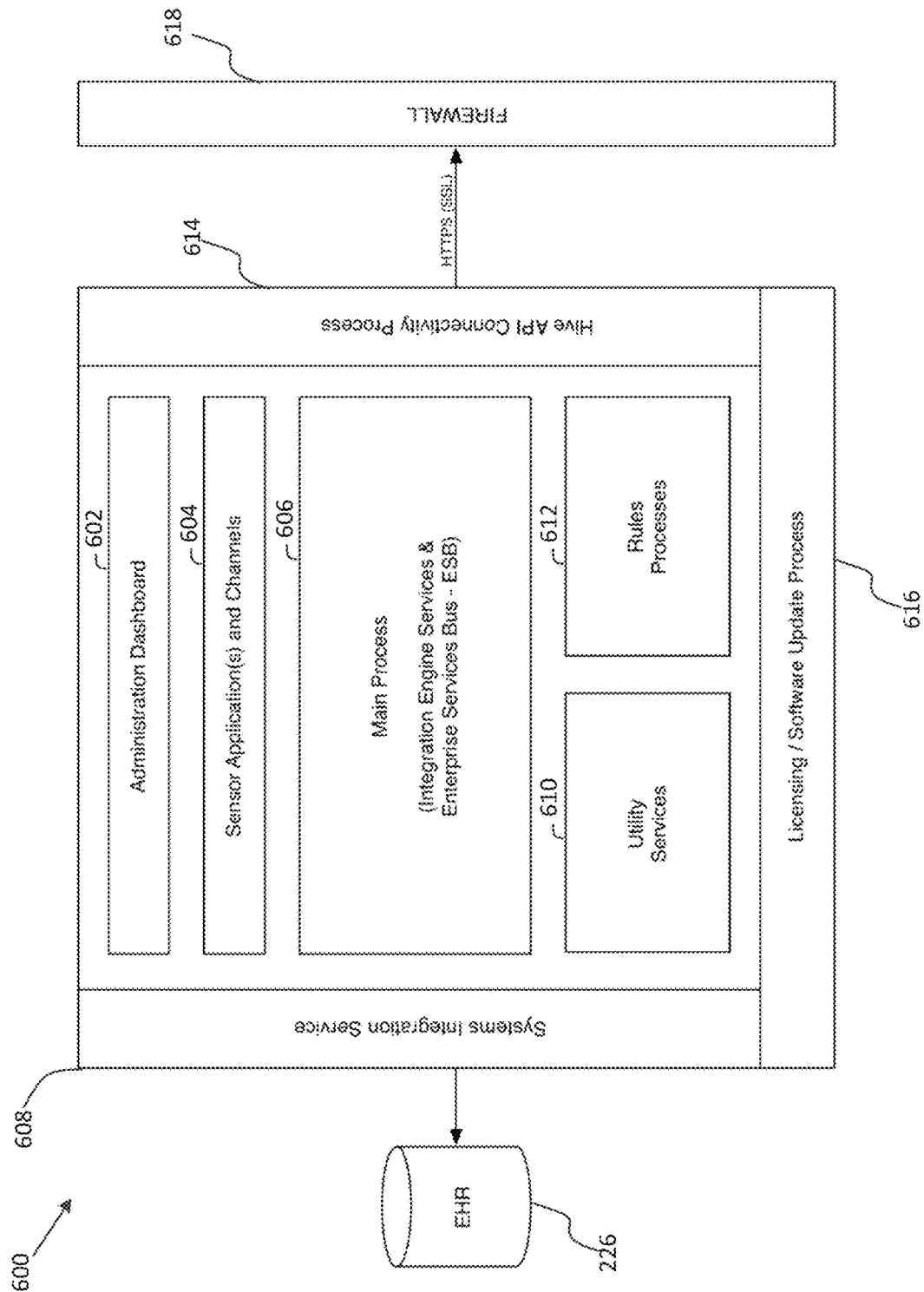
FIG. 6: EXEMPLARY SENSOR ARCHITECTURAL COMPONENTS

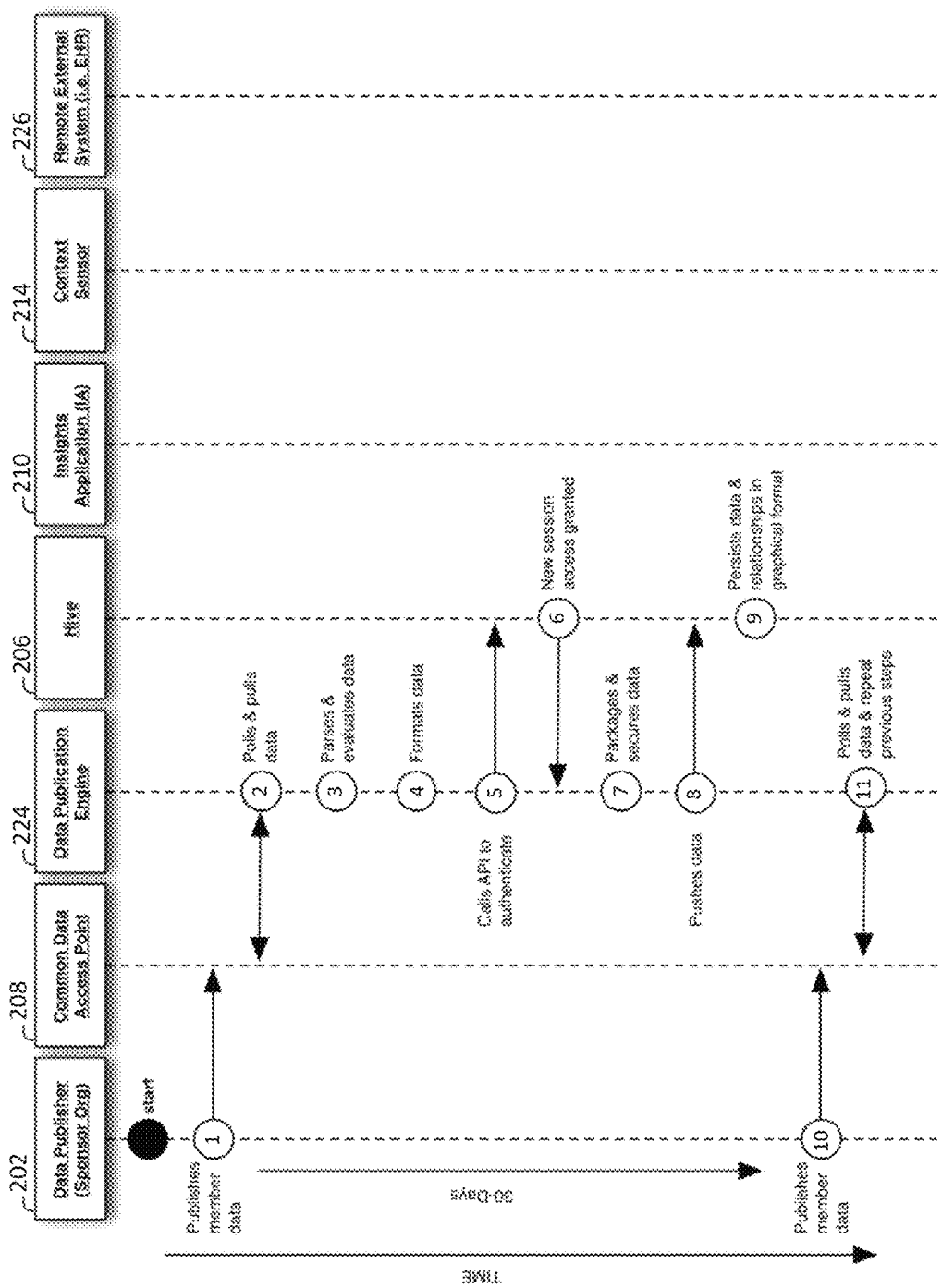
FIG. 7: EXEMPLARY DATA PROVISIONING SEQUENCE DIAGRAM

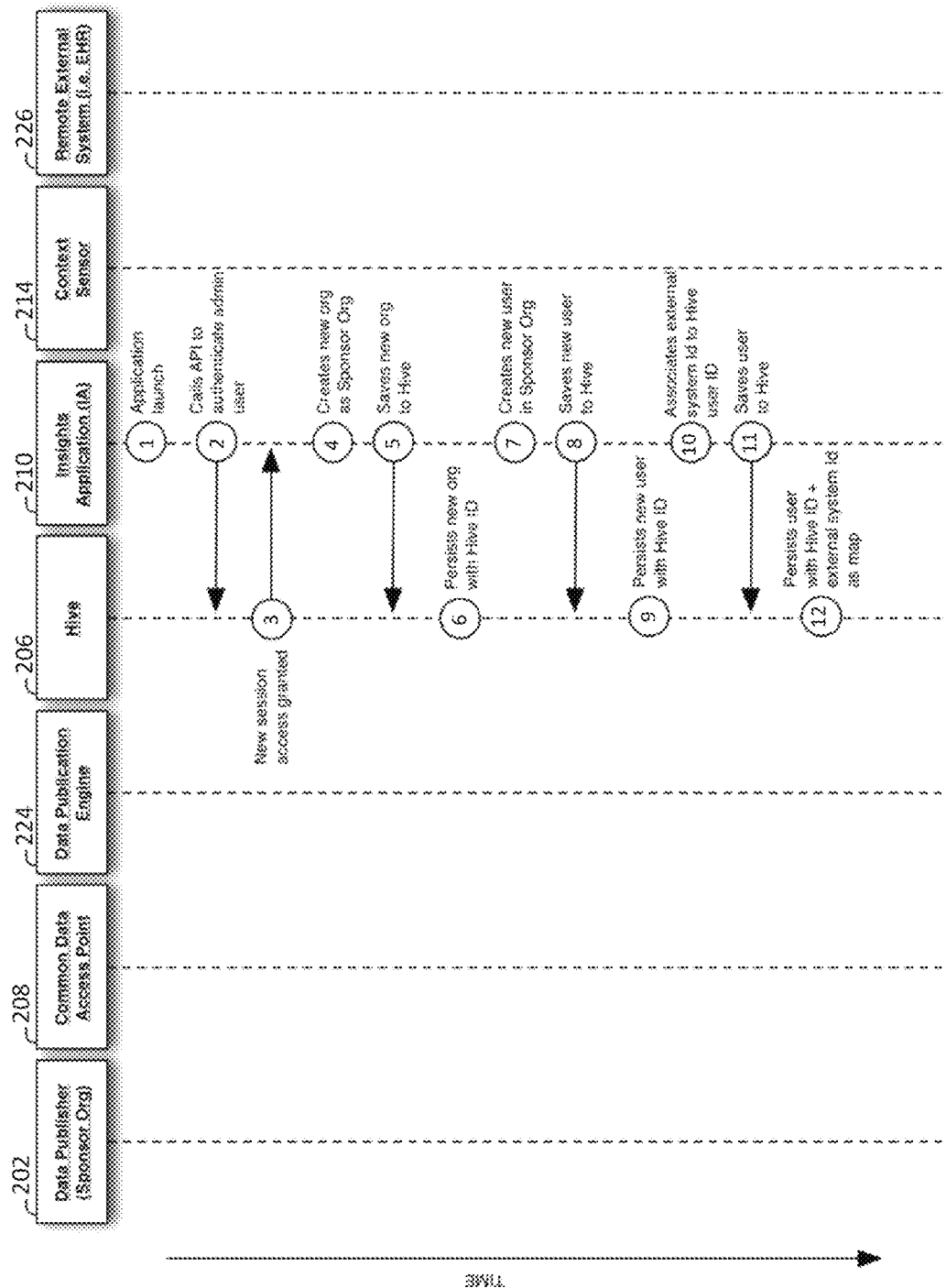
FIG. 8: EXEMPLARY ORGANIZATION AND USER PROVISIONING SEQUENCE DIAGRAM

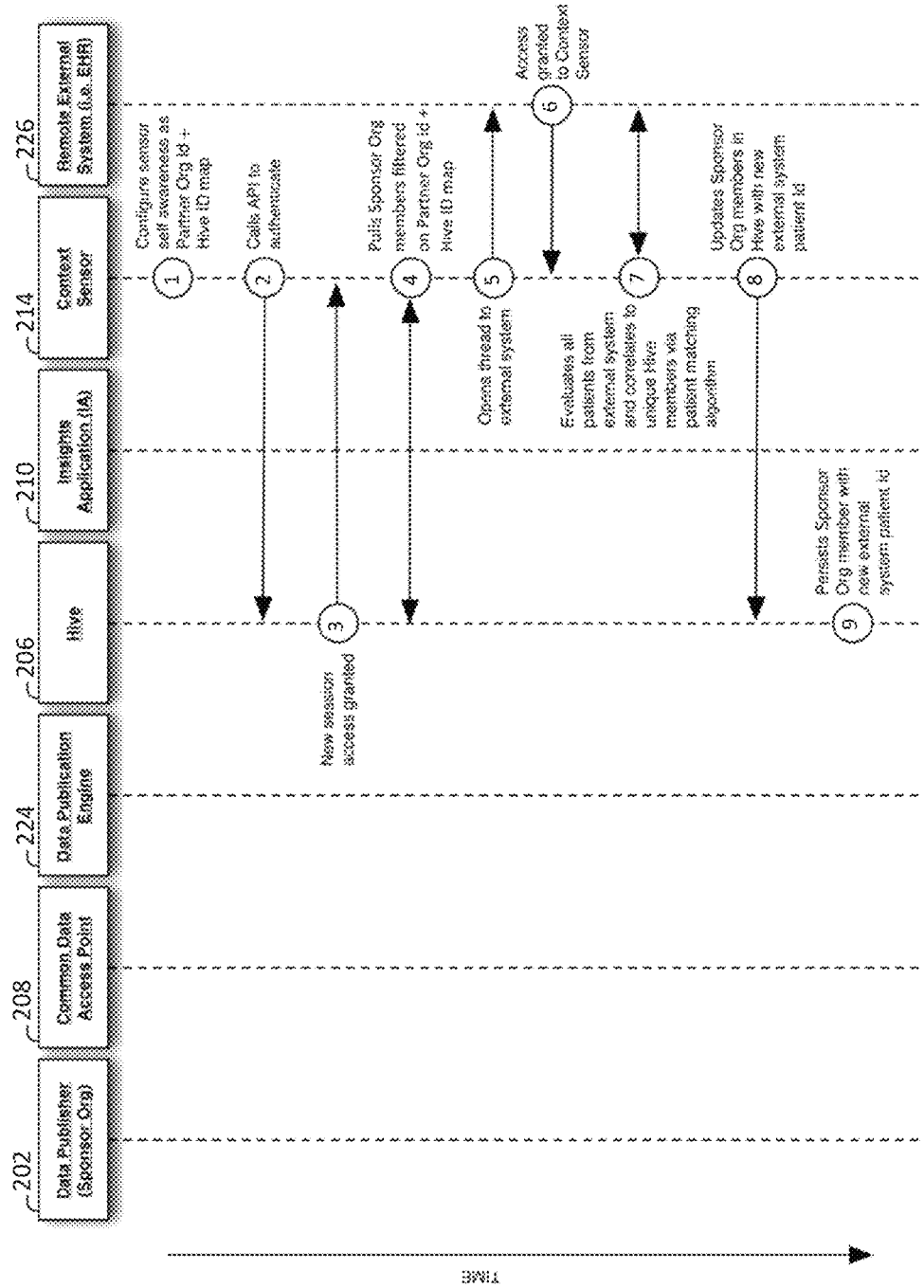
FIG. 9: EXEMPLARY MEMBERSHIP ATTESTATION AND EXEMPLARY IDENTITY MATCHING SEQUENCE DIAGRAM

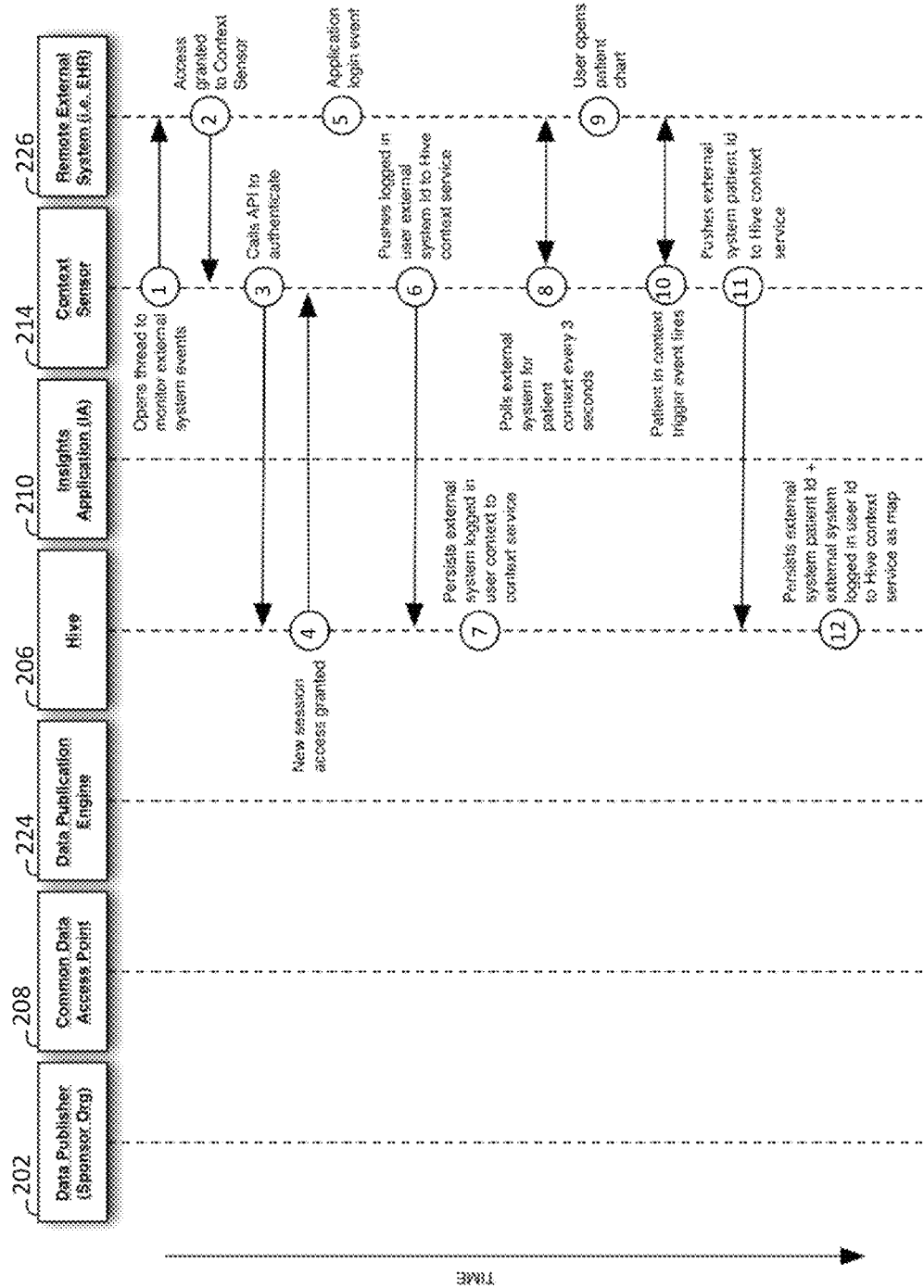
FIG. 10: EXEMPLARY REMOTE SYSTEM CONTEXT CONTROL SEQUENCE DIAGRAM

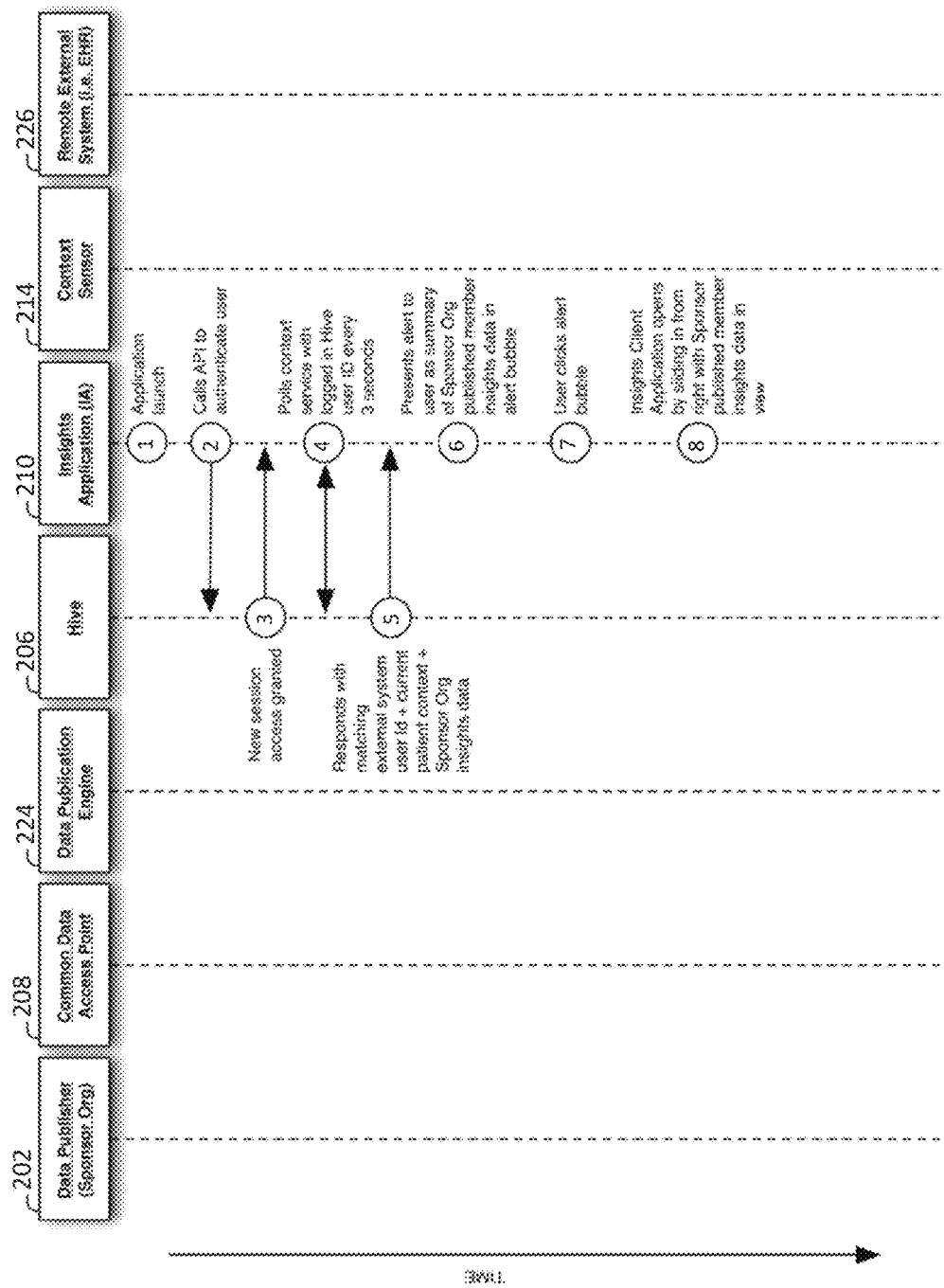
FIG. 11: EXEMPLARY CONTEXT SENSITIVE ALERT AND DATA PRESENTATION SEQUENCE DIAGRAM

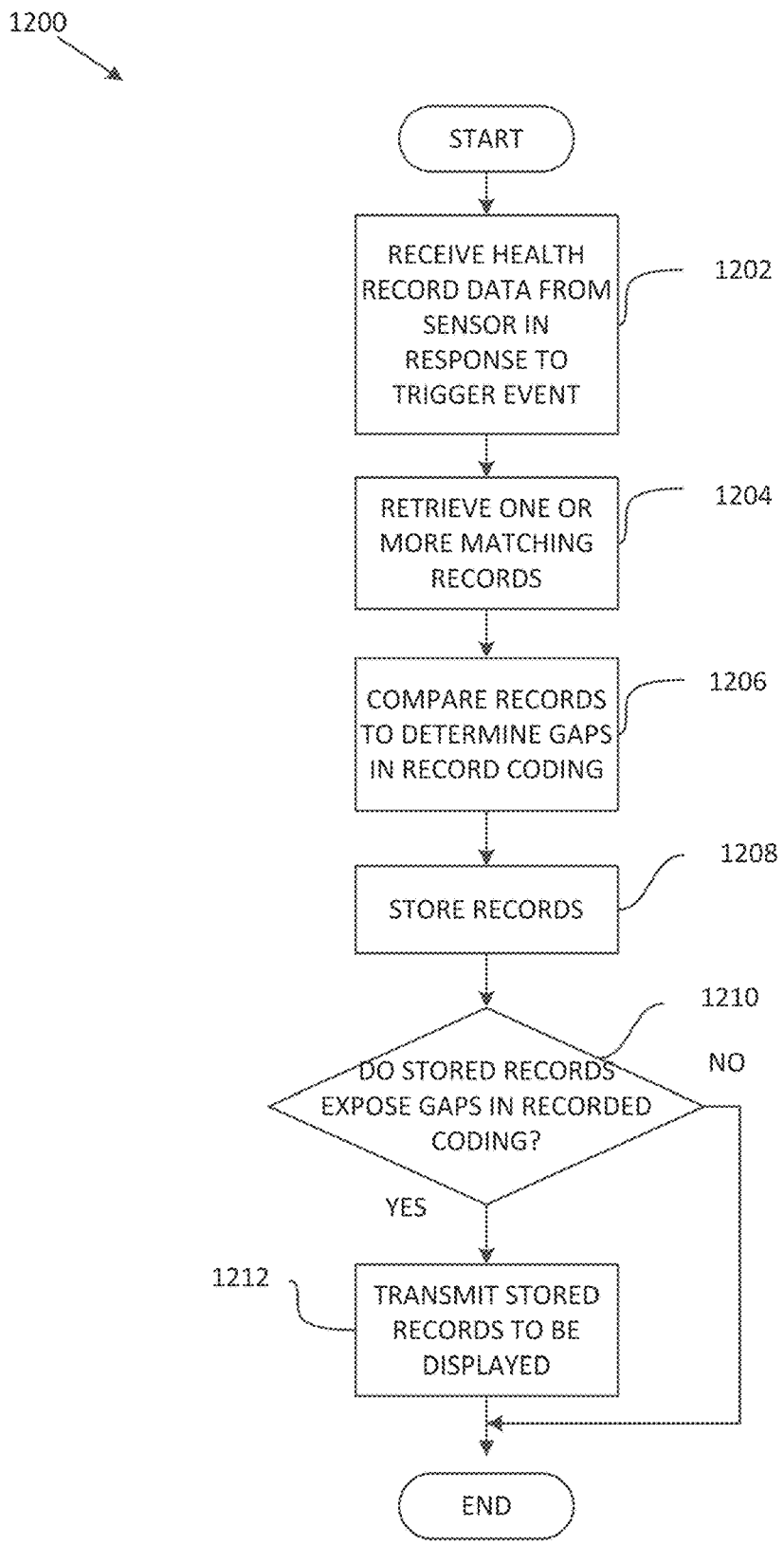
FIG. 12: EXEMPLARY SYSTEM CODE GAP PROCESS

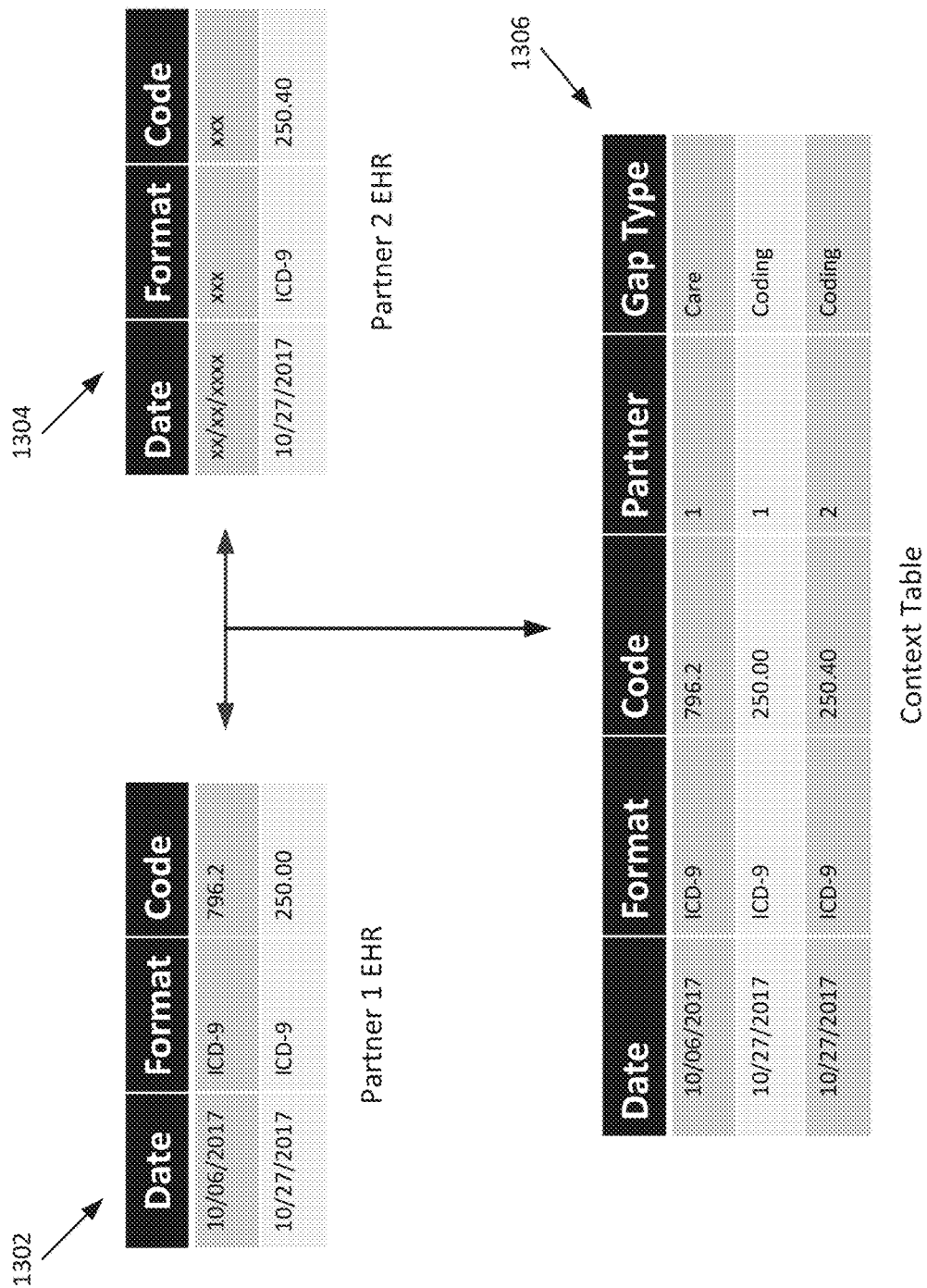
FIG. 13: EXEMPLARY GAP CONTEXT DATA STRUCTURE

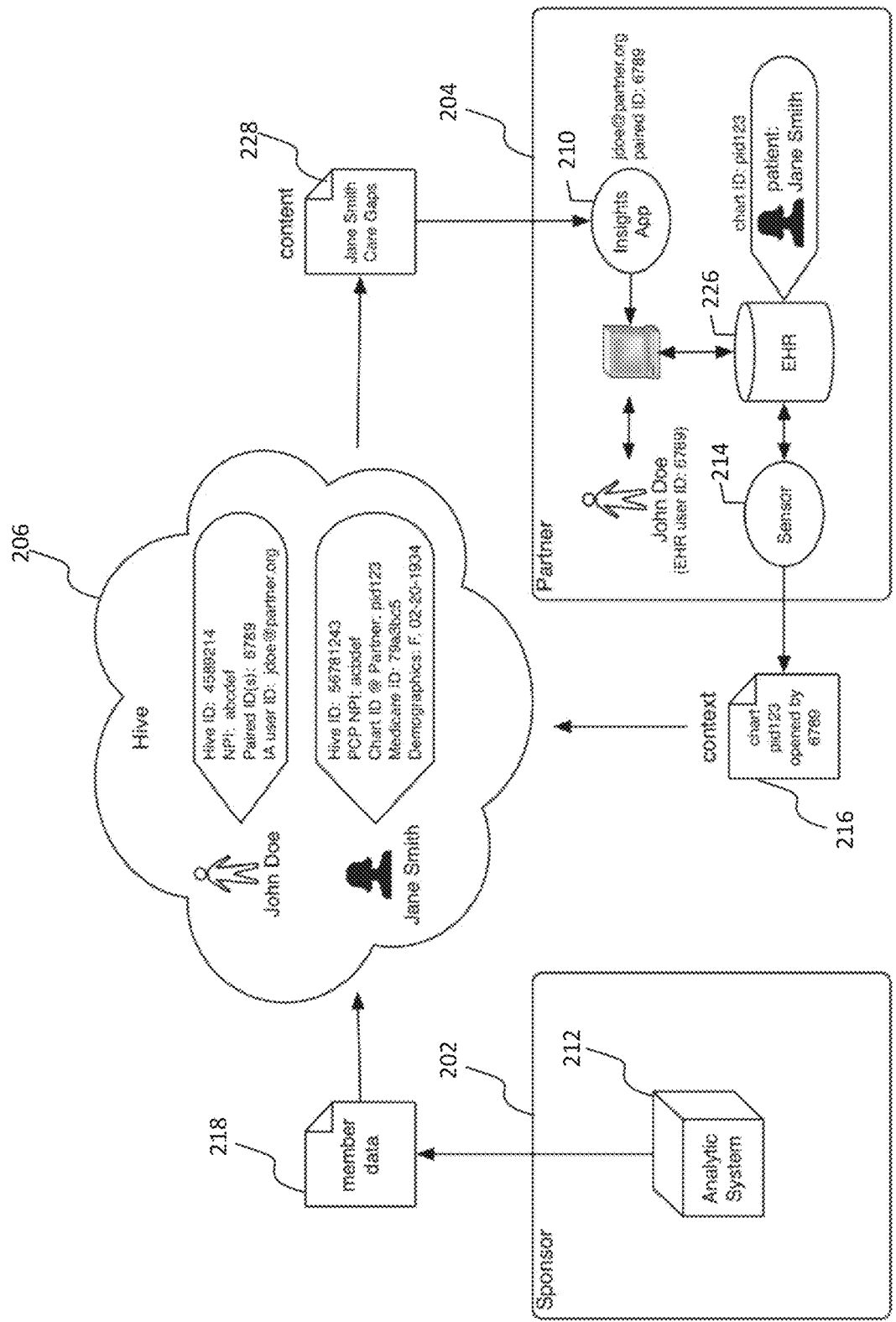
FIG. 14: EXEMPLARY IDENTITY MANAGEMENT BETWEEN EXTERNAL PAIRED SYSTEMS OVERVIEW

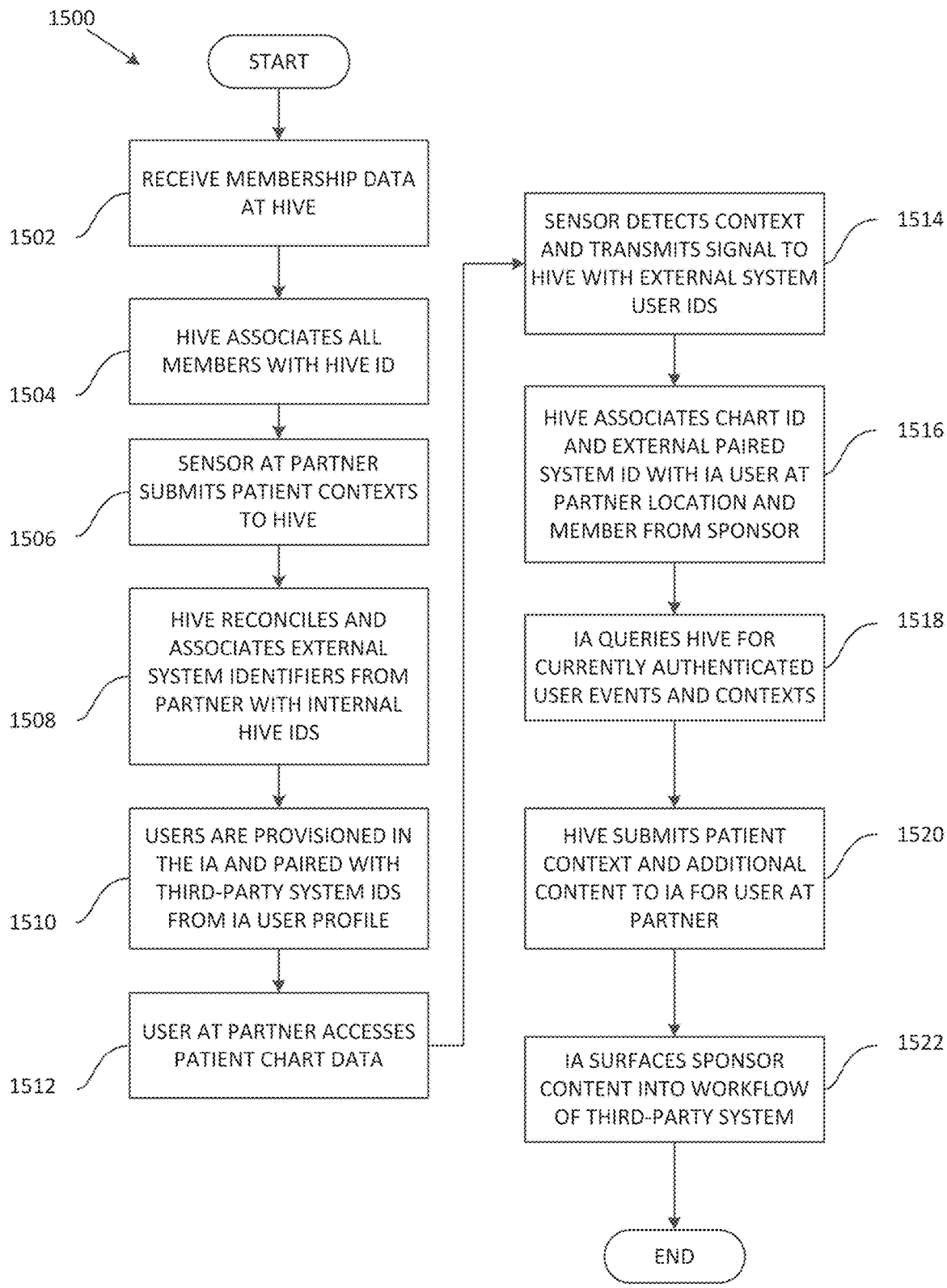
FIG. 15: EXEMPLARY IDENTITY MANAGEMENT BETWEEN EXTERNAL PAIRED SYSTEMS FLOWCHART

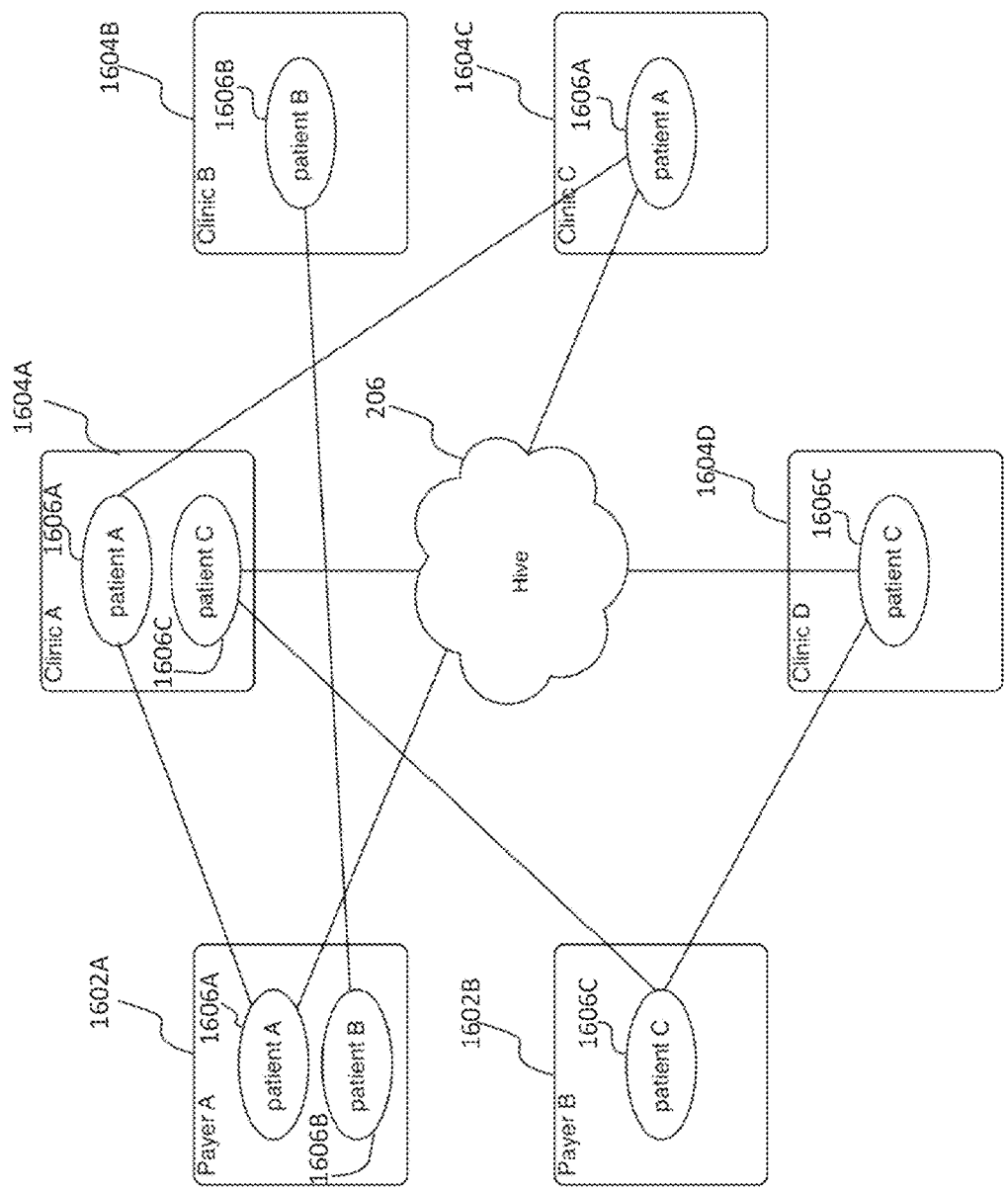
FIG. 16: EXEMPLARY FOLLOW A PATIENT OVERVIEW

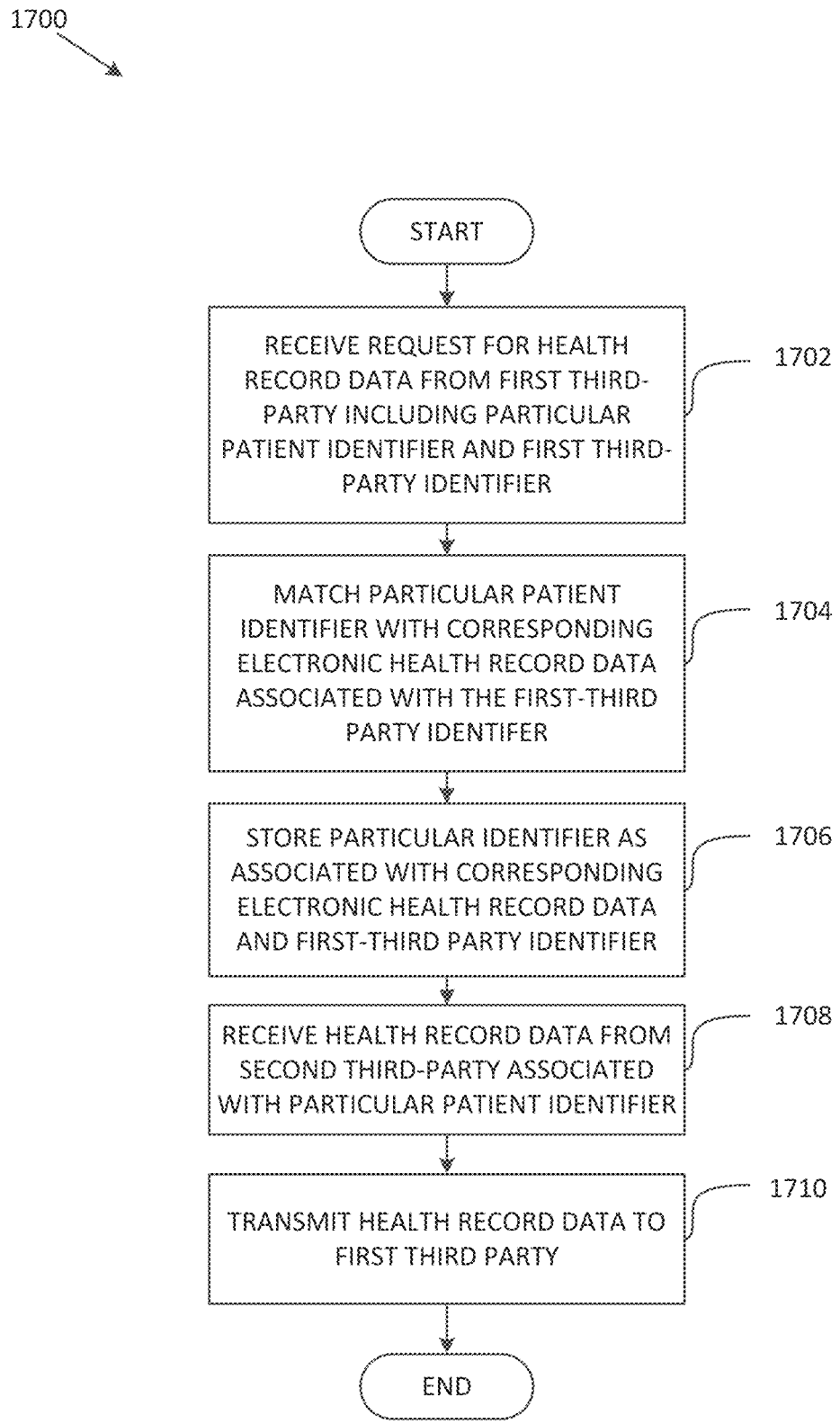
FIG. 17: EXEMPLARY FOLLOW A PATIENT PROCESS

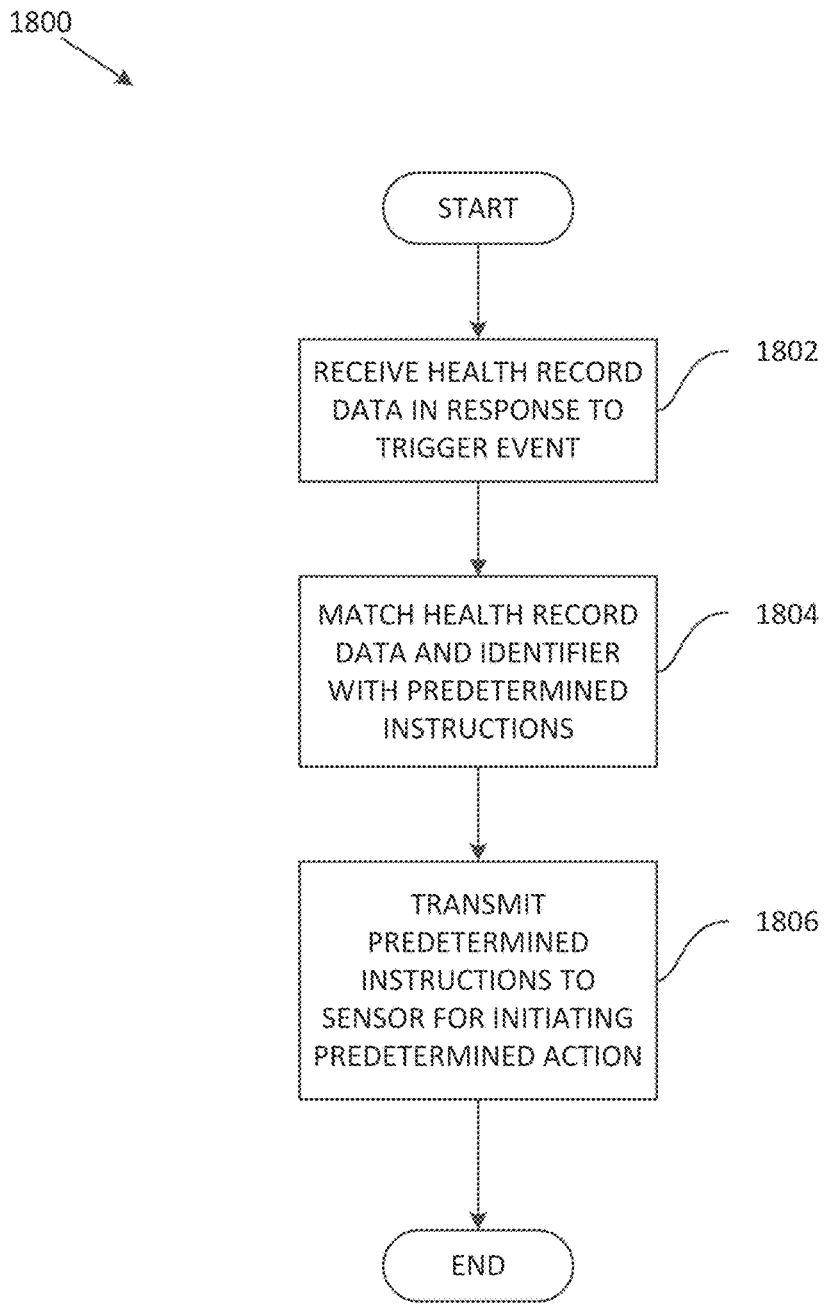
FIG. 18: EXEMPLARY TASK AUTOMATION PROCESS

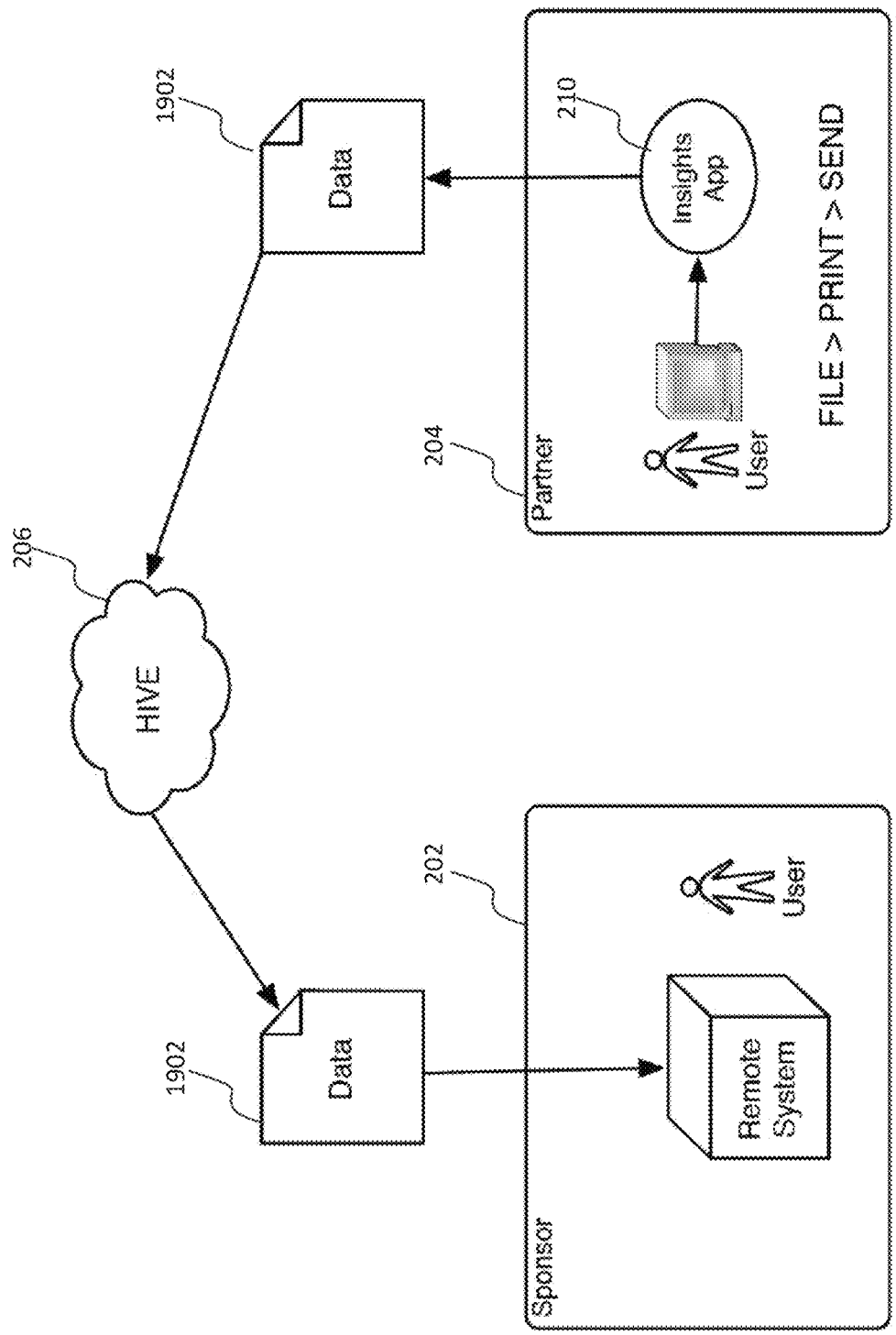
FIG. 19: EXEMPLARY PRINTER DRIVER OVERVIEW

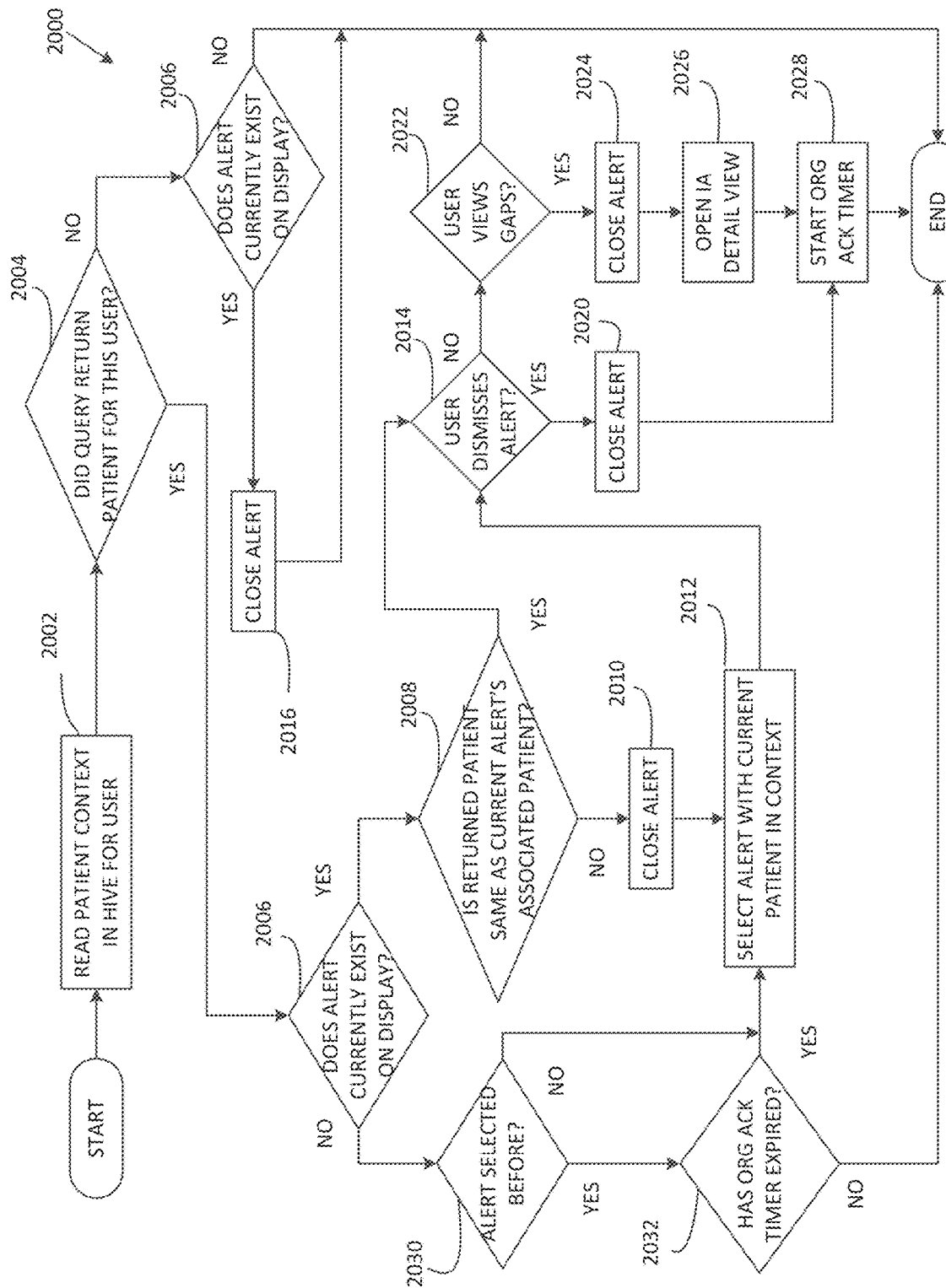
FIG. 20: EXEMPLARY INSIGHTS APPLICATION DECISION TREE LOGIC

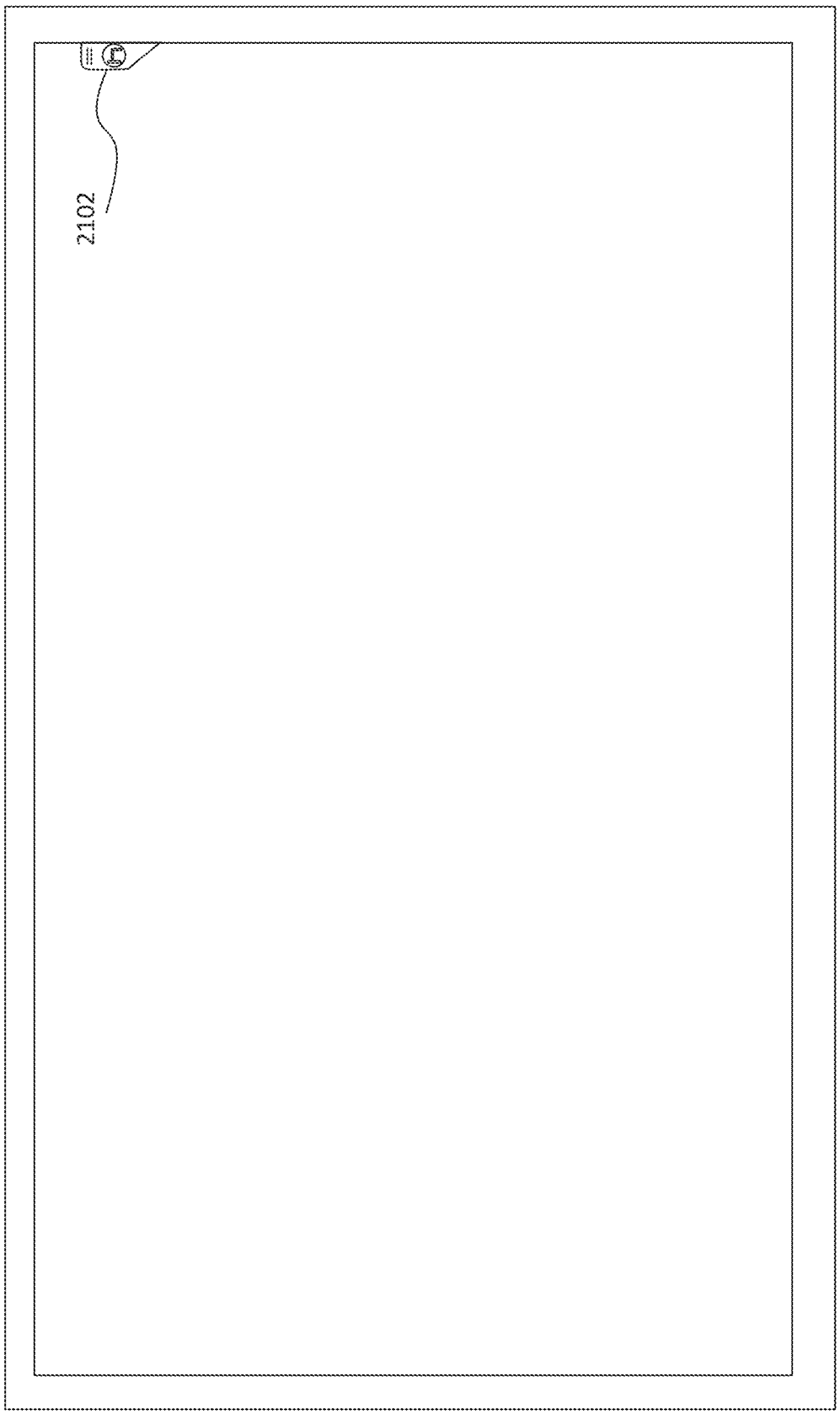
FIG. 21: EXEMPLARY APPLICATION TAB FEATURE

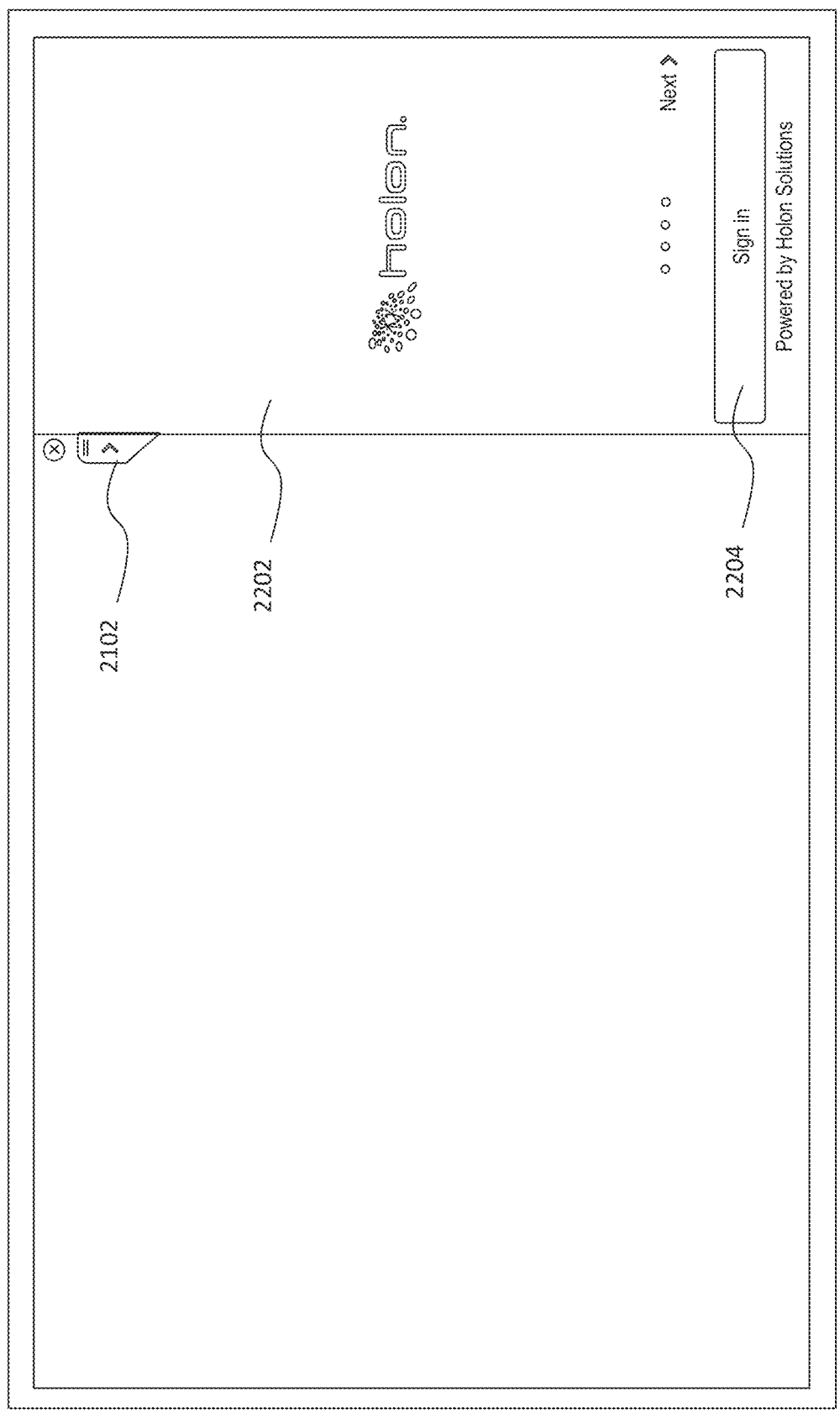
FIG. 22: EXEMPLARY SIGN-IN PANE APPLICATION FEATURE

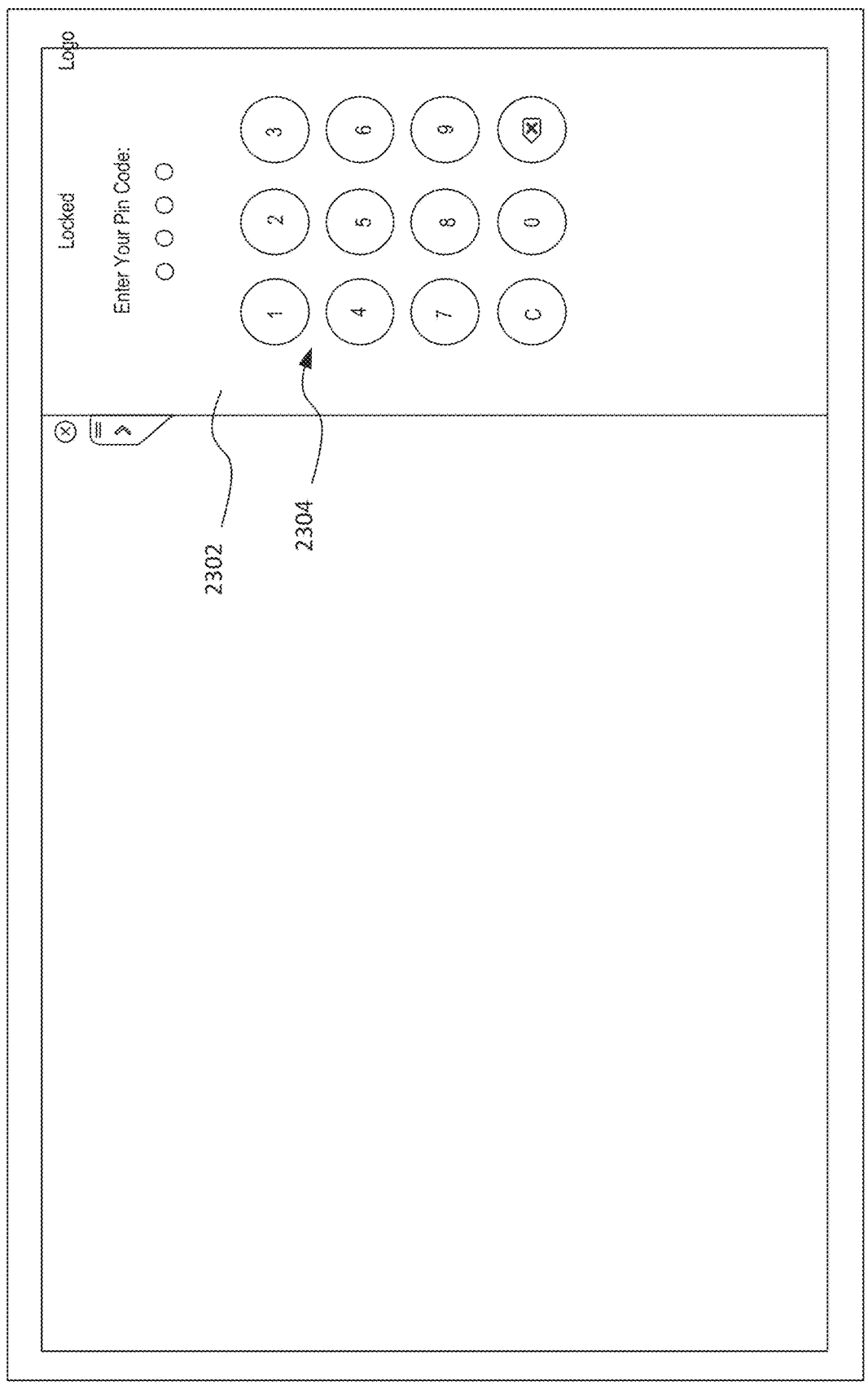
FIG. 23: EXEMPLARY PASSWORD PANE APPLICATION FEATURE

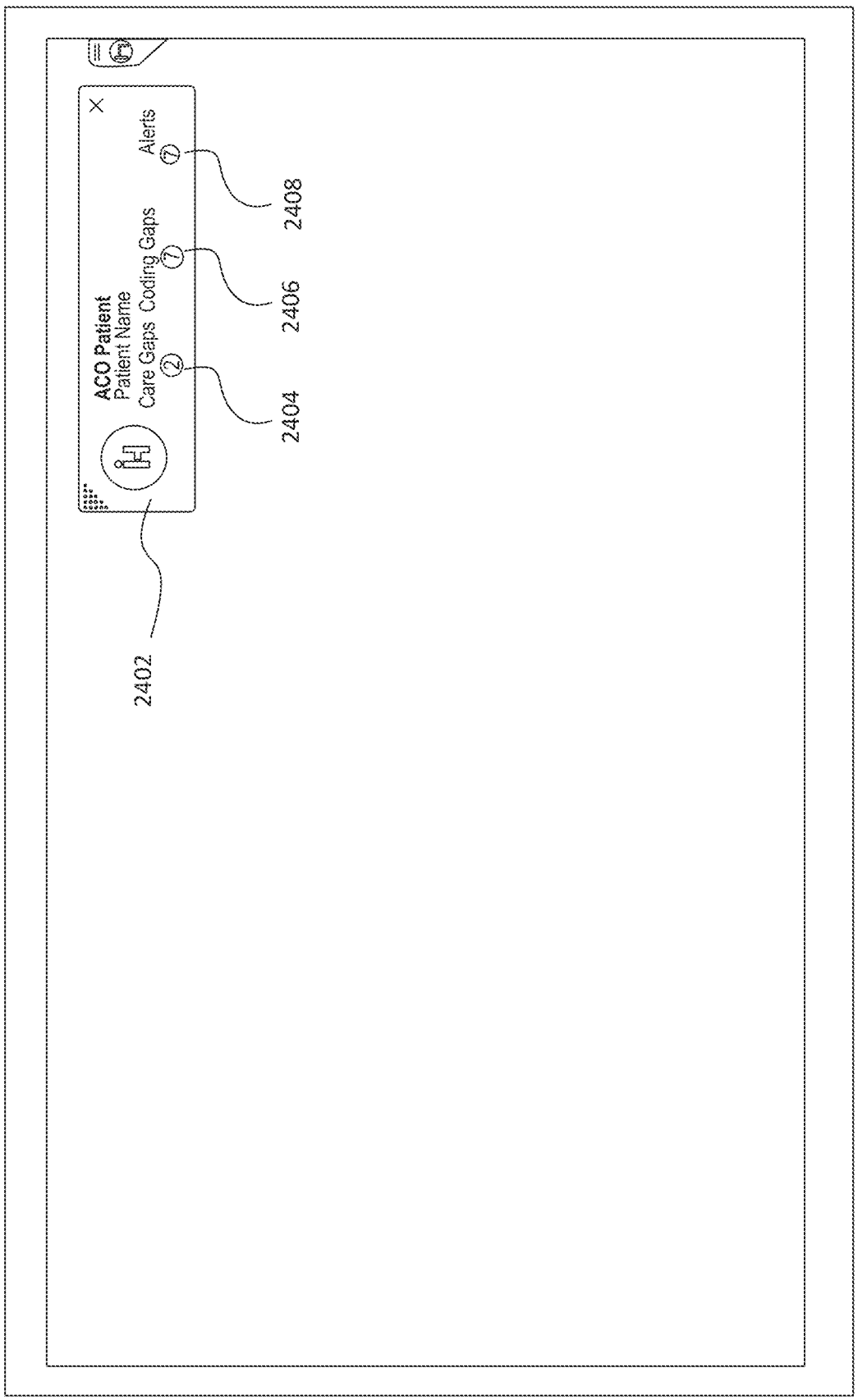
FIG. 24: EXEMPLARY POP-UP ALERT APPLICATION FEATURE

FIG. 25: EXEMPLARY CODING GAP PANE APPLICATION FEATURE

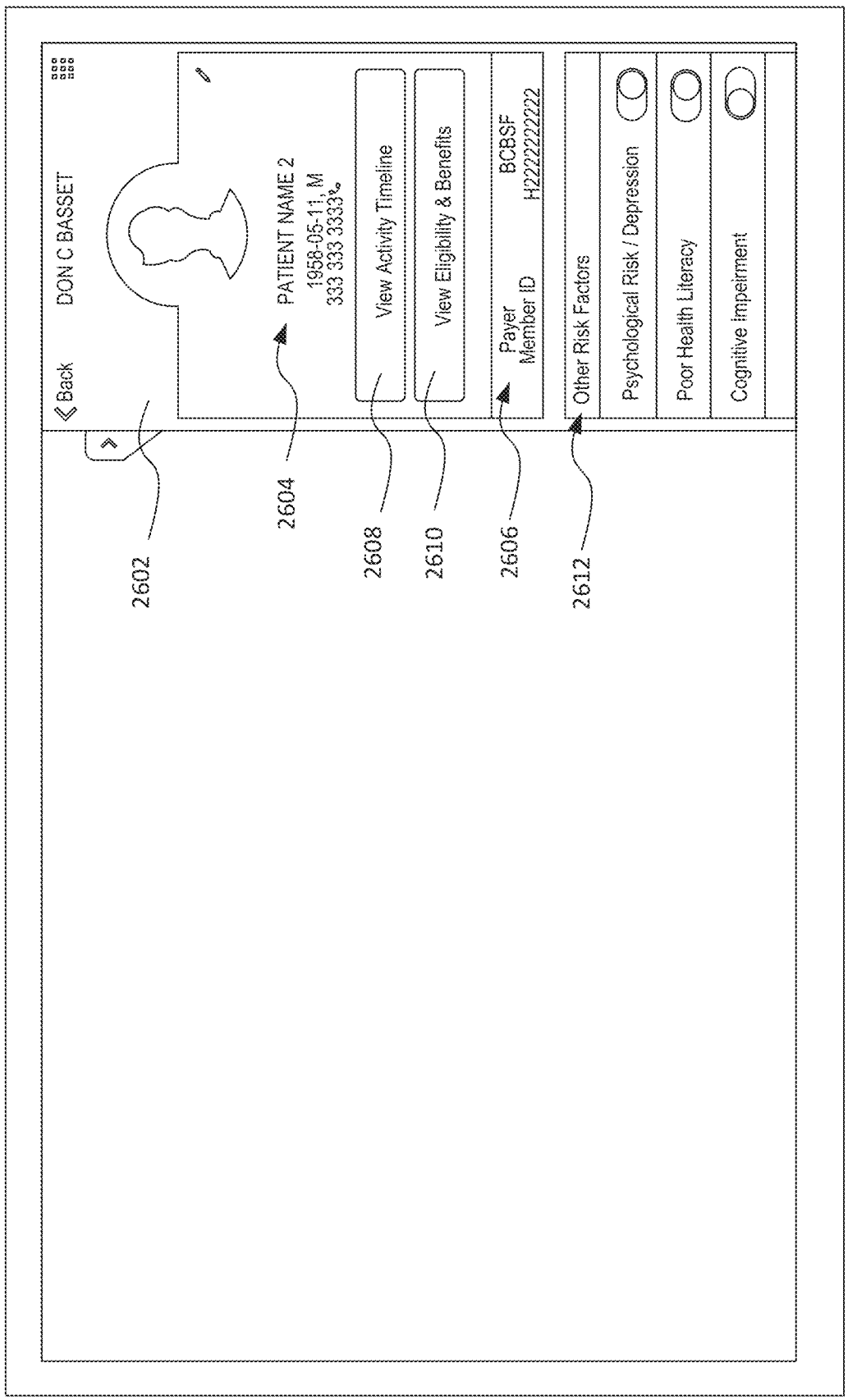
FIG. 26: EXEMPLARY USER PROFILE PANE APPLICATION FEATURE

FIG. 27: EXEMPLARY ELIGIBILITY SUMMARY PANE APPLICATION FEATURE

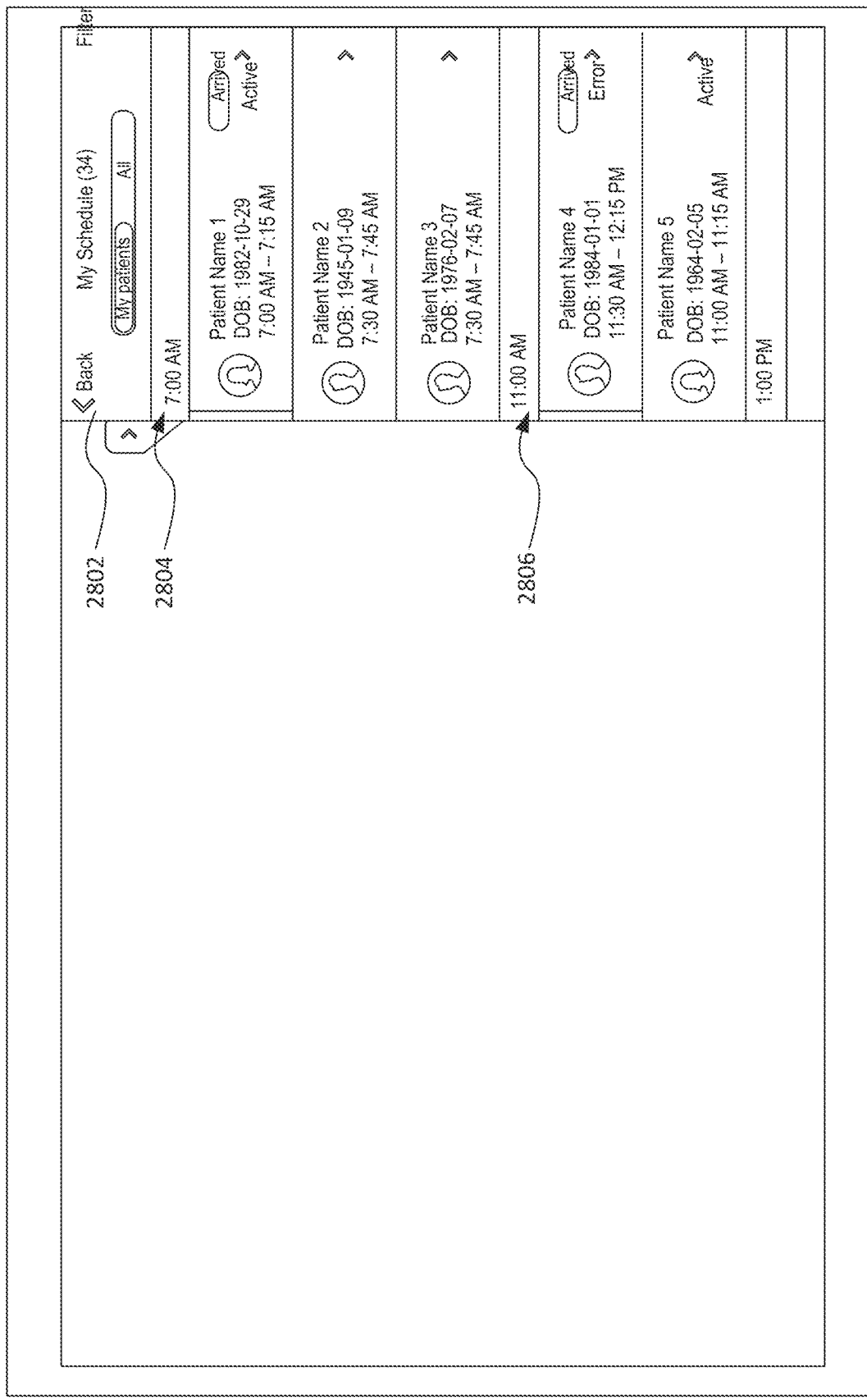
FIG. 28: EXEMPLARY SCHEDULE PANE APPLICATION FEATURE

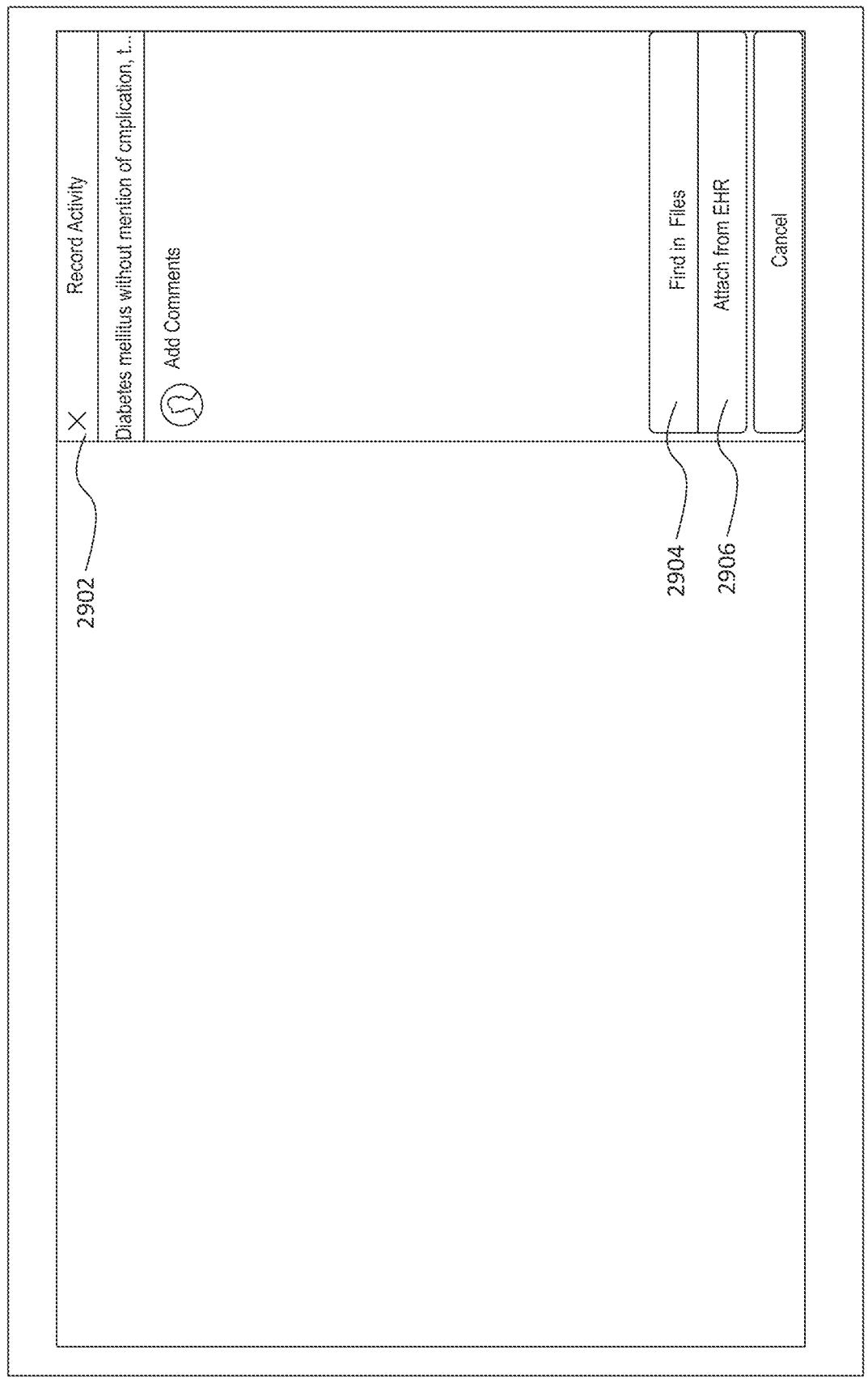
FIG. 29: EXEMPLARY RECORD ACTIVITY PANE APPLICATION FEATURE

SYSTEMS AND METHODS FOR SURFACING CONTEXTUALLY RELEVANT CONTENT INTO THE WORKFLOW OF A THIRD PARTY SYSTEM VIA A DISTRIBUTED ARCHITECTURE

CROSS REFERENCE TO RELATED APPLICATIONS

This application is a Continuation Patent Application of, and claims the benefit of and priority to, U.S. Non-Provisional patent application Ser. No. 17/194,426, filed on Mar. 8, 2021, and entitled "SYSTEMS AND METHODS FOR SURFACING CONTEXTUALLY RELEVANT CONTENT INTO THE WORKFLOW OF A THIRD PARTY SYSTEM VIA A DISTRIBUTED ARCHITECTURE," which is a Continuation Patent Application of, and claims the benefit of and priority to, U.S. Non-Provisional patent application Ser. No. 15/796,391, now issued U.S. Pat. No. 10,984,897, filed on Oct. 27, 2017, and entitled "SYSTEMS AND METHODS FOR SURFACING CONTEXTUALLY RELEVANT CONTENT INTO THE WORKFLOW OF A THIRD PARTY SYSTEM VIA A DISTRIBUTED ARCHITECTURE," which is a Non-Provisional Patent Application of, and claims the benefit of and priority to, U.S. Provisional Patent Application No. 62/413,615, filed on Oct. 27, 2016 and entitled "SYSTEMS AND METHODS FOR SURFACING CONTEXTUALLY RELEVANT CONTENT INTO THE WORKFLOW OF A THIRD PARTY SYSTEM," the disclosures of which are incorporated by reference in their entireties as if the same were fully set forth herein.

TECHNICAL FIELD

The present disclosure relates generally to surfacing electronic health record data into third-party workflows using a unique computer hardware architecture and software.

BACKGROUND

In 2009, legislation was enacted establishing the Office of the National Coordinator (ONC) to carry out the directives contained in the American Recovery and Reinvestment Act (ARRA) and the Health Information Technology for Economic and Clinical Health (HITECH) Act, which aimed at incentivizing provider organizations to adopt and implement new healthcare technologies called Electronic Medical Record (EMR) systems to better manage overall patient care as a response to a lack of technology adoption in previous years. As of 2011, Electronic Health Record (EHR) systems, as defined by the Centers for Medicare and Medicaid Services (CMS) as being required for Meaningful Use (MU) in order for Eligible Providers (EP) to receive incentive payments tied to care coordination, are at last becoming more widely adopted.

Meanwhile, other risk-based incentive programs, focusing on quality outcomes for populations, are gaining traction from an ever-changing landscape of market participants such as private insurance companies seeking to supplement Medicare beneficiary risk mitigation as a response to the Affordable Care Act (ACA) enacted by the federal government on Mar. 23, 2010. As part of this evolution, the U.S. federal government has committed to those privately held insurance companies, in what has come to be known as the Medicare Advantage (MA) program, that if the quality of care improves while the cost of care is lowered all while keeping patient satisfaction levels high (i.e. the Triple AIM), greater incentive payments shall be awarded while Medicare beneficiaries are under their management and control as weighted against a quality rating measurement scale known as the "Five-Star Quality Rating System." The goal of this CMS-defined quality rating system is to measure a Medicare beneficiaries' experience with their health plans and the health care system overall. This recent evolution has driven many private insurance companies to advance their employment of analytic strategies across their networks in an effort to gain greater efficiencies related to chronic care management as well as risk mitigation practices. In turn, the correlation of EHR-generated patient data married to health plan analytic membership data optimizes the opportunity for the ACA to have a greater impact on overall population health outcomes.

In response to these changes in administrative incentive payments, private insurers have positioned themselves to becoming more tightly affiliated with their enrolled members' EPs as they now have a driving force to better balance membership risk to incentive payments, as that ties to both health plan and EP revenues. This has led to the rise of a payment distribution arrangement whereby the insurance plan may share certain incentive payments or savings with partnering clinical entities known as Accountable Care Organizations (ACO) in what has been termed a Medicare Shared Savings Plan (MSSP) created in 2011 by the federal government's Health and Human Services (HHS) division. In these arrangements, the insurance company may incentivize primary care physicians for better communicating the risk of a plan member under their care. This is called a Medicare Risk Adjustment and is a core concept in many risk reduction programs.

In 2015, the most common risk adjustment method used in MA risk reduction programs is a manual chart audit. This audit is typically conducted by a private insurer's employee who has been deployed onsite to capture and collect all the clinical documentation necessary to bolster a private insurer's ability to appropriately assess a member's overall risk such that the member may be categorized into suitable stratified risk panels thereafter. In other cases, providers have lobbied to be allowed to risk adjust their own patients without manual chart audit intervention. However, prior to these events, CMS created what are known as Hierarchical Conditional Codes (HCC) in 2004 to assist private insurers with the risk stratification process when adjusting bundled incentive payments (e.g. capitation payments) for the monetary expenditure of their members/enrollees. Therefore, in order for the providers to get what they have lobbied for, insurance companies may need to find a way to support not only risk identification via an electronic medium, but also empower providers to capture HCC on their own at the time of risk adjustment. To combat this challenge, electronic web portals were developed to enable providers an electronic way of supplying risk adjustment data to health plans in order to qualify for their shared savings incentives. This requires immense documentation of clinical activity external to the provider's workflow, which unfortunately is a time-consuming effort that replicates data that has likely already been captured within an EHR system. Additionally, EHR systems are generally "closed," so the data stored therein cannot be easily accessed.

Therefore, there is a long-felt but unresolved need for a system or method that: a) more efficiently collects and analyzes data by reducing data collection time and replication; b) connects disparate systems via a novel computer architecture; c) improves existing EHR computer systems; and d) interacts seamlessly with provider EHR systems and insurance company data analytics systems to support Medicare risk reduction programs in an effort to improve the overall course of care for patients and better health outcomes for populations.

BRIEF SUMMARY OF THE DISCLOSURE

Briefly described, and according to one embodiment, aspects of the present disclosure generally relate to systems and methods for providing contextually relevant content sourced from third party analytics systems to be surfaced within the current workflow of a separate third party system, particularly healthcare specific clinical and financial systems. A technical solution including an Insights Application (IA), as described herein, enables organizations such as insurance companies and other population health analytics entities (Sponsoring Organization, or Sponsors) to promote their analytic content, as calculated by their proprietary analytics algorithms and published by their proprietary analytic platforms, to healthcare providers (Partner Organization, or Partners) within the workflow of the third party systems to which the healthcare providers use. The content is generally targeted to specific persons (patients) who fall within certain predefined inclusionary criterion such as being an enrollee of a Sponsor's (e.g. insurance company) health plan or by being a member of a Sponsor's (e.g. ACO) membership. Generally, the IA has awareness of a patient record (chart) open in the third party system and surfaces content such as an IA summary message to the end user in the form of a non-intrusive, small new window on the user's screen that conveys a summary of applicable content for that member. By design, this "alert" may appear on top of other screen content on the user's computer workstation monitor. The default location of this alert may be the upper right hand corner of the screen, but may be repositioned at any time and saved as a user preference. The content of such an alert may include, but is not limited to, information related to the patient as having been enrolled in an ACO, the patient having outstanding gaps in their overall care (as measured annually by CMS for MA patients), or any other alerts pertaining to the current and/or previous financial coding conducted for billing purposes for submittal to the Sponsoring Organization. These coding gaps become risk adjustment opportunities thereafter as previously described. The alert, once clicked, may disappear from the screen and an IA details view may slide into view from the right. This is the primary view of the IA and provides much greater detail surrounding the content as summarized in the alert and gives greater control to the Partner Organization's end user to supply additional information back to the Sponsoring Organization via the IA.

According to one aspect, the system offers a context-sensing system (Context Sensor, or Sensor) driven by configurable templates to create a sensory ability, wherein each Sensor operates independently from the IA as well as not requiring participation of the third party system vendor. In most circumstances, all that may be needed for proper implementation is assistance from the local Partner's (i.e. physician's office) information technology resources staff. Generally, operation of the Sensor matches specific person identifiers as sourced by both parties (system one person data to system two person data) and correlates the common identity prior to promoting this correlation as a common identifier to a micro-services application programming interface (API) known as Hive.

More particularly described, aspects of the present disclosure relate to a system for correlating third party user and patient identifiers to related Sponsor identifiers. This provides a mechanism to sense the moment in time a user of a third party system brings patient data into focus (e.g. opens a chart) and determines if any external content exists about that patient such that the IA may in near real-time present an alert to the Partner's end user.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 1 is an exemplary high-level overview of a Medicare Advantage risk reduction program, according to one aspect of the present disclosure;

FIG. 2 is an exemplary high-level overview of an operational environment, according to one aspect of the present disclosure;

FIG. 3 is a high-level overview of the exemplary system architecture, according to one aspect of the present disclosure;

FIG. 4 is a diagram illustrating a cloud-based micro-services architecture, according to one aspect of the present disclosure;

FIG. 5 is a diagram illustrating an application architecture, according to one aspect of the present disclosure;

FIG. 6 is a diagram illustrating a sensor architecture, according to one aspect of the present disclosure;

FIG. 7 is a sequence diagram illustrating a data provisioning process, according to one aspect of the present disclosure;

FIG. 8 is a sequence diagram illustrating an organization and user provisioning process, according to one aspect of the present disclosure;

FIG. 9 is a sequence diagram illustrating a membership attestation and exemplary identity matching process, according to one aspect of the present disclosure;

FIG. 10 is a sequence diagram illustrating a remote system context control process, according to one aspect of the present disclosure;

FIG. 11 is a sequence diagram illustrating a context sensitive alert and data presentation process, according to one aspect of the present disclosure;

FIG. 12 is a flowchart illustrating an exemplary code gap detection process, according to one aspect of the present disclosure;

FIG. 13 is an exemplary illustration of code gaps in a data structure, according to one aspect of the present disclosure;

FIG. 14 is a high-level illustration of identity management between external paired systems, according to one aspect of the present disclosure;

FIG. 15 is a flowchart of the exemplary identity management process, according to one aspect of the present disclosure;

FIG. 16 is a diagram illustrating cross-platform identification matching, according to one aspect of the present disclosure;

FIG. 17 is a flowchart of the exemplary follow and patient process, according to one aspect of the present disclosure;

FIG. 18 is a flowchart of the exemplary task automation process, according to one aspect of the present disclosure;

FIG. 19 is a diagram illustrating an exemplary data exporting process, according to one aspect of the present disclosure;

FIG. 20 is a flowchart of an exemplary application context surfacing decision tree, according to one aspect of the present disclosure;

FIG. 21 is an exemplary application tab feature, according to one aspect of the present disclosure;

FIG. 22 is an exemplary sign-in pane application feature, according to one aspect of the present disclosure;

FIG. 23 is an exemplary password pane application feature, according to one aspect of the present disclosure;

FIG. 24 is an exemplary pop-up alert application feature, according to one aspect of the present disclosure;

FIG. 25 is an exemplary coding gap pane application feature, according to one aspect of the present disclosure;

FIG. 26 is an exemplary user profile pane application feature, according to one aspect of the present disclosure;

FIG. 27 is an exemplary eligibility summary pane application feature, according to one aspect of the present disclosure;

FIG. 28 is an exemplary schedule pane application feature, according to one aspect of the present disclosure; and FIG. 29 is a record activity pane application feature, according to one aspect of the present disclosure.

DEFINITIONS

Prior to a detailed description of the disclosure, the following definitions are provided as an aid to understanding the subject matter and terminology of aspects of the present systems and methods, are exemplary, and not necessarily limiting of the aspects of the systems and methods, which are expressed in the claims. Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

1. Electronic Health Record (EHR): In one embodiment, an electronic health record may include health related information pertaining to a particular individual, which may be stored and shared digitally. Electronic health and medical records may include information such as name, date of birth, gender, age, Medicare beneficiary identifiers, surgical history, prescriptions, allergies, various health conditions, etc. The term "EHR" may be defined by the Centers for Medicare and Medicaid Services (CMS), and said EHR systems are contemplated herein, but the definition of EHR in this document is not limited to the CMS definition of the same.

2. Sponsor Organization: In various embodiments, a Sponsor Organization, or Sponsor, may be a healthcare insurance provider, a Managed Services Organization (MSO), an Accountable Care Organization (ACO), a healthcare claims clearinghouse or similar organization that may provide insurance policies to individuals or other services to healthcare providers.

3. Partner Organization: In one embodiment, a Partner Organization, or Partner, may be a healthcare provider/establishment such as a hospital or clinic.

4. Insights Application (IA): In one embodiment, a software configuration within the computing system of a Partner that allows content such as contextually relevant information to be surfaced into a third party work flow such as an EHR. In various embodiments, the IA runs one or more additional software applications/processes. In certain embodiments, these applications provide alerts to the user of the computing system operatively hosting the IA, and then further provide additional detailed information regarding the content if the alert is selected. In one embodiment, the information regarding these alerts is sent to the IA from Hive in response to the applicability of the patient in focus (e.g. user opens patient chart), determined by the Context Sensor querying the third party system.

5. Holon Connect Engine: In one embodiment, a software configuration included in Hive.

According to aspects of the present disclosure, the Holon Connect Engine operates within Hive and receives Sponsor membership data from a Sponsor's Common Data Access Point (CDAP).

6. Context Sensor (or sensor): A general name given to a software configuration for sensing a triggering event via various mechanisms discussed herein. Upon sensing a triggering event, the Sensor may send, retrieve, request, and/or transmit information to another system, such as Hive or take some other action. In particular embodiments, a Sensor is operatively connected to a third party system and may be granted access to electronic health records, or may be configured to monitor certain electronic health records that are actively opened on a provider's screen (where opening of an electronic health record is a triggering event). As will be understood from discussions herein, the system may include more than one Sensor. In general, the Sensor is configured to monitor the activity within the third party system and trigger various actions based on activity regarding individuals or particular aspects of a set of information provided by the Sponsor.

7. Hive: In one embodiment, a proprietary term for a cloud based micro-services architecture that includes multiple databases and web servers configured to map user identifications as well as associate certain trigger events with a corresponding action. Hive may be configured to match and associate particular individuals across various organizations, such as individuals that visit more than one doctor. Hive may process large data sets, such as a Sponsor's membership list, into an appropriate format. In certain embodiments, Hive processes and stores data as received from a Sponsor and acts as the storage faculty for all inbound and outbound data requests as originated by the IA or Sensor.

8. CollaborNet: In various embodiments, a proprietary name for a combination of services including Hive as well as software services deployed on a client's systems, namely the IA and Sensor. It should be understood from the discussion herein that CollaborNet is, in at least one embodiment, a configuration of software and/or hardware that creates a secure network that manages the assembly, packaging, routing, and delivery of healthcare information among and between care delivery organizations, namely Sponsor Organizations and Partner Organizations. CollaborNet may monitor and/or receive data from one or more sources, catalogs contextual information from those systems, and then utilize content in focus in the third party system (e.g.

patient or schedule information in an EHR) to display content corresponding to information sourced from the aforementioned systems.

9. Common Data Access Point (or CDAP): In one embodiment, a location or memory address within a computing system wherein particular data is stored and made available to various third party computing systems (i.e. REST API, or sFTP location). According to aspects of the present disclosure, the CDAP is accessible by both the Sponsor Organization and the Holon Connect Engine of Hive.

DETAILED DESCRIPTION OF FIGURES

Overview

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described of illustrated embodiments, and any further applications of the principles of the disclosure as illustrated therein are contemplated as would normally occur to one skilled in the art to which the disclosure related. All limitations of scope should be determined in accordance with and as expressed in the claims.

Aspects of the present disclosure generally relate to systems and methods for efficiently providing third-party data over computer networks, improving database systems to increase speed of delivery of such data and quality of third-party clinical and financial information through novel computer injection mechanisms. Further aspects of the present systems and methods relate to providing contextually relevant content sourced from third-party analytics systems to be surfaced within the current workflow of a separate third party system, particularly healthcare specific clinical and financial systems.

The healthcare information technology industry supports satisfying mandates and policies set forth by the federal government with regard to healthcare. Generally, private insurance companies have assumed the task of providing health care insurance to the population. These private companies have promised better results in all aspects of the triple-AIM (better quality/experience of care, better population health, lower cost of care per capita) as measured and rated on a Five-Star basis by CMS, in return for greater financial incentives when underwriting risk for Medicare patients in what has come to be known as Medicare Advantage plans. In some cases, a half-star rating increase may be valued at $30-million in revenue for a membership of 50,000 Medicare members. These private companies earn their star ratings based on a formula that incorporates various information such as information provided by doctors and patient satisfaction. In many scenarios, when a person files an insurance claim through a health clinic or another establishment that accepts health insurance, the claim is processed through an automatic clearing-house (ACH). In some scenarios, the entire process of adjudicating a claim, receiving payment/reimbursement, reporting the delivered care, as well as receiving other relevant information regarding the patient and their adjusted risk from the private company may take upwards of 90 days.

Aspects of the present disclosure solve the above problem with a technical solution, namely providing a distributed architecture system at least allowing for additional content and information related to the delivery of care as well as any outstanding gaps in care to be surfaced within the workflow of an electronic health record at the point and time of care, thus representing an improvement on delivery of the information regarding the patient and their adjusted risk taking upwards of 90 days.

Medicare Advantage—Exemplary System Aspects

Referring now to the figures, for the purposes of example and explanations of the processes and components of the disclosed systems and methods, reference is made to FIG. 1, which illustrates an exemplary, high-level overview of a Medicare Advantage risk reduction program, according to one embodiment. As will be understood and appreciated, the conceptual overview shown in FIG. 1 represents merely one approach or embodiment of the present systems, and other aspects are used according to various embodiments of the present system. Included in the present embodiment is a representation of the U.S. government 102, insurance companies 104A and 104B, a hospital 106, and clinics 108A, 108B, and 108C. Distributed throughout these elements are patients 110A, 110B, and 110C. The description below is an overview of the exemplary process of a Medicare Advantage risk reduction program and describes how the above-mentioned elements may correspond to the process.

In one embodiment, the U.S. government 102 oversees a Medicare Advantage risk reduction program as well as the Medicare Advantage reimbursement program, which patients 110A, 110B, and 110C are enrolled in. In the present embodiment, the U.S. government 102 has assigned certain responsibilities under the Medicare Advantage reimbursement program to private insurance companies 104A and 104B. In various embodiments, and in return for ensuring high quality of care for a relatively low price, the U.S. government 102 may reward insurance companies 104A and 104B with monetary compensation. In a particular embodiment, when patient 110B visits clinic 108A, as shown in FIG. 1, the clinic 108A will file a claim with insurance company 104A with which patient 110B is enrolled. Continuing with this embodiment, the clinic 108A will also report the medical record and a risk adjustment if necessary. In this embodiment, reporting a risk adjustment to insurance company 104A may allow for insurance company 104A to reevaluate how patient 110B is insured in order to offer them more appropriate coverage. In return for reporting the medical record, the risk adjustment information, and the claims of services rendered, insurance company 104A, in this embodiment, will compensate clinic 108A at a higher rate for the services provided to patient 110B should there be sufficient evidence supporting patient 110B as having greater risk than previously documented.

According to various aspects of the present disclosure, the information such as the medical record, risk adjustment information, and claims provided by the clinic 108A, can be used by insurance company 104A in order to prove to the U.S. government 102 that quality care is being provided to these members. As a result, the U.S. government 102 may reward insurance company 104A by increasing insurance company 104A's CMS's Five-Star quality rating, which will result in larger reimbursements for insurance company 104A going forward.

Continuing with FIG. 1, patient 110A may visit both the hospital 106 and clinic 108B. In this scenario, and according to one embodiment, both the hospital 106 and clinic 108B may file a claim with insurance company 104A with which patient 110A is enrolled. Both the hospital 106 and clinic 108B may also report the medical record and a risk adjustment if necessary. Also illustrated in FIG. 1, patient 110C may visit both the hospital 106 and clinic 108C. In this scenario, and according to various embodiments, both the hospital 106 and clinic 108C may file a claim with insurance company 104B and also may report the medical record and a risk adjustment if necessary. Generally, a particular patient may visit more than one doctor or healthcare provider over a period of time for various reasons. In some scenarios, a particular patient may have a primary physician but due to a medical emergency is treated at a hospital. Similar to the example above regarding patient 110B, reporting claims, medical records, and risk adjustments back to insurance companies allows for the insurance companies to compensate for claims at a higher rate, reevaluate appropriate insurance coverage based on health and risk, and to allow for potential Five-Star rating adjustments in turn, yielding greater reimbursement payments from CMS. According to various aspects of the present disclosure, detecting code gaps in electronic heath records allows for the system to further identify areas for risk adjustment, as well as improved care, therefore providing the compensation benefit to the reporting healthcare provider.

Exemplary Closed Loop System Analytics

Turning now to FIG. 2, an exemplary high-level overview of an operational environment 200 is illustrated in accordance with various aspects of the present disclosure. According to various aspects of the present disclosure, the embodiment shown in FIG. 2 illustrates an improved distributed architecture system for distributing information to and from normally closed systems, generally for augmenting the presentation of electronic health records with surfaced third party content in order to improve the completeness and accuracy of health information presented to providers at the point and time of care. Also illustrated in FIG. 2 is a timely mechanism for a Partner to submit health record data back to a Sponsor. As will be understood and appreciated, the conceptual overview shown in FIG. 2 represents merely one approach or embodiment of the present system, and other aspects are used according to various embodiments of the present system.

In one embodiment, the system 200 includes at least a Sponsor 202 (e.g. payer/insurance company), a Partner 204 (e.g. ambulatory health clinic), a micro-services cloud infrastructure 206 (including the combination of Hive and the Holon Connect Engine), a Common Data Access Point (CDAP) 208, an Insights Application (IA) 210 within the Partner environment 204, an analytic system 212 within the Sponsor environment 202, and a Sensor 214 operatively connected to the EHR system 226 within the Partner environment 204. In various embodiments, the Sponsor organization 202 and the Partner organization 204 are in operable communication over any suitable network (e.g., wired network, wireless LAN, CollaborNet, etc.).

For the purpose of describing the present embodiment, consider three scenarios (Scenarios A, B, and C), each scenario involving a patient entering a doctor's office (Partner organization 204) for a medical examination. In Scenario A, the particular patient is a repeat patient and the Partner organization 204 maintains an electronic health record for the patient. In response to the doctor opening the patient's electronic medical record, a light-weight software configuration referred to herein as the sensor queries the cloud-based micro-services system 206 for any healthcare data associated with the patient. In various embodiments, included in the query to the cloud-based micro-services system 206 is at least a portion of chart data 216 and a patient identifier. In one embodiment, the cloud-based micro-services system 206 is operable to retrieve any corresponding health records relating to the particular patient and further compare the portion of chart data 216 to any data stored in the cloud-based micro-services system 206. In particular embodiments, comparing the data may expose gaps in healthcare data or coding. According to various aspects of the present disclosure, these exposed gaps 228 are transmitted to the Insights Application 210 at the doctor's office and are further presented to the doctor in the form of an alert, pop-up or slide out bar, notification, etc. Providing the doctor with information relating to gaps on care or coding allows for the doctors to provide the most informed care possible while also achieving other advantages such as saving costs during the process of filing Medicare claims.

In Scenario B, and according to one embodiment, consider that the patient enters the doctor's office (e.g., Partner 204) and is a first-time patient. In various embodiments, prior to administering treatment to this patient, the doctor may collect information from the patient such as name, date of birth, social security number, medical insurance information, etc. Furthermore, the doctor may enter this information into his/her respective EHR/electronic medical record system 226 and proceed with treating the patient. According to various aspects of the present disclosure, installed on the doctor's computer system are the Sensor 214 and Insights Application 210 as described herein. As a result of providing care to the patient, the Sensor 214 transmits a clinical summary and other relevant treatment information to the cloud-based micro-services system 206. In a particular embodiment, in response to receiving this data, the cloud-based micro-services system 206 determines other doctors (or healthcare organizations of interest) that are associated with the particular patient and further notifies the other associated doctors or providers of the recently provided care.

In Scenario C, consider the patient is a repeat patient at the doctor's office (e.g., Partner 204) and the doctor begins to prescribe the patient a new drug. According to various aspects of the present disclosure, the action of prescribing a new drug may be a preconfigured trigger event (detected by Sensor 214) that results in the system automatically executing a series of tasks. For example, and in response to detecting the trigger event, the system may determine if the patient's insurance is included in a list of excluded insurances, presenting an alert to the doctor if the patient's insurance will not cover the cost of the drug, and if the patient's insurance will cover the cost of the drug further automatically populating the prescription information.

In various embodiments and prior to each of the above three scenarios (or after), the cloud-based micro-services system 206 may receive member data 218 from the analytic system 212 of the Sponsor 202. According to various aspects of the present disclosure, the member data 218 may include a list of Medicare beneficiaries (e.g., "member list"). In some embodiments, a member list may include relevant information such as name, gender, date of birth, age, Medicare beneficiary identification, primary care provider information, gaps in clinical care, gaps in claims submission and coding, MSSP/MSO/ACO identifiers, etc. relating to the particular patients included in the member list. In a particular embodiment, the information contained in the member list may not be included in an electronic health record. In some embodiments, further information may include information pertinent to the Partner 204 at the time of care, which may be presented at this time.

In one embodiment, the Sponsor 202 includes a firewall (or another appropriate data protection mechanism) for protecting the member data 218 included in the analytic system 212. According to various aspects of the present disclosure, the member data 218 may be pushed to the Common Data Access Point 208 where the cloud-based micro-services system 206 may retrieve the member data 218 via the Holon Connect Engine 224.

In various embodiments, the system components included in the three scenarios above are described in further detail below, and the role of each component will be described accordingly.

In one embodiment, the Sponsor 202 is a payer or insurance company. In some cases, Sponsors 202 provide a service to a group of enrolled members. In the present embodiment, the Sponsor 202 provides health insurance to individuals enrolled in various health care plans. In one embodiment, analytic information (e.g., member data 218) regarding these individuals is stored in a database (e.g., analytic system 212) included within the computing systems of the Sponsor 202. Generally, member data 218 includes various information (e.g., name, gender, date of birth, age, primary care provider NPI, Medicare beneficiary identifier, etc.) regarding the individuals enrolled in a Sponsor 202's services will also be stored in the analytic system 212. As will be understood from discussions herein, the Sponsor 202 may perform any suitable data analytics associated with the quality of care provided, the coding of care delivered, patient outcomes, patient satisfaction, health records, etc.

In particular embodiments, and mentioned briefly above, the Sponsor 202's system may include a firewall to protect patient information (firewall not shown). Due to this firewall, the Sponsor 202 may push the member data 218 to a Common Data Access Point (CDAP) 208, outside the general firewall to be accessed by a connection engine 224 (e.g., Holon Connect Engine) included in the cloud-based micro-services system 206 to allow the cloud-based micro-services system 206 to retrieve or otherwise access the member data 218 (and/or other relevant data).

In one embodiment, the Partner 204 is a hospital or health clinic. Typically, Partners 204 provide a service to individuals on a case-by-case basis (e.g., a doctor provides medical treatment and advice to patients by appointment). In one embodiment, a Partner 204 may have a business relationship with a Sponsor 202 wherein the Sponsor 202 reimburses the Partner 204 for various provided services (e.g., through Medicare). In the present embodiment, this reimbursement for services is illustrated by the back and forth transaction of Medicare claims 220 and Medicare reimbursements 222 (although the system may be applicable to information and/or insurance other than Medicare).

In various embodiments, a patient may receive care from the Partner 204 and the Partner 204 may then file a claim 220 to the Sponsor 202 (insurance company) associated with the particular patient requesting reimbursement for the care provided. In one embodiment, the Sponsor 202 will process and approve the claim 220, assuming that the patient is enrolled in a plan with the Sponsor 202, and the Sponsor 202 will then send a reimbursement 222 to the Partner 204.

As mentioned above and according to one embodiment, a Common Data Access Point 208, or CDAP, may be a location within a computing system, computing network, or the like, where a particular set of information is pushed, transmitted, or stored in order to allow access to the information by third parties (e.g., through a suitable API, SSH tunnel, or the like). In the present embodiment, the member list/member data 218 including the enrolled members of a Sponsor's 202 service is transmitted to the CDAP 208, along with any other additional files or analytic information relevant to the overall care or plan information of the membership, in order for the cloud-based micro-services system 206 to access the data.

As will be understood from discussions herein, the Sponsor 202 may transmit data, such as member data 218, to the CDAP 208 at regular intervals and/or substantially constantly upon receiving new information. In one embodiment, the Sponsor 202 updates and transmits information to the CDAP 208 approximately every thirty days. In some embodiments, the Sponsor 202 updates and transmits information to the CDAP 208 in varying frequencies such as every day, every 7 days, every 60 days, etc.

In one embodiment, cloud-based micro-services system 206, also referred to herein as Hive, may be a web based server cluster or computing system that is configured to process and store large amounts of information, and distribute the information to other computing systems. In the present embodiment, Hive 206 is configured to periodically pull the member list and member data 218 from the CDAP 208 and process it into a non-relational format that is normalized and appropriate to be distributed within the system. In various embodiments, Hive 206 communicates this processed information to the IA 210, which may then present this information to a user of the present system (e.g., care provider, doctor, etc.) in the form of a surfaced content summary alert.

In one embodiment, the Insights application (IA) 210 is a software configuration within the Partner environment 204, which allows contextually relevant information to be surfaced into a third party workflow. In particular embodiments, the IA 204 represents two software applications: 1) an application that provides alerts including summary information from Hive, as sourced from the Sponsor 202, to the computing system of the Partner 204, and; 2) an application that presents a larger set of information if the alert is selected by the Partner 204 user and provides further information and functionality, such as a mechanism for electronic communication between the Partner 204 and the Sponsor 202 (e.g., via Hive 206). In certain embodiments, an alert is a notification to the Partner 204 produced by Hive 206 based on the information received by the Sensor 214 and the information from the Sponsor 202 that the patient may have certain care gaps that need to be addressed.

For example, the individual may be in the Partner's office 204 for issues relating to a fever, but upon opening up the individual's electronic health record the doctor may be alerted by the IA 210 that the individual has shown gradual increase in blood pressure over the past five years and should be evaluated for hypertension, especially if the individual has not been seen in over a year. In various embodiments, the information regarding the past five years of blood pressure readings may be included in the electronic health record or included in data from Hive 206 that has been acquired and normalized from the Sponsor 202. In one embodiment, Hive 206 is configured to determine relationships between patient identities across disparate Partners 204 and can surface care alerts via the IA 210 as sourced from Sponsors 202 to their individual Partners 204.

In one embodiment, the Sensor 214 is a software configuration (e.g., software service, plug-in, backend code, etc.) for sensing a triggering event via various mechanisms discussed herein. Upon sensing a triggering event, the Sensor 214 may send, retrieve, request, and/or transmit information to another system, such as Hive 206. In particular embodiments, a Sensor 214 is operatively connected to a Partner system 204 and may be granted access to electronic health records, or may be configured to monitor certain electronic health records that are actively opened on a provider's screen (where opening of an electronic health record is a triggering event). As will be understood from the discussions herein, the system may include more than one Sensor 214. In particular embodiments, the system includes a first Sensor 214 operatively connected to a provider system (e.g., a Partner 204) and a second Sensor configured to operate as the connection engine 224 (e.g., Holon Connect Engine) operatively connected to the cloud-based microservices system 206, wherein the role of the second Sensor includes transmitting and receiving data (member data 218) from a CDAP 208. In general, the Sensor 214 is configured to monitor the activity within the exemplary system and trigger various actions based on activity regarding patients or particular aspects of a set of information provided by the Sponsor. According to various aspects of the present disclosure, the Sensor 214 may have an operative connection to Hive 206 in order to send, retrieve, and/or transmit information regarding a trigger event, such as an accessed electronic health record. In particular embodiments, examples of trigger events may include events such as a user opening a patient's electronic medical record, a user beginning an order workflow (e.g., ordering a prescription), a user creating a new chart, a user signing an encounter note, etc. In particular embodiments, a trigger event includes intercepting an application programming interface call for reading, writing to, or retrieving a particular electronic health record, detecting manipulation of a particular electronic health record at the EHR system 226, or detecting a particular electronic health record being presented on a display. In various embodiments, detecting a particular electronic health record on a display is done so via screen scraping or another appropriate method for determining the content currently being presented on a computing system display.

Exemplary Architectural Components

Turning now to FIG. 3, an exemplary distributed architecture is shown and including therein high-level components: the Hive architecture 400, the IA architecture 500, and the Sensor architecture 600, according to one aspect of the present disclosure. In the present embodiment, these three architectural components are shown side-by-side with a firewall separating each of these. According to various aspects of the present disclosure, the components may communicate through the firewalls via HTTPS (SSL) over a suitable internet connection, or via any appropriate wired or wireless electronic communication network.

In one embodiment, the Hive architecture 400 includes components such as server clusters and NoSQL data bases for providing cloud computing power. The individual components of the Hive architecture 400 and their functionality will be described in greater detail below in the discussion of FIG. 4.

In various embodiments, the IA architecture 500 includes a plurality of processes and APIs for communicating with Hive 206 as well as the Partner 204 computing system. The individual components of the IA architecture 500 will be described in greater detail below in the discussion of FIG. 5.

In a particular embodiment, the Sensor architecture 600 includes processes and APIs for monitoring activity in EHRs as well as for executing predetermined instructions in response to trigger events (e.g., Rule Processes). The individual components of the Sensor architecture 600 will be described in greater detail below in the discussion of FIG. 6.

Turning now to FIG. 4, an exemplary architecture 400 of the cloud-based micro-services system (e.g., Hive 206 in other figures) is shown, in one embodiment. Included in the embodiment shown, are four application services clusters providing Hive API Services 402, Business Services 404, Domain Services 406, and Management Services 408. In one embodiment, the Hive API Services 402 provides the exemplary functionality to allow for external applications such as Insights Application 210, and Sensor 214 applications to authenticate, interact and exchange data with Hive 206 as these services utilize the different Business Services 404 to perform an operation.

In one embodiment, the Business Services 404 provides the exemplary functionality to allow for Hive 206 to orchestrate a number of Domain Services 406 to perform a common task and to aggregate information from a number of common services.

In various embodiments, the Domain Services 406 provides the exemplary functionality for Hive 206 to apply business rules and other logic, and handle persistence of business data such as organizations, patients, clinical events, patient contexts, users, computers, and other devices.

In a particular embodiment, the Management Services 408 provides the exemplary functionality to allow for monitoring, configuring, load balancing and managing the API Services 402, Business Services 404 and the Domain Services 406. In various embodiments, and mentioned previously in the discussion of FIG. 4, the firewall 414 protects Hive architecture 400 from unsafe network traffic and may only allow secure HTTPS (SSL) communications from trusted sources (e.g., the Sensor and the IA) through the firewall 414.

Continuing with FIG. 4 and also included in the present embodiment is a NoSQL database cluster including a NoSQL Graph Database 410 and a NoSQL Key-Value Database 412. In one embodiment, the NoSQL Graph Database 410 is a database that uses nodes and edges to store and connect data within the database. Nodes can generally be thought of as telephone poles, and the wires connecting each telephone pole can be thought of as edges. In various embodiments, a node is an individual part of a larger data structure. According to aspects of the present disclosure, a Sponsor's patient record may be stored at one node and a Partner's patient record may be stored at another node. In one embodiment, edges connect nodes and represent relationships between nodes. According to aspects of the present disclosure, nodes including information such as a Sponsor patient record and a Partner patient record may include edges to a node corresponding to the Hive reconciled identifier for the two patient records.

In a particular embodiment, implementing a graphical non-relational database (e.g., NoSQL Graph Database 410) allows for faster queries as well as the ability to store hierarchical data structures more efficiently. According to aspects of the present disclosure, the choice of NoSQL graphical non-relational databases may be more efficient than standard relational databases because it incorporates the needed data types and complex relationships, allows for scaling, and is not limited by explicit and structured mechanisms regarding how the data should be managed. However, the present systems are not limited to NoSQL graphical non-relational databases, and other types of databases such as key-value, document-based, column-based, etc., may be used.

In one embodiment, the NoSQL Key-Value Database 412 stores information as database tables, which are collections of individual items. In a particular embodiment, each item is a collection of data attributes and each attribute is stored as a key-value pair. Continuing with this embodiment, the items are analogous to rows in a spreadsheet, and the attributes are analogous to columns in a spreadsheet. Each item, in this embodiment, is uniquely identified by a primary key, which includes its first two attributes, called the hash and range. In various embodiments, a table stores data as collections of records, where each of the record stores its data in a group of key-value attribute pairs. According to aspects of the present disclosure, a patient's care gap record may be stored as an item in a table with each attribute of a care gap record searchable by its name. In one embodiment, NoSQL Key-Value databases may be more efficient than other databases because of the type of data is flat in structure and not hierarchical or relational in nature. In at least one embodiment, the Hive architectural components such as the Domain Services 406 provides efficient indexing mechanisms for faster queries and direct data fetches based upon attribute keys.

Continuing with FIG. 4, protecting the Hive architecture 400 from insecure networks is a firewall 414. In certain embodiments, this firewall 414 may be provided by a third party security service or may be proprietary software configured within the Hive architecture 400. In general, firewalls are designed to block unauthorized access into a particular system while permitting outward communication. In the present embodiment, the Hive API Services 402 shares a bi-directional communication link between both the firewall 414 and the Business Services 404. The Business Services 404 further shares a bi-directional communication link with the Domain Services 406. As shown in the present embodiment, the Domain Services 406 further shares a bi-directional link with both the NoSQL Graph Database 410 and the NoSQL Key-Value Database 412. According to various aspects of the present disclosure, an authentication request from a Sensor or IA may only need to interact with the services provided by the Hive API Services 402. According to other aspects of the present disclosure, persisting new information involves storing the data in the Hive architecture 400. In this scenario, the data may need to be transmitted from the Hive API Services 402 through the Business Services 404 and Domain Services 406 to the NoSQL Graph Database 410 and NoSQL Key-Value Database 412.

Looking now at FIG. 5, an exemplary architecture 500 of an Insights Application (IA) is shown. In one embodiment, the exemplary architecture 500 of the IA includes nine components, namely an Application Renderer 502, a Security Management Process 504, a Print Capture Receiver Process 506, a Content Surfacing Process 508, a Local Cache Process 510, a Main Process 512, Local Systems Drivers and Processes 514, a Licensing/Software Update Process 516, and a Hive API Connectivity Process 518. In various embodiments, the Hive API Connectivity Process 518 communicates with Hive to transmit and receive data through the firewall 520 by means of SSL or HTTPS communications. In various embodiments, the Licensing/Software Update Process 516 manages the commercial software license granted by Holon (or another suitable entity) and orchestrates automatic software updates to the Insights Application communicating via the Hive API Services 402 (not shown).

In various embodiments, the Local Systems Drivers and Processes 514 manage native computer operating system interactions to run Insights Application as a local service and translates the interactions from the Main Process 512 down to the local environment to render the application user interactive screens and alerts in an operating system native format. In various embodiments, the Main Process 512 serves as the process that is registered with the operating system of a local computing device, provides the runtime environment for the Insights Application, and is a manager of the other processes to perform specific tasks.

Continuing with FIG. 5, in various embodiments, the Local Cache Process 510 allows the Insights Application to cache user information such as images, user preferences, etc. used in various stages of the application workflow to provide the users with alerts, application behavior and interaction patterns. In a particular embodiment, the Content Surfacing Process 508 allows the Insights Application to display information received from Hive or other systems relevant to the current user session and context in the form of alerts, work-lists, etc.

In various embodiments, the Print Capture Receiver Process 506 allows the Insights Application to capture print streams and trigger different workflows when the application install is paired with a specific printer as further described herein (e.g., a local or remote physical printer or electronic file destination). According to various aspects of the present disclosure, the Print Capture Receiver Process 506 allows for the data being presented via the IA, data being monitored by the Sensor, clinical summaries from user interaction with electronic health records, data received from Hive, etc., to be packaged and generated as various file formats to be transmitted to third-party systems such as a Sponsor organization or another partnering healthcare clinic. According to various aspects of the present disclosure, the Print Capture Receiver Process 506 not only transmits particular data to a designated printer or electronic file location, but also may allow for various tasks to be automated, such as transmitting prescription requests to a pharmacy in response to a medical professional administering care associated with the need for a particular prescription medicine.

In one embodiment, the Security Management Process 504 allows the Insights Application to identify the application installation with Hive, authenticate users with Hive, manage user permissions and roles, manage user sessions, and securely exchange data via the Hive API Connectivity Process 518. In certain embodiments, the Application Renderer 502 is responsible for displaying the user interface elements of the Insights Application natively for the user's operating system, interpolates alert content served through the Content Surfacing Process, and manages user interactions for data inputs and displays.

In one embodiment, FIG. 6 is an exemplary architecture 600 of a Sensor. In various embodiments, the Sensor is a software configuration of the Holon Connect Engine and is installed on a server. The Sensor includes multiple elements such as an Administration Dashboard 602, Sensor Application(s) and Channels 604, a Main Process 606, a Systems Integration Service 608, Utility Services 610, Rules Processes 612, a Licensing/Software Update Process 616, a Hive API Connectivity Process 614, and a firewall 618. In certain embodiments, the Systems Integration Service 608 allows for the Sensor to transmit and receive data to and from the EHR 226. According to aspects of the present disclosure, the Hive API Connectivity Process 614 allows for outbound SSL (HTTPS) communications to be transmitted to and through the firewall 618.

Exemplary Sequence Diagrams—System Processes

Turning now to FIGS. 7-11, and according to various aspects of the present disclosure, sequence diagrams illustrating exemplary processes of the disclosed system are shown. In one embodiment, FIG. 7 illustrates an exemplary data provisioning process. In various embodiments, the process starts when a data publisher (Sponsor 202), publishes a member list/member data (as shown in FIG. 2 as Member Data 218) to the CDAP 208 (Step 1). In one embodiment, the CDAP 208 is an addressable location in computer memory on a server within the publisher's computing system. In some embodiments, the CDAP 208 is an addressable location in computer memory on a server within CollaborNet. One data publisher may be an insurance company, and the data published may be a list of all members enrolled in a health insurance plan. It should be understood from the discussion herein that the member list/member data may include information such as name, age, prescription history, surgical records, Medicare ID, or any other relevant information.

In various embodiments, the member list is updated and republished every 30 days (or any suitable timeframe such as every day, every 7 days, every 60 days, etc.). In certain embodiments, at the beginning of the 30-day period, a data publication engine (also referred to herein as the Holon Connect Engine 224) polls and pulls the data (member list) as published by the data publisher (Step 2). In one embodiment, polling and pulling the member list/member data includes requesting to download or copy the member list/member data from the CDAP 208. In certain embodiments, the data publication engine may be granted access to the published member data based on certain Hive identifiers associated with the data publication engine 224.

In one embodiment, after the data publication engine 224 accesses the member data from the CDAP 208, the member data is then parsed and evaluated (Step 3). In various embodiments, parsing and evaluating the member data includes filtering the member data, extracting relevant information, and determining the data that is relevant to the system. For example, the data publication engine 224 may parse the member data and determine that the current information being evaluated is member names and corresponding Sponsor 202 member identifiers.

In one embodiment, formatting the member data involves flattening, or normalizing the data pulled from the CDAP 208 (Step 4). In certain embodiments, the member data is formatted in order to be stored in a database. In some embodiments, the data pulled from the CDAP 208 is not in an appropriate format to be processed in the exemplary system (e.g., Hive 206). The parsing, evaluating, and formatting of data may involve filtering out or flagging certain data points, performing calculations, or rearranging the data into a format that is more efficient and scalable.

Once the steps above are executed, the data publication engine 224 may request to authenticate an electronic communication session with Hive 206. In various embodiments, the authentication request from the data publication engine 224 to Hive 206 may be initiated using certain APIs. In one embodiment, using the Hive API Connectivity Process 614 (as shown in FIG. 6) within the data publication engine 224, authentication with Hive 206 may be requested over HTTPS communications (Step 5). In one embodiment, Hive 206 receives the request for authentication using the services within the Hive API Services 402 (as shown in FIG. 4). It should be understood from the discussion herein that the data publication engine 224, as well as Hive 206, may be included in CollaborNet described above.

In one embodiment, a new electronic communication session between Hive 206 and the data publication engine 224 is granted if the Hive API Services server cluster 402 (discussed above) authenticates the request sent by the data publication engine 224 (Step 6). Once an electronic communication session between the data publication engine 224 and Hive 206 has been established, the data publication engine 224 may package and secure the formatted data from the previous steps (Step 7). In various embodiments, packaging and securing the data involves encrypting the data, or performing some other form of preparatory action before the next step in the process, which involves posting the data to Hive 206.

In one embodiment, posting the data to Hive 206 involves transmitting the packaged and secured data over a public network (Step 8). In various embodiments, outbound HTTPS communications are used in order to transmit the packaged and encrypted data. Once the data has been transmitted to Hive 206, in particular embodiments, the data is unpackaged (which may include, for example, decrypting the data). In certain embodiments, the unpackaged data and relationships between certain aspects of the data are persisted in Hive 206 and stored (Step 9).

According to aspects of the present disclosure, after thirty days (or any other appropriate amount of time), another updated set of member data may be published by a data publisher to the CDAP 208 (Step 10). It should be understood from the discussion herein, that once updated member data is published to the CDAP 208, the data publication engine 224 may poll and pull the data, and the process described above may repeat (Step 11).

Looking not at FIG. 8, the present embodiment illustrates the organization and user provisioning process, according to one embodiment. In various embodiments, organizations and users of the present system may include healthcare organizations, such as hospitals or health clinics, private medical practices, and medical professionals that work at these establishments. Typically, these users of the system access electronic health records in order to complete daily work tasks. The present embodiment outlines the process involved with establishing these organizations and certain users in the CollaborNet system.

In one embodiment, the IA 210, once launched (Step 1), allows for the creation of a new organization as a Sponsor 202. In various embodiments, and prior to creating a new organization as a Sponsor 202, the IA 210 may call the Hive API Service 402 to authenticate the IA 210 user (Step 2), and Hive 206 may grant authenticate and grant the access session (Step 3). In this embodiment, a user may authenticate as a super-administrative user. In various embodiments, creating a Sponsor 202 organization within the IA 210 allows for Hive 206 to associate certain member list and member data with a certain Sponsor 202. In certain embodiments, once a Sponsor 202 is created within the IA 210 (Step 4), the information regarding the new Sponsor 202 may be transmitted to, and stored in, Hive 206. In one embodiment, transmitting the information regarding the new Sponsor 202 to Hive 206 allows for Hive 206 to maintain a record of the activity associated with the new Sponsor 202.

According to aspects of the present disclosure, once the IA 210 saves the new Sponsor 202 information to Hive 206 (Step 5), Hive 206 persists the new Sponsor 202 details within Hive 206 and also associates it with a newly-generated Sponsor Hive ID in order to uniquely identify that Sponsor 202 from all other present and future Sponsors 202 (Step 6). In various embodiments, once a Sponsor 202 is created, a substantially similar process as described above may be followed to create a new user within the Sponsor 202. In one embodiment, a new user associated with the Sponsor 202 may be created within the IA 210 and associated with a newly-generated user Hive ID in order to uniquely identify that user from all other present and future users (Step 7). According to aspects of the present disclosure, once the new user is created within the Sponsor 202, the information associated with the new user may be saved and persisted with Hive 206 (Steps 8 and 9). In certain embodiments, persisting a new user with the user's Hive ID may include allowing the new user to be tracked, identified, and managed within Hive 206.

In one embodiment, a user defined within that Sponsor 260 may create one or more Partners 204 within that Sponsor 202. In one embodiment, a Partner 204 created within a Sponsor 202 is assigned a newly-generated Partner Hive ID in order to uniquely identify that Partner 204 from all other present and future Partners 204, regardless of Sponsor 202 (Step 10). According to aspects of the present disclosure, once the new Partner 204 is created within the Sponsor 202, the information associated with the new Partner 204 may be saved and persisted with Hive 206 (Steps 11 and 12).

In various embodiments, there may be a first administrative user for a Partner 204 created by a Sponsor 202 user. That first administrative user may then create additional users, both other administrative and general users, as necessary for that particular Partner. In substantially similar processes to creating Sponsor 202 users, Partner 204 users are created in IA 210, and persisted in Hive 206, with each user assigned a newly-generated Hive user ID.

According to aspects of the present disclosure, if the Partner administrative user is authenticated by Hive 206, then a new access session may be granted between Hive 206 and the IA 210. Once an administrative user is authenticated, a new user may be created for the Partner 204 to which the presently authenticated administrative user belongs. In this embodiment, all users created are automatically defined in Hive 206 as users belonging to the Partner 204 under which they were created.

Once a new Partner 204 user is persisted with user's Hive ID, the process may continue to associate the EHR's 226 proprietary user ID to the Partner 204 user's Hive ID. In one embodiment, associating the EHR's 226 proprietary user ID to the user's Hive ID through the IA 210 may allow for the CollaborNet system to match the IDs across the various contributing elements of the system.

Turning now to FIG. 9, a sequence diagram illustrating the membership attestation and cross-system identity matching process is illustrated, according to a particular embodiment. In one embodiment, this process includes the communication between Hive 206, the Sensor 214, and an EHR 226. In the present embodiment, the process begins at the Sensor 214 by configuring the Sensor 214 with a Hive Partner ID so that a relationship between an instance of the Sensor 214 and a specific Partner 204 may be identified (Step 1).

In one embodiment, once the Sensor 214 is configured, the Sensor 214 may use appropriate API function calls to authenticate an electronic communication session with Hive 206. In various embodiments, the Sensor 214 may use the Hive API Connectivity Process 614 to send outbound HTTPS communications to Hive 206 (Step 2). In one embodiment, Hive's API Services server cluster 402 will receive the API authentication request from the Sensor 214 and grant an electronic communication session (Step 3). If the electronic communication session is granted by Hive 206, the session may continue to allow the Sensor 214 and Hive 206 to receive and transmit data as necessary. According to aspects of the present disclosure, the session between Hive 206 and the Sensor 214 may allow for the Sensor 214 to pull Sponsor member data 218 (shown in FIG. 2) from Hive 206 for that particular Sponsor 202 within which the Partner 204 was created (Step 4).

In one embodiment, once the session between Hive 206 and Sensor 214 is established, the Sensor 214 may request to open an electronic communication session to the EHR 226 (Step 5). In certain embodiments, the EHR 226 may grant access to the Sensor 214 if the sensor is authenticated (Step 6). In various embodiments, granting access from the EHR 226 to the Sensor 214 may allow for the Sensor 214 to receive and analyze data from the EHR 226. In various embodiments, patient information included in the EHR 226 may be queried by the Sensor 214 and be evaluated using certain processes as configured within the Sensor 214. In various embodiments, the patients included in the EHR 226 may be correlated to a Sponsor's 202 member Hive ID by means of a matching process using the Sponsor's 202 member data 218 and the EHR's 226 patient data (Step 7).

Continuing with the present embodiment, the Sensor 214 may then update the Sponsor 202's members stored within Hive 206 with the new information regarding the patients accessed in the EHR 226 (Step 8). In certain embodiments, upon receiving this information, Hive 206 may persist the Sponsor's 202 members with the new information retrieved from the EHR 226 (Step 9).

Turning now to FIG. 10, in one embodiment, a sequence diagram illustrating the EHR context control process is shown. In one embodiment, the EHR control process begins when the Sensor 214 opens an electronic communication session to monitor EHR 226 events (Step 1). In various embodiments, and as will be discussed below, EHR 226 events may include a medical professional opening a patient's electronic health record. In this scenario, opening an electronic communication session to the EHR 226 may allow the Sensor 214 to recognize this event and respond accordingly.

In one embodiment, the EHR 226 may grant access to the Sensor 214, which may then make certain API calls in order to authenticate access with Hive 206 (Steps 2 and 3). According to various aspects of the present disclosure, the API authentication between the Sensor 214 and Hive 206 is coordinated by the Hive API Connectivity Process 614 within the Sensor 214 and the Hive API Services server cluster 402 within Hive 206. In certain embodiments, the API authentication calls are communicated between Hive 206 and the context server (e.g., Hive 206) as HTTPS communications. Further, and in various embodiments, once the access to a new session is granted between Hive 206 and the Sensor 214 (Step 4), the Sensor 214 may wait until an appropriate triggering event occurs in the EHR 226 to communicate any data to Hive 206.

In one embodiment, the Sensor 214 is configured to establish an electronic communication session the EHR 226 in order to query for patient context or other information every three seconds (or any appropriate amount of time). In one embodiment, at Step 5, an application login event may occur where a user at the Partner 204 may enter his/her credentials (e.g., user name and password, token, etc.) for accessing the electronic health records at EHR 226. In response to the user at the Partner 204 entering his/her identity credentials, the credentials, or an identifier corresponding to the credentials, may be transmitted to Hive 206 by the Sensor 214 for generating a session between the Hive 206 and Sensor 214 for transmitting information relating to trigger events (Steps 6 and 7). In various embodiments, in response to the Sensor 214 transmitting the Partner 204 credentials to Hive 206, the Sensor 214 monitors the EHR system 226 at various intervals for a trigger event (Step 8). According to various aspects of the present disclosure, the Sensor 214 may monitor for trigger events by directly accessing the EHR system 226 and detecting manipulation or access to a particular electronic health record, screen scraping electronic records from a computing system display at the Partner 204, or by intercepting API calls to the EHR system 226 for particular electronic health records associated with particular patients.

In response to a user at the Partner 204 accessing a particular electronic health record (Step 9), the Sensor 214 recognizes this action as a trigger event (Step 10), and the Sensor 214 further transmits healthcare information, a patient identifier, and an identifier relating to the user accessing the electronic health record, to Hive 206 to be persisted (Steps 11 and 12). According to aspects of the present disclosure, the Sensor 214 may continue to query the EHR 226 for patient context or other information after a trigger event is detected. In some embodiments, persisting this information to Hive 206 may allow for the transmitted healthcare information to be easily associated and connected with other relevant events, triggers, and context.

Turning now to FIG. 11, a sequence diagram illustrating the exemplary context sensitive alert and detail data presentation process is shown, according to one embodiment. In the present embodiment, the exemplary process begins when the IA 210 is launched (Step 1). In various embodiments, the IA 210 is launched by clicking an icon on the screen of the computing system, running a script in a command line, or other various methods of launching a software application. According to various aspects of the present disclosure, when the IA 210 is launched, the IA 210 may make various API calls to authenticate the user launching the IA 210 (Step 2). n one embodiment, the IA 210 uses the Hive API Connectivity Process 518 to send HTTPS communications to Hive 206. Hive 206 may then receive those HTTPS communications at the Hive API Services server cluster 402.

In various embodiments, the IA 210 user launching the application may be authenticated by Hive 206 (e.g., by user name and password, a token, or similar credentials), which may in return result in the IA 210 polling the context service regarding the authenticated IA 210 user periodically for a predetermined amount of time (Steps 3 and 4). In one embodiment, the IA 210 may poll the context service regarding the authenticated IA 210 user every 3 seconds in order to have access to consistently updated data. However, it should be noted that the IA 210 may poll the context service at different rates. In various embodiments, the IA polls Hive 206 periodically in response to a trigger event, such as the trigger event described above in the discussion of FIG. 10. In response to a Sensor 214 detecting an accessed electronic health record and transmitting healthcare information and identifiers relating to the particular patient and the user at the Partner 204, the IA 210 is configured to receive matching or corresponding healthcare information from the Hive 206 (Step 5).

In one embodiment, Hive 206 may transmit the current patient context and applicable Sponsor 202 published member data 218 to the IA 210, and the IA 210 may be configured to present the information to the IA 210 user as a summary of the Sponsor's 202 published member data 218. It should be understood from the discussion herein that this information may be presented to the user of the IA 210 in the form of an alert. In a particular embodiment, the information received at the IA 210 from Hive 206 may be healthcare gap information (e.g., information other than what is stored locally) and the healthcare gap information may be presented to the user at IA 210 as pop-up notification or bubble (Step 6).

According to various aspects of the present disclosure, the user of the IA 210 may select the alert (Step 7) displayed on a computing device. According to various aspects of the present disclosure, and in response to selecting the bubble, additional information relating to the notification, but not included in the initial bubble, may "slide-out" from behind the boundaries of the display. In one embodiment, the process of selecting the alert may include clicking on the alert with a computer mouse, touching the alert on a touch screen, or another appropriate way to select available information within a computing system.

In one embodiment, selecting the alert presented to the user of the IA 210 may result in the IA 210 presenting a fixed sized insights data detail panel, opening sized to approximately 25% of the screen width, and 100% of the screen height. In one embodiment, the detail panel may be presented from the right side of a screen and the detail panel may include the Sponsor 202 published member insights detail data as summarized in the previous alert (e.g., healthcare gap data). In other embodiments, the IA 210 may open by means of launching a new full sized window or a new application (Step 8).

Exemplary Code Gap Detection

Turning now to FIG. 12, an exemplary flowchart illustrating the exemplary code gap detection process 1200 is shown, according to one embodiment of the present disclosure. In various embodiments, the process begins at step 1202, where the cloud-based micro-services system 206 receives health record data from the Sensor 214 in response to a trigger event. According to various aspects of the present disclosure, the trigger event may be a doctor at a Partner 204 organization opening an electronic health record of a particular patient. In a particular embodiment, the Sensor 214 is configured to monitor activity, such as reading and writing to the EHR 226, at the Partner 204 organization computer system. In certain embodiments, the Sensor 214 may intercept application programming interface calls to the EHR 226 for retrieving an electronic health record associated with a particular patient. In some embodiments, the Sensor 214 may detect an electronic health record associated with a particular patient being presented on the display of the Partner 204 organization computing system via screen scraping or a similar method. According to certain embodiments, if the Sensor 214 detects that a particular patient's electronic health record is currently opened, surfaced on the screen of the doctors computing system, or any other suitable method of accessing the record, the sensor may transmit at least a portion of the electronic health record, as well as an identifier associated with the patient in focus, to the cloud-based micro-services system 206.

At step 1204, and in response to receiving the at least portion of the electronic health record and the corresponding patient identifier, the cloud-based micro-services system 206 retrieves one or more matching health records from internal databases. In one embodiment, the one or more matching health records are health records associated with the particular patient, but not necessarily associated with the Provider 204 that accessed a patient health record at step 1202. In various embodiments, the one or more matching health records may have originated from a separate Partner that the patient has previously visited, or the one or more matching health records may have been provided by a Sponsor.

At step 1206, the system compares the received health record data and the one or more matching health records to determine gaps in coding. According to various aspects of the present disclosure, the code gaps are identified by cross referencing the data from the received health record data and the one or more matching health records. In one embodiment, inconsistencies between the two sets of data will generally be determined as a gap. As will be shown and described below when referencing FIG. 13, gaps in coding are exposed when two sets of patient data that should be consistent include contradicting, missing, or generally inconsistent data.

At step 1208, and according to one embodiment, the system stores the determined healthcare code gap data in a context table, shown and described in greater detail below in the discussion of FIG. 13. According to various aspects of the present disclosure, the context table is a database accessible to the IA, and storing the healthcare code gap information in this particular location allows for a Partner 204 to access gap information at the point and time of care via the IA.

At step 1210, the system determines if the stored records in context table expose gap information relating the particular patient's electronic health record in focus. If no gaps were detected, the process may terminate. In one embodiment, if the context table does include gap information relating to the particular patient's electronic health record, the cloud-based micro services system 206 may transmit the gap information to the IA to be presented on the display of the computing system at the Partner 204 in the form of an alert (step 1212). In various embodiments, the alert is a pop-up or slide-out feature that generally remains "out-of-sight" or mostly hidden until an alert is surfaced. In particular embodiments, examples of the exemplary alert appearance generated by the IA are shown in FIG. 24 below, according to one embodiment.

Exemplary Context Table Data Structure

Looking now at FIG. 13, an exemplary electronic health record data structure and context table (also referred to herein as context service) are shown, according to one embodiment. In various embodiments, an electronic health record at a Partner 204 organization may include information such as, but not limited to, date of care, the coding format used at the Partner 204 organization, particular codes corresponding to administered care, patient name, patient date of birth, insurance information, etc. In the present embodiment, exemplary electronic health records (or at least portions of electronic health records) corresponding to a particular patient are shown including a date, coding format, and particular code corresponding to administered care. The chart 1302, corresponding to a "Partner 1 EHR" includes two instances of care provided to the particular patient, these instances including treatment for high blood pressure (Code: 796.2) on Oct. 6, 2017, and well as treatment for diabetes (Code: 250.00) on Oct. 27, 2017. In various embodiments, Hive 206 may compare the chart 1302 to a chart 1304 corresponding to a "Partner 2 EHR." According to various aspects of the present disclosure, both the Partner 1 EHR and the Partner 2 EHR may have treated the particular patient at some point in time, and both include separate records corresponding to the past treatment. The chart 1304 includes only one instance of care provided to the particular patient, this care being treatment for diabetes (Code: 250.40) on Oct. 27, 2017. In a particular embodiment, Hive 206 may compare each entry in the respective health records to identify inconsistencies or "gaps" in the data. According to various aspects of the present disclosure, the detected gaps are stored in a context table 1306 within Hive 206. In some embodiments, when queried IAs for health record data corresponding to particular patients, Hive 206 may transmit the gap data from the context table 1306 to the requesting system, where the gap data may further be presented onto a display in the form of a contextual alert, as shown and described below in FIG. 24.

Exemplary Paired System(s) Identity Management

Turning now to FIG. 14, an exemplary external paired system(s) identity management overview and environment is shown, according to one embodiment. In the present embodiment, two organizations labeled Sponsor 202 and Partner 204 are shown. In various embodiments, each organization includes a system, such as a computing system, and in the case of the Partner 204, a user of the system. According to various aspects of the present disclosure and for the sake of example, the Partner 204 user, John Doe, signs into both the Insights Application 210 and the EHR 226. In certain embodiments, the sign-in process may occur automatically on computer system startup or may include signing into the IA 210 using the features of the IA 210 as shown in FIGS. 22 and 23. In particular embodiments, the EHR 226 is operatively connected to the Sensor 214. It should be understood from the discussion herein that, in particular embodiments, the Sensor 214 and the IA 210 are configured to operate asynchronously but in conjunction with each other as communications with Hive 206 occur. In one embodiment, the Sensor 214 monitors for activity regarding particular patient charts accessed from the EHR 226 by the user John Doe, and if a certain patient chart is opened (e.g. chart ID: pid123), the Sensor 214 may submit at least a portion of this information to Hive 206. Further, and on an interval basis, the IA 210 may execute the Hive API Connectivity Process 518 (as shown in FIG. 5) to query Hive 206 for information regarding the particular user signed into the IA 210 and any corresponding patient context currently open in the EHR 226 by the user (as referenced by a paired system identifier to be discussed later herein). In various embodiments, the information regarding the patient in context is then transmitted from Hive 206 to the IA 210. In general, while asynchronous connections are being made to Hive 206, the IA 210 and the Sensor 214 operate simultaneously and the activity monitored by the Sensor 214 may determine the information transmitted to the IA 210 by Hive 206.

Continuing with FIG. 14, in various embodiments, the relationships of disparate identities (of patients, users, providers, etc.) within the data held in Hive 206 and the Sponsor 202 and Partner 204 organizations are achieved via mapping of various identifiers. Examples of the identifiers and associated mapping concepts corresponding to the present embodiment are listed below.

Partner—Person Identifiers (doctor "John Doe" and patient "Jane Smith")

Doctor John Doe's National Provider Identifier is "NPI: abcdef"

In various embodiments, the NPI associated with doctor John Doe is his National Provider Identifier. This identification number may be associated with John Doe anywhere within the U.S. as long as he is a practicing medical professional regardless of his place of work. Typically, the NPI is not created by the EHR 226, but is typically stored within the configuration of the EHR 226.

Doctor John Doe's Paired System identifier at Partner is "paired ID: 6789"

In various embodiments, a paired system ID is the concept of linking a user account within the IA 210 to a user ID assigned and managed by the third party system (e.g. the EHR system 226 where the Sensor 214 is monitoring for activity) and is fundamentally a bridging mechanism to relate a single user defined in multiple disparate systems to actions for trigger events. In this example, the paired system ID is an identification number that associates doctor John Doe as a user of the third party system (e.g. EHR 226) of the Partner 204 with the currently signed-in user of the IA 210 known as "jdoe@org4.net". In particular embodiments, associating data with one identification number rather than two individual identification numbers may enable the system to efficiently conduct various look-ups and/or other tasks. For example, if a user signs into the EHR 226 of the Partner 204 and the database of the EHR 226 stores "system user: 6789 has signed in and has opened chart: pid123", then the Sensor 214 may relay the currently signed in user to Hive 206 where a match between user: 6789 will be made to IA 210 user jdoe@org4.net.

Patient Jane Smith's Chart Identifier at Partner is "chart ID: pid123"

This identification number may be a system assigned patient's chart ID, and represents Jane Smith within the EHR system 226 of the Partner 204. In various embodiments, Jane Smith's electronic health record is assigned this chart identification number upon chart creation within the EHR 226 at the Partner 204.

Hive—Person Identifiers (doctor "John Doe" and Patient "Jane Smith")

Doctor John Doe's Hive identifier is "Hive ID: 4589214"

In various embodiments, this Hive ID is a Hive-generated identification number associated with doctor John Doe. In particular embodiments, the system associates any additional linked identifiers or activity involving John Doe between Sponsors and any associated Partners across CollaborNet.

Patient Jane Smith's Hive Identifier is "Hive ID: 56781243"

In various embodiments, the Hive ID for Jane Smith is a Hive-generated identification number associated with Jane Smith universally within Hive 206. In various embodiments, Hive 206 may use this identifier to associate any additional linked identifiers or activity involving Jane Smith between the Sponsor 202 and any associated Partners (e.g., Partner 204).

In one embodiment, the Sponsor 202 submits member data 218 to Hive 206 on an interval basis. Continuing with this embodiment, included within the member data 218 may be information relating to a person named Jane Smith. In various embodiments, the Sponsor 202 may assign a member identification number to this person, such as a Medicare ID (e.g. 79a3bc5), along with a person identifier of Jane's primary care provider, John Doe. In the present embodiment, a National Provider Identifier, known as an NPI, identifies the primary care provider John Doe as "NPI: abcdef".

In one embodiment, Jane Smith visits the Partner location 204 (e.g., a family health clinic) in need of medical attention. Her doctor, John Doe, is associated with the Partner location 204 and may have an EHR user identification number of "6789" that identifies him within the Partner 204 EHR system 226. In various embodiments, John Doe will also sign in to the CollaborNet network and system through the Insights Application 210 using his user name "jdoe@partner.org". In particular embodiments, once John Doe signs in to the EHR 226 with his user ID 6789, his profile, previously configured with an external paired system ID as described above, will associate the Hive 206 user ID "jdoe@partner.org" to the EHR user 6789 and establish a session between the IA 210 and Hive 206 that may allow John Doe to receive additional information regarding Jane Smith that is not included in her electronic medical record, as described herein.

According to aspects of the present disclosure, the Sensor 214 deployed to the Partner 204 is configured to monitor user activity within the EHR 226. For example, if John Doe, user: 6789, opens the patient chart associated with Jane Smith, chart: pid123, the action of opening the chart may trigger the Sensor 214 to send the context of "chart: pid123 opened by user: 6789" (attributing patient Jane Smith's chart opening to user John Doe) to Hive 206.

In one embodiment, the IA 210 queries Hive 206 every few seconds (or any suitable amount of time) for patient context associated to the currently authenticated user jdoe@partner.org, corresponding to external paired system id 6789. In particular embodiments, given Hive 206 has already stored a patient context (e.g. chart: pid123) for IA 210 user jdoe@partner.org (external paired system id of 6789) to the database, upon receiving the query from the IA 210, the clinical content originally sourced from the Sponsor 202 to Hive 206 (e.g. clinical gaps in care, etc.) is sent to the IA 210 and further surfaced within the workflow of the third party EHR system 226 of John Doe.

External Paired System(s) Identity Management—Flowchart

FIG. 15 is a flowchart illustrating the exemplary external paired system(s) identity management process 1500, according to various aspects of the present disclosure. In various embodiments, this exemplary process corresponds to the external paired system(s) identity management overview, shown in FIG. 14 and described immediately above, and references the components as shown in FIG. 2.

In one embodiment, the process 1500 begins at step 1502, which includes membership data 218 from the Sponsor 202 being retrieved from a Common Data Access Point 208 by the Holon Connect Engine 224 (a component of Hive 206). As discussed throughout the present disclosure, membership data 218 may include information corresponding to individuals enrolled in certain Sponsor 202 organizations (e.g., insurance providers). In various embodiments, the membership data 218 may include a list of Medicare beneficiaries (e.g., "member list"). In some embodiments, a member list 218 may include relevant information such as name, gender, date of birth, age, Medicare beneficiary identification, primary care provider information, gaps in clinical care, gaps in claims submission and coding, MSSP/MSO/ACO identifiers, etc. relating to the particular patients included in the member list.

Proceeding to step 1504, Hive 206 associates all members included in the membership data 218 with Hive 206 identification numbers. For example, and described above in the discussion of FIG. 14, a patient Jane Smith is assigned a Hive 206 identification number of "56781243" that will allow for her health related activity to be tracked across Hive 206 as well as various third-party systems that communicate with Hive 206.

At step 1506, the Sensor 214 at the Partner 204 submits patient contexts 216, including at least a portion of an electronic health record, a patient identifier, and a Partner identifier, to Hive 206, according to one embodiment. Furthermore, at step 1508, Hive 206 reconciles and associates external system identifiers from the Partner 204 with internal Hive IDs, according to various embodiments. Proceeding to step 1510, in various embodiments, users are provisioned in the IA 210 and are paired with third-party system identifiers from within the IA 210 user profile. According to various aspects of the present disclosure, submitting patient contexts 216 (e.g., chart data) to Hive 206, and further associating IA 210 users with third-party system identifiers allows for Hive 206 to monitor electronic health record activity associated with the submitted patient contexts 216, and to further allow the IA 210 users to be alerted about the activity. According to various aspects of the present disclosure, the Hive 206 may receive patient data from the Sensor 214 in various scenarios. For example, the Sensor 214, in response to direct connection to an EHR 226 and detecting electronic access to a particular electronic health record, may transmit patient data to Hive 206. In another example, the Sensor 214 may periodically transmit patient data to the Hive 206 via monitoring EHR 226 activities not related to accessing a particular electronic health record.

At step 1512, and according to one embodiment, the user at the Partner 204 organization may open an electronic health record (e.g. patient chart). In various embodiments, opening an electronic health record may include displaying the electronic health record on the screen of a computing device, adding or amending data included in the record, etc. Proceeding to step 1514, and in response to accessing an electronic health record, the Sensor 214 senses particular patient context (e.g., data corresponding to a patient included in the member list 218) and sends a chart open event to Hive 206 with external system user IDs (e.g. external paired system IDs), according to one embodiment. According to various aspects of the present disclosure, the Sensor 214 is configured to monitor activity corresponding to particular patients at an EHR system 226. In particular embodiments, the Sensor 214 may be configured to monitor for trigger events such as opening electronic health records, augmenting electronic health records, submitting or reporting portions (if not all) of electronic health records, etc.

Proceeding to step 1516, in one embodiment, Hive 206 associates the chart ID and the external paired system ID with the IA 210 user at the Partner 204 location and the member from the Sponsor 202. In particular embodiments, at step 1516, Hive 206 may match the previously received patient context data 216 with the various identification numbers associated with the Sensor 214 at the Partner 204, operated by the user of the IA 210, in response to receiving the chart open event (e.g. trigger event) at step 1514.

In various embodiments, at step 1518, the IA 210 queries Hive 206 for currently authenticated user events and contexts. In particular embodiments, at step 1518, Hive 206 may include clinical data from other third-party systems relating to the electronic health record of the particular patient being accessed at the Partner 204 location. According to various aspects of the present disclosure, querying Hive 206 for currently authenticated user events and contexts may include executing various API calls for retrieving the related clinical data. Proceeding to step 1520, Hive 206 submits or transmits patient context and additional content to IA 210 for the user at the Partner 204 organization. In various embodiments, at step 1522, the IA 210 surfaces the Sponsor 202 gap content 228 into the workflow of the third-party system at signed-in user workstation.

Follow a Patient

Turning now to FIG. 16, a diagram illustrating the process referred to herein as "follow a patient" is shown, according to one embodiment. In various embodiments, the "follow a patient" concept can be understood as the ability for multiple payer organizations and healthcare clinic organizations, depicted as "clinic" in the drawing, to share and monitor information regarding individual patients throughout a web of interconnectivity by implementing a distributed architecture and a cloud-based micro-services system 206 (e.g., Hive).

Shown in the present embodiment are two payer organizations indicated as Payer 1602A and Payer 1602B, four Clinic organizations indicated as Clinic 1604A, Clinic 1604B, Clinic 1604C, and Clinic 1604D, and three patients indicated as patient 1606A, patient 1606B, and patient 1606C. In the present embodiment, patient 1606A and patient 1606B are both included in Payer 1602A's organization (e.g. purchase insurance from the same payer/insurance provider). According to aspects of the present disclosure, patient 1606A and patient 1606B may be included in any member lists/member data made available by Payer 1602A. In certain embodiments, a patient, such as patient 1606A, may visit several different clinic organizations (e.g., physicians or health care establishments).

As shown in the present embodiment, patient 1606A is associated with two clinic organizations, Clinic 1604A and Clinic 1604C. Based on the association of patient 1606A with one payer organization and two clinic organizations, the cloud-based micro-services system 206 (e.g., Hive) may create a web of connections between each organization associated with patient 1606A. In one embodiment, if patient 1606A were to receive a routine checkup at one of the clinic organizations, the other clinic organization as well as the payer organization may receive status updates pertaining to encounter events or updates to gap closure activity provided to the network by the clinic organization via the cloud-based micro-services system 206 (based on the matching of identifiers and normalization of data as discussed herein and described in further detail immediately below).

Turning now to FIG. 17, a flowchart describing the exemplary "follow a patient" process 1700 is shown, according to one embodiment. As discussed above, the follow a patient process 1700 includes matching external identifiers, as well as general patient demographics, in order to track and correlate particular patient activities across various Partner organizations. In one embodiment, the process begins at step 1702 where the cloud-based micro-services system receives a request for health record data from a first third-party, the request including a particular patient identifier and a third-party identifier relating corresponding to the first-third party.

At step 1704, and in one embodiment, the cloud-based micro-services system matches the particular patient identifier with corresponding electronic health record data and indicates the matched data as associated with the first-third party identifier. In one embodiment, matching the particular patient identifier with corresponding health record data allows for the cloud-based micro-services system to create a "network" or "web" of third-party systems that are associated with a particular patient. In various embodiments, the cloud-based micro-services system matches the particular patient identifier with the corresponding electronic health record data similarly to the process described in the discussion of FIG. 16.

At step 1706, and as a result of matching the particular patient identifier with corresponding electronic health record data, the cloud-based micro-services system stores the particular patient identifier as associated with the corresponding health record data and the first-third party identifier. According to various aspects of the present disclosure, associating the particular patient identifier with the corresponding health record data and first-third party identifier may allow for the system to identify that additional health record data relating to the particular patient from other third-party systems may be of interest to the first-third party system.

Proceeding now to step 1708, the cloud-based micro-services system receives health record data associated with the particular patient identifier from a second third-party. According to various aspects of the present disclosure, the health record data from the second-third party may include data other than the data received from the first-third party. In a particular embodiment, the health record data received from the second-third party may be in response to a trigger event (e.g., accessing an electronica health record) at the second third-party.

At step 1710, the cloud-based micro-services system transmits the health record data received from the second third-party to the first-third party due to matching particular patient identifiers associated with the data. In one embodiment, the system may transmit at least a portion of the newly received healthcare data to the first third-party. According to various aspects of the present disclosure, the transmitted data may be presented to the first third-party as an alert informing the provider of the first third-party that there has been activity relating to the particular patient's health record data from another provider (the second third-party). This functionality allows for providers to have better information regarding their patients, allowing them to provide better care as well as various other advantages discussed herein.

Exemplary Task Automation

Turning now to FIG. 18, a flowchart illustrates the exemplary task automation process 1800, according to one embodiment. In various embodiments, the system may automate tasks such as prefilling Health Risk Assessment (HRA) forms from a payer (or any third-party form requiring chart data elements), lab order service eligibility checking, population health portal access and data searches, etc. According to various aspects of the present disclosure and as shown in FIG. 6, the Sensor 600 includes a rules processes engine 612 (e.g., Rules Processes) for determining the appropriate actions for automating particular tasks based on the detected trigger event. In a particular embodiment, the rules processes engine 612 is a software module included within the Sensor 600, and pre-configured instructions from the rules engine determine how the Sensor 600 responds to various trigger events. One example of using the rules processes engine 612 and Sensor 600 to automate tasks is to configure the system to automatically present alerts to users that may not have compatible insurance for a particular service, such as ordering a medication. In this example, the Sensor 600 is configured to monitor for new order workflows. When a new order workflow is detected, the Sensor 600 checks the patient's insurance and correlates the order and insurance with a list of items that are excluded from being covered under certain types of insurance. If a match is found, the system may automatically present an alert to the user ordering the medication explaining the orderable service will not be covered by the insurance and that an advanced beneficiary notice may need to be signed ahead of completing the order. In pre-existing systems, this process of determining appropriate insurance coverage, alerting the patient, and further notifying them of next steps may take days to effectively complete, which may be too long if the patient is on a constrained timeline for receiving the medication. The task automation process described herein presents a technical solution that effectively handles issues such as the problem described above in near real-time.

In one embodiment, the instructions for task automation processes 1800 are initially created and stored at Hive, and later pushed down to remote Sensor(s) upon command. In various embodiments, after pushing task automation instructions to the remote Sensor, the Sensor retains the instructions for that particular trigger event until an updated command is sent down from Hive to the Sensor for changing the configuration or instructions. In some embodiments, the system may include a catalog of Sensor configurations and instructions in Hive as a back-up log of all available task-automation configurations. According to various aspects of the present disclosure, maintaining this catalog acts as a failsafe and recovery measure if certain task-automation configurations are lost, and also maintaining the catalog remotely saves memory at local systems.

In particular embodiments, the task automation instructions may be configured in a multitude of ways. In one embodiment, task automation instructions are configured as IFTTT (if this than that) instructions, whereby the instruction is created in a user interface similar to the integration engine (e.g., System Integration Service 608) and creating the instruction includes describing the task requirements and storing the task requirements on the local Sensor. In other embodiments, the instructions may be updates to a browser based web extension that is monitoring web activity for API calls returning to a web front end from a remote backend hosted by a third-party vendor. In particular embodiments, task automation instructions may be configured and installed on a user's computing system as a service, rather that the user configuring the implementation. According to various aspects of the present disclosure, certain task automation instructions may be previously installed on all instances of the herein described system.

Referring now to the exemplary flowchart in FIG. 18, according to one embodiment, the exemplary task automation process begins at step 1802, when the Hive receives health record data in response to a trigger event at the Sensor. As discussed immediately above, in various embodiments, Hive may store various sets of predetermined instructions and Sensor configurations for responding to trigger events detected by the Sensor. At this step, the Sensor transmits the health record information and/or patient identification information to be matched with corresponding predetermined instructions.

At step 1804, and according to various aspects of the present disclosure, Hive matches health record and identifier with the predetermined instructions, and at step 1806, Hive transmits the predetermined instructions to the Sensor for initiating the predetermined action. In some embodiments, the predetermined instructions are stored locally at the Sensor.

Exemplary Printer Driver

Turning now to FIG. 19, an overview of a "print capture" process is illustrated, according to one aspect of the present disclosure. The print capture process, or Print Capture Receiver Process 506 as briefly discussed above in the description of FIG. 5, is a process by which a software driver is configured to package and export particular data at a Partner 204 to be transmitted to other third-party systems or the Sponsor 202. In particular embodiments, and as mentioned above, the printer capture functionality may be executed in parallel with the IA 210, or any other application running at the Partner 204 organization computing system. In certain embodiments, the particular data packaged and exported via the printer driver may include healthcare data, financial data, insurance data, etc. As will be described in greater detail immediately below, the printer driver is operable to generate multiple file formats (e.g., PDF, JPEG, TIFF, etc.) of the data being exported.

Included in the present embodiment are the Sponsor 202 and Partner 204, both operatively connected to the Hive 206. It should be understood from the discussion herein that Hive 206 is an element of CollaborNet and is a software and/or hardware configuration that creates a secure network that manages the assembly, packaging, routing, and delivery of healthcare information among and between care delivery organizations. According to one embodiment, and for the purpose of example, a user (e.g., a medical professional) at the Partner 204 organization has performed an action involving accessing and/or modifying an electronic health record. In one embodiment, after the electronic health record has been accessed and/or modified, a clinical summary, or other form of appropriate content corresponding to the activity performed is generated and the user may further select to print the content.

In various embodiments, and according to one example, the user may choose to print the clinical summary to the Sponsor 202 organization or another third-party system. In particular embodiments, the printer driver may receive the data to be transmitted from the application accessing the data (e.g., IA 210), or the printer driver may retrieve the data from a particular location in memory (e.g., EHR 226). According to various aspects of the present disclosure, the printer driver may further generate multiple files of various formats that correspond to the data to be transmitted. In certain embodiments, the printer driver may translate or map the file format of the native data to the requested or default file formats for exporting (e.g., PDF, JPEG, TIFF). According to the present embodiment, the generated files are indicated as data object 1902. In a particular embodiment, the IA 210 first transmits the data object 1902 to Hive 206. In one embodiment, the Hive 206 may save a copy of the data object 1902 as associated with the identification number of the Partner 204. In various embodiments, Hive 206 processes the data 1902 included in the clinical summary. Processing the data 1902 included in the clinical summary may include filtering and normalizing the data 1902. In certain embodiments, Hive 206 forwards the clinical summary and associated data 1902 to the Sponsor 202. Once received by the Sponsor's system 202, the clinical summary and associated data 1902 may be used to update the member records within the Sponsor's system 202.

In various embodiments, the data objects 1902 may be included as thumbnails in messages sent from the Partner 204 to other systems such as the Sponsor 202 for making referrals, requesting risk adjustments, or other related tasks.

As will be understood from the discussions herein, the above steps may occur automatically. For example, if a user creates a clinical summary, the user may select to "print" the summary and, in response, the system may automatically create the files and further transmit the files to the Sponsor 202 via Hive 206.

Exemplary Insights Application Decision Tree

Turning now to FIG. 20, exemplary decision tree logic for surfacing content into the workflow of a third party system is shown, according to various aspects of the present disclosure. In one embodiment, the IA will query Hive every three seconds (or any appropriate time interval) for available healthcare data for a currently authenticated user (Step 2002). In various embodiments, if the API query to Hive returns a patient in context for the user or if the API query to Hive does not return a patient in context for the currently authenticated user (Step 2004), in either case, the IA may check if a current content alert is already present on the display (Step 2006). In the case of a patient currently in context, and if no current alert already exists on screen, then the IA may surface a new content alert into the workflow of the third-party system for the patient in context. However, if a current content alert does already exist on screen, then the IA may make a determination if the current "bubble" (e.g., pop-up notification) is related to the same patient as the patient returned in the Hive API patient context query (Step 2008). In certain embodiments, if the two patients are not in fact the same person (e.g., patient IDs do not match), then the IA may simply close the existing content alert bubble and surface a new content alert for the new patient currently in context as reported by Hive (Steps 2010 and 2012). In particular embodiments, if the two patients are in fact the same person (e.g., patient IDs match), then the IA may take no action and the currently surfaced content alert will remain on screen (Step 2014). According to one aspect of the present disclosure, if the original query to the Hive API returned no patient in context for the currently authenticated user, yet a content alert does currently exist on screen, then the IA may close the content alert and remove it from the screen at step 2016 (e.g. user navigates away from a patient chart and the currently surfaced content may automatically be removed from view as there is no longer correlated patient contexts in view).

Referring back to step 2004, and in one embodiment, if the query to Hive returns patient context and an alert is not currently displayed on the Partner 204 screen (Step 2006), the IA may determine if a "bubble"/alert corresponding to the patient context has been selected before (Step 2030). In various embodiments, if an alert has been selected before, the IA created a timer for the alert, and the IA determines if the timer has expired (Step 2032). In one embodiment, if the timer has expired, the IA surfaces a new content alert at step 2012, and if it has not expired then the process may terminate.

Continuing with FIG. 20, from a user's perspective, if the user dismisses the content alert summary at step 2014 (e.g. clicks the close button on the alert), then the IA 210 may remove the surfaced content alert summary and start an acknowledgement timer that is configurable by location/organization (Steps 2020 and 2028). However, if the user clicks on the content summary alert to view more details, the IA 210 may remove the content alert from screen and open the IA 210 detailed view of the member data, as described previously herein (Steps 2022, 2024, and 2026). In one embodiment, this action of viewing more detail will also acknowledge the content summary alert and will as well start an acknowledgement timer that is configurable by location/organization (Step 2028). In various embodiments, this timer may expire prior to another content alert summary being surfaced again for the same patient.

Exemplary Insights Application Visual Aspects and Functionality

Figure 25:
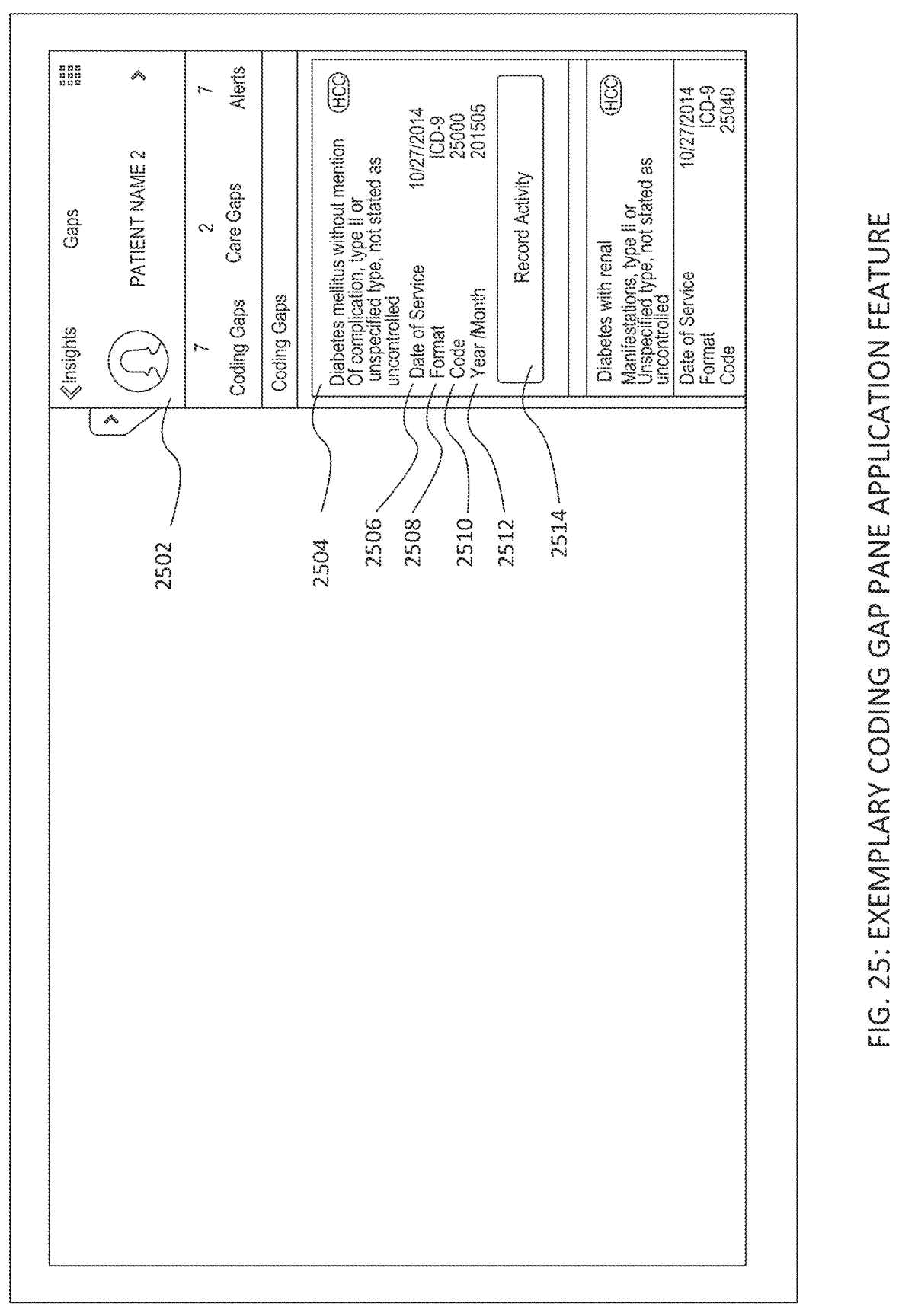
Figure 27:
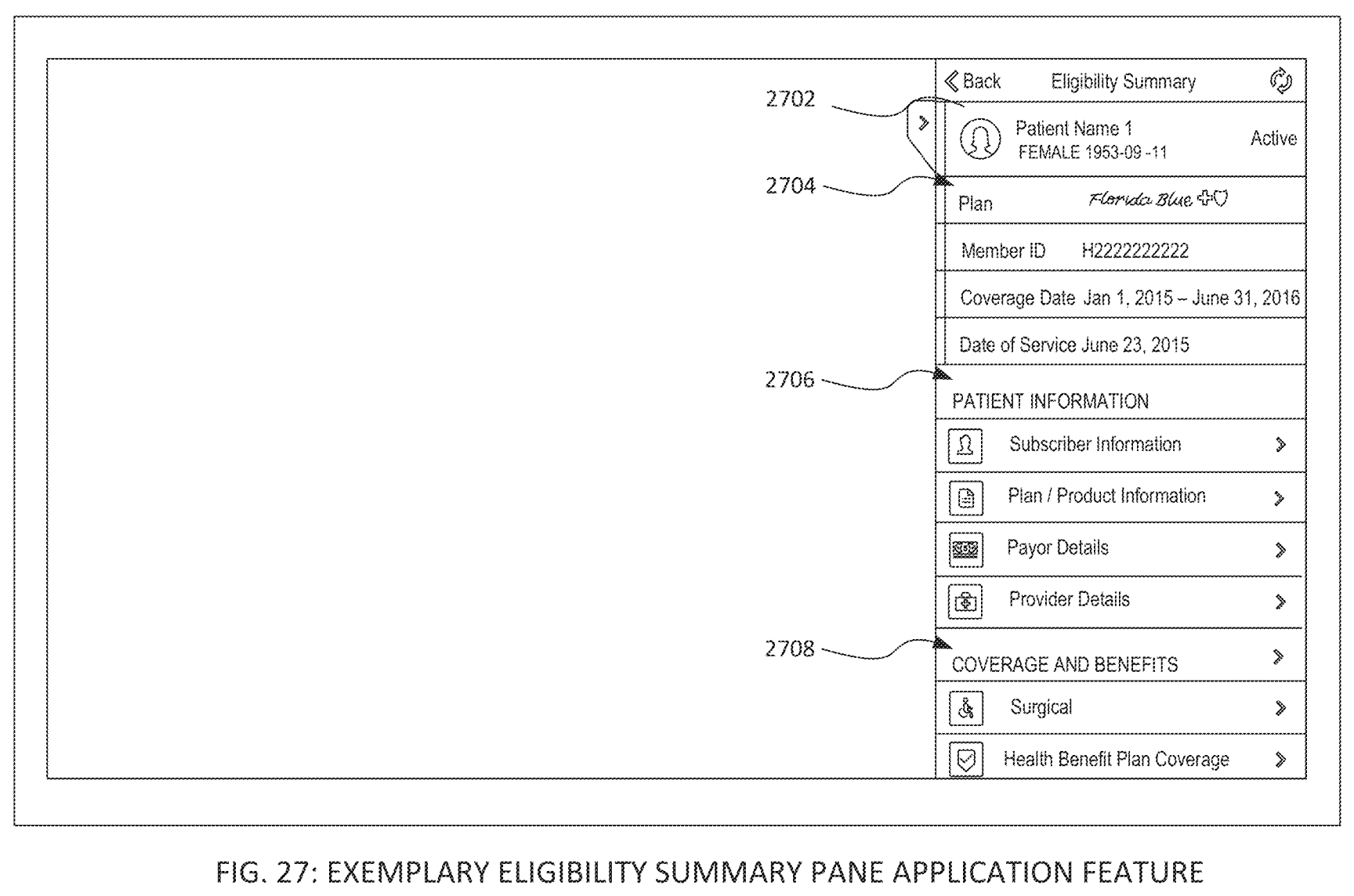

Referring now to FIGS. 21-29, exemplary visual aspects of the Insights Application (IA) are shown, according to one embodiment of the present disclosure. In various embodiments, the IA allows for contextually relevant patient data to be surfaced onto the display of a Partner's computing system. As will be described in the discussion on the following figures, a user may interact with the Insights Application via a touch screen interface, point-and-click display, or any other appropriate interactive display.

Looking now at FIG. 21, a computer display with a tab 2102 is shown, according to one embodiment. In various embodiments, the tab 2102 generally is located at an edge of the display. In the present embodiment, the tab 2102 is located on the right-hand side of the display and represents the ability for a user to touch, click on, or otherwise select the tab 2102 to access additional functionality of the IA. According to various aspects of the present disclosure, the tab 2102 of the IA may be present on the display of a computing device in both an active and inactive state. For example, when the IA is launched, the tab 2102 may be selected to display additional views of the IA. When the IA is inactive, the tab 2102 may be selected to present a sign-in or password screen in order for a user to further launch the IA.

FIG. 22 illustrates the exemplary sign-in view pane 2202 of the IA, according to one embodiment. In the present embodiment, the tab 2102 from FIG. 21 has been selected by the user of the IA and further has exposed a view pane that was previously concealed. In one embodiment, if the user is not signed into the IA upon selecting the tab 2102, the first view pane presented to the user may be the sign-in view pane 2202. In various embodiments, selecting the tab 2102 may result in the sign-in view pane 2202 "sliding" into view on the display (e.g., the pane gradually becomes more exposed as it is revealed from outside the display boundaries). In particular embodiments, the sign-in view pane 2202 may include a sign-in button 2204 or selectable region within the sign-in view pane 2202 to be presented with a separate view pane for entering security credentials. In some embodiments, upon selecting the sign-in button 2204, the sign-in view pane 2202 may not change but instead a graphic or visual may be presented within the sign-in view pane 2202.

Looking now at FIG. 23, in one embodiment, and in response to a user selecting the sign-in button 2204, a password view pane 2302 is presented on the display. In the present disclosure, the password view pane 2302 includes a 12-button keypad 2304 for entering user credentials. According to various aspects of the present disclosure, a user of the IA may use the 12-button keypad to enter a password including a particular number of digits (e.g., the number of digits may vary based on preferred security), the user may enter a password including a combination of keystrokes (e.g., numbers, letters, and symbols), or the user may select and drag on the password view pane to draw a unique pattern that resembles his/her sign-in credential.

Proceeding now to FIG. 24, a pop-up alert 2402 (e.g., a notification or "button") is shown, according to one aspect of the present disclosure. In various embodiments, the IA is operable to receive patient data from Hive in response to electronic health record activity occurring at various third-party systems that are associated with a particular patient or in response to a particular chart being open on the present system (not shown). In one embodiment, and as a result of the electronic health record activity being detected, the pop-up alert 2402 may be displayed on the user's display. In a particular embodiment, the pop-up alert 2402 may be displayed as a result of the user's IA, in the present embodiment, accessing a particular patients electronic health records on a separate display or device or on the present display of the device. As seen in the present embodiment, the pop-up alert 2402 may include patient data such as care gaps 2404, coding gaps 2406, and general alerts 2408. In various embodiments, the pop-up alert 2402 includes number indicators for displaying how many care gaps 2404, coding gaps 2406, and general alerts 2408 have been detected, for example the numbers 2, 7, and 7 representing the previously listed categories, respectively. According to various aspects of the present disclosure, selecting the pop-up alert 2402 may result in the IA 210 presenting a more detailed pane including the health care data corresponding to the indicated gaps. In some embodiments, an alert 2402 relating to a particular patient may be surfaced onto the screen at a Partner if the user at the Partner is viewing an open electronic health record relating to the particular patient, if the user is viewing an electronic health record relating to another patient, or if the user is not currently viewing any particular electronic health record.

Turning now to FIG. 25, a patient code gap pane 2502 is shown, according to one embodiment. In various embodiments, the patient code gap pane 2502 includes health care data missing from, or otherwise inconsistent with, the Partner's EHR system, thereby resulting in a code gap. In the present embodiment, a coding gap 2504 is shown and includes healthcare information related to Diabetes Mellitus. In a particular embodiment, information associated with the coding gap 2504 may include date of service 2506, format 2508, code 2510, and year/month 2512. In some embodiments, the information associated with the coding gap is transmitted to the IA from the Hive, where the information was stored in a context table similar to the table shown in FIG. 13. In one embodiment, the user may decide to ignore the coding gap 2504, or the user may record the coding gap 2504 information by selecting a record activity button 2514. According to various aspects of the present disclosure, selecting the record activity button 2514 may result in the IA updating the EHR system or particular electronic health record to include the data from the coding gap 2504.

Referring now to FIG. 26, an exemplary profile pane 2602 corresponding to a particular patient is shown, according to one embodiment. In one embodiment, the profile pane 2602 corresponding to a particular patient allows for the user at the Partner to navigate particular aspects of the particular patient's health history and recent health-related activity. As shown in the present embodiment, the profile pane 2602 may include general information relating to the patient such as name, date of birth, telephone number, etc., shown at 2604. In addition to the general information shown at 2604, the profile pane 2602 may further include information such as the particular patient's insurance provider (e.g., Payer: BCBSF) and his/her member identification number associated with that insurance provider (e.g., Member ID: H2222222222), as shown at 2606. In various embodiments, the profile pane 2602 includes selectable buttons/regions such as a View Activity Timeline button 2608 and a View Eligibility & Benefits button 2610. According to various aspects of the present disclosure, a user at the Partner may select either of these buttons (2608 and/or 2610) to be presented with additional information relating to the particular patient's activity timeline or insurance eligibility/ benefits, or the user may be presented with an entirely new view pane. In certain embodiments, the user at the Partner 204 organization may determine particular risk factors associated with the particular patient, and the user may indicate them accordingly at the Other Risk Factors menu 2612. In various embodiments, indicating particular risk factors for a particular patient may result in a clinical summary (or other appropriate form of healthcare data) being transmitted to the patient's corresponding Sponsor 202 for a risk adjustment.

Turning now to FIG. 27, an exemplary Eligibility Summary pane 2702 is shown, according to one embodiment. In various embodiments, and mentioned briefly above in the discussion of FIG. 26, in response to selecting the View Eligibility & Benefits button 2610, the user at the Partner 204 organization is presented with a new view pane including detailed insurance information associated with the particular patient. According to various aspects of the present disclosure, the Eligibility Summary pane 2702, in response to selecting the View Eligibility & Benefits button 2610, may visually appear to slide and overlay the profile pane 2602 (or any other previously displayed view pane). In a particular embodiment, the Eligibility Summary pane 2702 includes the insurance and benefit information a user at the Partner 204 organization may need to know in order to provide effective and efficient care.

For example, shown at 2704 is general information relating to the particular patient, such as his/her insurance plan, his/her corresponding member ID, his/her coverage date range, and his/her last date of service. The information at 2704 is generally presented to the user, however, in some embodiments the information may be included in a dropdown menu or otherwise concealed until selected. As shown in the present embodiment, detailed and specific eligibility information relating to the particular patient is included in the Patient Information 2706 and Coverage and Benefits 2708 sections of the Eligibility Summary pane 2702. Looking at the Patient Information 2706 section, the user may view specific details corresponding to the patient's eligibility such as subscriber information, plan/product information, payor details, and provider details. Referring to the Coverage and Benefits 2708 section, the user may view specific details corresponding to surgical coverage, health benefit plan coverage, etc. The information included in the Patient Information 2706 and Coverage and Benefits 2708 sections provide the user with on-demand access to details regarding the particular patient's health care eligibility, but that information may not be necessary to view during every visit.

Turning now to FIG. 28, an exemplary schedule pane 2802 is shown, according to one embodiment. In various embodiments, the schedule pane 2802 corresponds to the Partner's 204 scheduled appointments for a particular day, week, month, etc. In a particular embodiment, the schedule pane 2802 may present the scheduled appointments in chronological order and categorized according to the particular hour of the appointments. For example, the schedule pane 2802 includes appointments for Patient #1, Patient #2, and Patient #3, beginning at 7:00 AM, 7:30 AM, and 7:30 AM, respectively, each organized into a 7:00 AM time slot 2804. Furthermore, in the present embodiment, Patient #4 and Patient #5 have appointments organized into an 11:00 AM time slot 2806, each appointment beginning at 11:30 AM and 11:15 AM, respectively. In particular embodiments, the appointments within each time slot (2804 and 2806) may be presented in other measures of priority, such as length of appointment, if the patient has arrived at the Partner 204 organization, or if there is an error in the particular patient's health records. Turning now to FIG. 29, an exemplary record activity pane 2902 is shown, according to one embodiment. In the present embodiment, a user at the Partner 204 organization may record or report certain health related activity associated with a particular patient to a Sponsor 202, Hive 206, or another appropriate third-party system. According to various aspects of the present disclosure, the user may select a Find in Files 2904 option, an Attach from EHR 2906 option, or any other appropriate method for selecting particular portions (if not all) of electronic health data to record or report. In various embodiments, the record activity pane 2902 may correspond to the "printer capture" process described in the discussion of FIG. 19. For example, the recorded files or EHR data may be transmitted to Hive 206 and further to the Sponsor 202 for reporting risk adjustments, submitting insurance claims, etc.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media that can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data that cause a general-purpose computer, special purpose computer, or special purpose-processing device such as a mobile device processor to perform one specific function or a group of functions.

Those skilled in the art will understand the features and aspects of a suitable computing environment in which aspects of the disclosure may be implemented. Although not required, some of the embodiments of the claimed systems may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represents examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multiprocessor systems, microprocessor-based or programmable consumer electronics, networked PCs, minicomputers, mainframe computers, and the like. Embodiments of the claimed system are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems are embodied. The logical connections between computers include a local area network (LAN), a wide area network (WAN), virtual networks (WAN or LAN), and wireless LANs (WLAN) that are represented here by way of example and not limitation. Such networking environments are commonplace in office-wide or enterprise-wide computer networks, intranets, and the Internet.

When used in a LAN or WLAN networking environment, a computer system implementing aspects of the system is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Additional Aspects

Various aspects of the present systems and methods will now be described. It will be understood by one of ordinary skill in the art that any of the aspects below may incorporate and include any other aspects mentioned below or features described herein. Therefore, the aspects below should be understood to include any combination of aspects and should not be limited to the combinations presented below. For example, although the second aspect includes the computer system of the first aspect, it may also include features of the twenty-sixth aspect, the first aspect, or the hundredth aspect.

According to a first aspect, the present systems and methods, in various embodiments, may include a distributed architecture system for reconciling healthcare information between disparate sources, comprising: A) a surfacing application for presenting health record related alerts on a display in conjunction with electronic health records, the surfacing application operatively connected to at least one computing device at a healthcare clinic including the display; B) at least one patient context sensor operatively connected to a clinic health record database comprising electronic health records associated with a particular set of patients and configured to monitor interactions with the clinic health record database at preconfigured intervals to detect a trigger event, the trigger event corresponding to the at least one computing device electronically accessing one or more of the electronic health records; C) at least one third-party context sensor operatively connected to a remote data repository and configured to poll the remote data repository for third-party analytic data from a sponsor system, the third-party analytic data comprising healthcare information corresponding to at least a subset of the particular set of patients; and D) a cloud-based micro-services system operatively connected to the at least one third-party context sensor and the at least one patient context sensor, the cloud-based micro-services system comprising at least one micro-services database and one or more processors configured for: 1) in response to the at least one third-party context sensor monitoring the remote data repository, receiving the third-party analytic data comprising the healthcare information from the at least one third-party context sensor; 2) associating an identification number with each patient included in the subset of the particular set of patients; 3) in response to the at least one patient context sensor detecting a particular trigger event, receiving accessed chart data from the at least one context sensor, the accessed chart data corresponding to a particular patient's electronic health record; 4) determining healthcare gap information between the received accessed chart data and the healthcare information with a corresponding identification number, wherein the healthcare gap information comprises healthcare data other than the accessed chart data; and 5) transmitting the healthcare gap information to the surfacing application, wherein the healthcare gap information is surfaced onto the display of the at least one computing device in the form of an alert.

According to a second aspect, the distributed architecture system of the first aspect or any other aspect, wherein the particular trigger event comprises the particular accessed electronic health record being accessed by the at least one computing device.

According to a third aspect, the distributed architecture system of the first aspect or any other aspect, wherein the clinic health record database and the cloud-based micro-services system are physically separated.

According to a fourth aspect, the distributed architecture system of the first aspect or any other aspect, wherein the at least one patient context sensor is configured to detect the particular trigger event by interacting with at least one event notification system application programming interface of the at least one computing device.

According to a fifth aspect, the distributed architecture system of the first aspect or any other aspect, wherein the at least one patient context sensor is configured to detect the particular trigger event by accessing data included in the clinic health record database.

According to a sixth aspect, the distributed architecture system of the first aspect or any other aspect, wherein the at least one patient context sensor receives a list of identifiers from the cloud-based micro-services system prior to detecting the particular trigger event.

According to a seventh aspect, the distributed architecture system of the sixth aspect or any other aspect, wherein the list of identifiers is extracted from the third-party analytic data of the sponsor.

According to an eighth aspect, the distributed architecture system of the seventh aspect, or any other aspect, wherein the sponsor is a healthcare insurance provider.

According to a ninth aspect, the distributed architecture system of the first aspect or any other aspect, wherein the at least one micro-services database stores the health records in a normalized canonical format.

According to a tenth aspect, the distributed architecture system of the first aspect or any other aspect, wherein the at least one micro-services database is a NoSQL Key-Value database.

According to an eleventh aspect, the distributed architecture system of the first aspect or any other aspect, wherein prior to transmitting the healthcare gap information to the at least one computing device, the healthcare gap information is stored in a context table at the cloud-based micro-services system, wherein the context table is accessible by one or more additional computing devices at healthcare clinics associated with the particular patient.

According to a twelfth aspect, the distributed architecture system of the first aspect or any other aspect, wherein the healthcare gap information is transmitted to the at least one computing device via a micro-services application programming interface.

According to a thirteenth aspect, the present systems and methods may include, in various embodiments, a method for reconciling healthcare information between disparate sources in a distributed architecture system, the method comprising the steps of: A) monitoring a clinic health record database at preconfigured intervals via at least one patient context sensor to detect a trigger event corresponding to at least one computing device electronically accessing one or more of the electronic health records stored at the clinic health record database, the at least one patient context sensor operatively connected to the clinic health record database; B) polling a remote data repository via at least one third-party context sensor operatively connected to the remote data repository for third-party analytic data from a sponsor system, the third-party analytic data comprising healthcare information corresponding to at least a subset of a particular set of patients; and C) in response to the at least one third-party context sensor polling the remote data repository, receiving at a cloud-based micro-services system the third-party analytic data comprising the healthcare information from the third-party context sensor, the cloud-based micro-services system operatively connected to the at least one third-party context sensor and the at least one patient context sensor, the cloud-based micro-services system comprising at least one micro-services database and one or more processors configured for: 1) associating an identification number with each patient included in the subset of the particular set of patients; 2) in response to the at least one patient context sensor detecting a particular trigger event, receiving accessed chart data from the at least one context sensor, the accessed chart data corresponding to a particular patient's electronic health record; 3) determining healthcare gap information between the received accessed chart data and the healthcare information with a corresponding identification number, wherein the healthcare gap information comprises healthcare data other than the accessed chart data; and 4) transmitting the healthcare gap information to a surfacing application installed on the at least one computing device, wherein the healthcare gap information is surfaced onto the display of the at least one computing device in the form of an alert.

According to a fourteenth aspect, the method of the thirteenth aspect or any other aspect, wherein the particular trigger event comprises the particular accessed electronic health record being accessed by the at least one computing device.

According to a fifteenth aspect, the method of the thirteenth aspect or any other aspect, wherein the clinic health record database and the cloud-based micro-services system are physically separated.

According to a sixteenth aspect, the method of the thirteenth aspect or any other aspect, wherein the at least one patient context sensor is configured to detect the particular trigger event by interacting with at least one event notification system application programming interface of the at least one computing device.

According to a seventeenth aspect, the method of the thirteenth aspect or any other aspect, wherein the at least one patient context sensor is configured to detect the particular trigger event by accessing data included in the clinic health record database.

According to an eighteenth aspect, the method of the thirteenth aspect or any other aspect, wherein the at least one patient context sensor receives a list of identifiers from the cloud-based micro-services system prior to detecting the particular trigger event.

According to a nineteenth aspect, the method of the eighteenth aspect or any other aspect, wherein the list of identifiers is extracted from the third-party analytic data of the sponsor.

According to a twentieth aspect, the method of the nineteenth aspect or any other aspect, wherein the sponsor is a healthcare insurance provider.

According to a twenty-first aspect, the method of the thirteenth aspect or any other aspect, wherein the at least one micro-services database stores the health records in a normalized canonical format.

According to a twenty-second aspect, the method of the thirteenth aspect or any other aspect, wherein the at least one micro-services database is a NoSQL Key-Value database.

According to a twenty-third aspect, the method of the thirteenth aspect or any other aspect, wherein prior to transmitting the healthcare gap information to the at least one computing device, the healthcare gap information is stored in a context table at the cloud-based micro-services system, wherein the context table is accessible by one or more additional computing devices at healthcare clinics associated with the particular patient.

According to a twenty-fourth aspect, the method the thirteenth aspect or any other aspect, wherein the healthcare gap information is transmitted to the at least one computing device via a micro-services application programming interface.

According to a twenty-fifth aspect, the present systems and methods may include, in various embodiments, a distributed architecture system for detecting healthcare gap information across disparate sources, comprising at least one sensor operatively connected to a clinic health record system database and a cloud-based micro-services system, the at least one sensor comprising one or more application programming interfaces protected by a firewall, the at least one sensor configured to: A) receive, from the cloud-based micro-services system, identification information for a list of patients associated with the at least one third-party system; B) store at least a portion of the identification information at the at least one sensor; C) monitor the clinic health record system database to detect a trigger event, the trigger event corresponding to a computing system electronically accessing a particular electronic health record at the clinic health record system database of at least one of the patients included in the list of patients stored at the at least one sensor; and D) in response to detecting the trigger event, transmit accessed chart data to the cloud-based micro-services system, whereby the cloud-based micro-services system transmits context data relating to particular healthcare gap information to a surfacing application to be surfaced onto a display.

According to a twenty-sixth aspect, the distributed architecture system of the twenty-fifth aspect or any other aspect, wherein the at least one third-party system is an insurance provider.

According to a twenty-seventh aspect, the distributed architecture system of the twenty-fifth aspect or any other aspect, wherein the at least one third-party system is a healthcare providing organization.

According to a twenty-eighth aspect, the distributed architecture system of the twenty-fifth aspect or any other aspect, wherein the accessed chart data comprises a clinic health record system database identifier and particular electronic health record data.

According to a twenty-ninth aspect, the distributed architecture system of the twenty-fifth aspect or any other aspect, wherein the trigger event comprises one or more events selected from the group comprising opening the particular electronic health record, initiating a prescription order, creating a new electronic health record chart, and digitally signing an encounter note.

According to a thirtieth aspect, the distributed architecture system of the twenty-fifth aspect or any other aspect, wherein prior to receiving the identification information for the list of patients, the at least one sensor is configured to transmit a request to the cloud-based micro-services system for the identification information according to predetermined time intervals.

According to a thirty-first aspect, the distributed architecture system of the twenty-fifth aspect or any other aspect, wherein the healthcare gap information is surfaced onto the display by presenting the healthcare gap information in the form of an alert notification.

According to a thirty-second aspect, the distributed architecture system of the thirty-first aspect or any other aspect, wherein the alert notification is presented by sliding the alert notification from outside the display boundaries.

According to a thirty-third aspect, the distributed architecture system of the twenty-fifth aspect or any other aspect, wherein the at least one micro-services database stores the healthcare data in a normalized canonical format.

According to a thirty-fourth aspect, the distributed architecture system of the twenty-fifth aspect or any other aspect, wherein the at least one micro-services database is a NoSQL Key-Value database.

According to a thirty-fifth aspect, the distributed architecture system of the twenty-fifth aspect or any other aspect, wherein the trigger event comprises intercepting an application programming interface call for the particular electronic health record, detecting manipulation of the particular electronic health record at the clinic health record system database, or detecting the particular electronic health record being presented on the display.

According to a thirty-sixth aspect, the distributed architecture system of the thirty-fifth aspect or any other aspect, wherein the particular electronic health record being presented on the display is detected via screen scraping.

According to a thirty-seventh aspect, the present systems and methods may include, in various embodiments, trigger-based method for detecting healthcare gap information across disparate sources, comprising the steps of: A) receiving via at least one sensor operatively connected to a clinic health record system database, from a cloud-based micro-services system, identification information for a list of patients associated with at least one third-party system, wherein the at least one sensor comprises one or more application programming interfaces protected by a firewall; B) storing at least a portion of the identification information at the at least one sensor; C) monitoring the clinic health record system database to detect a trigger event, the trigger event corresponding to a computing system electronically accessing a particular electronic health record at the clinic health record system database of at least one of the patients included in the list of patients stored at the at least one sensor; and D) in response to detecting the trigger event, transmitting accessed chart data to the cloud-based micro-services system, whereby the cloud-based micro-services system transmits to the at least one computing system context data relating to particular healthcare gap information to be surfaced onto the display.

According to a thirty-eighth aspect, the method of the thirty-seventh aspect or any other aspect, wherein the at least one third-party system is an insurance provider.

According to a thirty-ninth aspect, the method of the thirty-seventh aspect or any other aspect, wherein the at least one third-party system is a healthcare providing organization.

According to a fortieth aspect, the method of the thirty-seventh aspect or any other aspect, wherein the accessed chart data comprises a clinic health record system database identifier and particular electronic health record data.

According to a forty-first aspect, the method of the thirty-seventh aspect or any other aspect, wherein the trigger event comprises one or more events selected from the group comprising opening the particular electronic health record, initiating a prescription order, creating a new electronic health record chart, and digitally signing an encounter note.

According to a forty-second aspect, the method of the thirty-seventh aspect or any other aspect, wherein prior to receiving the identification information for the list of patients, the at least one sensor is configured to transmit a request to the cloud-based micro-services system for the identification information according to predetermined time intervals.

According to a forty-third aspect, the method of the thirty-seventh aspect or any other aspect, wherein the healthcare gap information is surfaced onto the display by presenting the healthcare gap information in the form of an alert notification.

According to a forty-fourth aspect, the method of the forty-third aspect or any other aspect, wherein the alert notification is presented by sliding the alert notification from outside the display boundaries.

According to a forty-fifth aspect, the method of the thirty-seventh aspect or any other aspect, wherein the at least one micro-services database stores the healthcare data in a normalized canonical format.

According to a forty-sixth aspect, the method of the thirty-seventh aspect or any other aspect, wherein the at least one micro-services database is a NoSQL Key-Value database.

According to a forty-seventh aspect, the method of the thirty-seventh aspect or any other aspect, wherein the trigger event comprises intercepting an application programming interface call for the particular electronic health record, detecting manipulation of the particular electronic health record at the clinic health record system database, or detecting the particular electronic health record being presented on the display.

According to a forty-eighth aspect, the method of the forty-seventh aspect or any other aspect, wherein the particular electronic health record being presented on the display is detected via screen scraping.

According to a forty-ninth aspect, the present systems and methods may include, in various embodiments, a distributed architecture system for tracking patient information across a plurality of disparate third-party computing systems, comprising: A) one or more sensors connected to the plurality of disparate third-party computing systems, each of the one or more sensors comprising on or more application programming interfaces protected by a firewall for electronically communicating the patient information between the plurality of disparate third-party computing systems; and B) a cloud-based micro-services system in operative communication with the one or more sensors, the cloud-based micro-services system comprising one or more processors configured to: 1) receive a request from a first sensor associated with a first third-party computing system to receive electronic health record information corresponding to a particular patient identifier associated with a particular patient, the first third-party computing system associated with a particular system identifier; 2) match the particular patient identifier with corresponding electronic health record information and corresponding member information; 3) store the particular patient identifier and corresponding member information associated with the electronic health record information; and 4) upon receiving additional healthcare information from a second sensor associated with a second third-party computing system associated with a second particular system identifier, transmit to the first third-party computing system at least a portion of the matched electronic health record information and member information.

According to a fiftieth aspect, the system of the forty-ninth aspect or any other aspect, wherein at least one of the plurality of disparate third-party computing systems is an insurance provider.

According to a fifty-first aspect, the system of the forty-ninth aspect or any other aspect, wherein the electronic health record information is normalized in a canonical format.

According to a fifty-second aspect, the system of the forty-ninth aspect or any other aspect, wherein the additional healthcare information comprises healthcare gap information.

According to a fifty-third aspect, the system of the forty-ninth aspect or any other aspect, wherein the one or more processors operate in approximately real-time.

According to a fifty-fourth aspect, the system of the forty-ninth aspect or any other aspect, wherein the at least a portion of the matched electronic health record information and member information is transmitted to a surfacing application at the first third-party computing system to be presented as an alert on a display.

According to a fifty-fifth aspect, the system of the forty-ninth aspect or any other aspect, wherein the particular patient identifier comprises Medicaid identification numbers.

According to a fifty-sixth aspect, the system of the forty-ninth aspect or any other aspect, wherein the one or more third-party computing-system identifier comprise National Provider Identifier (NPIs).

According to a fifty-seventh aspect, the present systems and methods may include, in various embodiments, a computer-implemented method for tracking patient information across a plurality of disparate third-party computing systems via a distributed architecture, comprising the steps of: A) receiving, at a cloud-based micro-services system in operative communication with one or more sensors connected to the plurality of disparate third-party computing systems, a request from a first sensor associated with a first third-party computing system to receive electronic health record information corresponding to a particular patient identifier associated with a particular patient, the first third-party computing system associated with a particular system identifier; B) matching the particular patient identifier with corresponding electronic health record information and corresponding member information; C) storing the particular patient identifier and corresponding member information associated with the electronic health record information; and D) upon receiving additional healthcare information from a second sensor associated with a second third-party computing system associated with a second particular system identifier, transmitting to the first third-party computing system at least a portion of the matched electronic health record information and member information.

According to a fifty-eighth aspect, the computer-implemented method of the fifty-seventh aspect or any other aspect, wherein at least one of the plurality of disparate third-party computing systems is an insurance provider.

According to a fifty-ninth aspect, the computer-implemented method of the fifty-seventh aspect or any other aspect, wherein the electronic health record information is normalized in a canonical format.

According to a sixtieth aspect, the computer-implemented method of the fifty-seventh aspect or any other aspect, wherein the additional healthcare information comprises healthcare gap information.

According to a sixty-first aspect, the computer-implemented method of the fifty-seventh aspect or any other aspect, wherein the one or more processors operate in approximately real-time.

According to a sixty-second aspect, the computer-implemented method of the fifty-seventh aspect or any other aspect, wherein the at least a portion of the matched electronic health record information and member information is transmitted to a surfacing application at the first third-party computing system to be presented as an alert on a display.

According to a sixty-third aspect, the computer-implemented method of the fifty-seventh aspect or any other aspect, wherein the particular patient identifier comprises Medicaid identification numbers.

According to a sixty-fourth aspect, the computer-implemented method of the fifty-seventh aspect or any other aspect, wherein the one or more third-party computing-system identifier comprise National Provider Identifier (NPIs).

According to a sixty-fifth aspect, the present systems and methods include a distributed architecture system for detecting healthcare gap information across disparate sources, comprising a cloud-based micro-services system operatively connected to at least one sensor and a surfacing application and comprising at least one micro-services database including electronic health records received from at least one third-party system and at least one processor configured to: A) receive from the at least one sensor, particular accessed electronic health record data associated with a particular accessed electronic health record and an identifier associated with a clinic health record system database in response to the at least one sensor detecting a particular trigger event; B) in response to receiving the particular accessed electronic health record data and the identifier, retrieve one or more electronic health records matching at least portions of the particular accessed electronic health record data from the at least one micro-services database based at least in part on the identifier; C) compare the particular accessed electronic health record data to the one or more electronic health records and store healthcare gap information in a context table accessible by the surfacing application via a micro-services application programming interface, wherein the healthcare gap information comprises information other than the information included in the particular accessed electronic health record data; D) receive, from the surfacing application at predetermined intervals, queries for the healthcare gap information; and E) automatically transmit the healthcare gap information to the surfacing application, wherein the surfacing application modifies a display of at least one computing system by surfacing the healthcare gap information, wherein surfacing the healthcare gap information comprises: i) surfacing an alert, the alert selectable by a user at the surfacing application and comprising a partial record of the healthcare gap information; and ii) in response to the user selecting the alert, surfacing a complete record of the healthcare gap information, wherein the complete record of the healthcare gap information replaces the alert on the display.

According to a sixty-sixth aspect, the system of the sixty-fifth aspect or any other aspect, wherein the particular trigger event comprises the particular accessed electronic health record being accessed by the at least one computing system.

According to a sixty-seventh aspect, the system of the sixty-fifth aspect or any other aspect, wherein the clinic health record system database and the cloud-based micro-services system are physically separated.

According to a sixty-eight aspect, the system of the sixty-fifth aspect or any other aspect, wherein the at least one sensor is configured to detect the particular trigger event by interacting with at least one event notification system application programming interface of the at least one computing system.

According to a sixty-ninth aspect, the system of the sixty-fifth aspect or any other aspect, wherein the at least one sensor is configured to detect the particular trigger event by at least one of the group comprising accessing data included in the clinic health record system database, intercepting an application programming interface call for the particular electronic health record, and screen scraping the electronic health record data from the display.

According to a seventieth aspect, the system of the sixty-fifth aspect or any other aspect, wherein the at least one sensor receives a list of identifiers from the cloud-based micro-services system prior to detecting the particular trigger event.

According to a seventy-first aspect, the system of the seventieth aspect or any other aspect, wherein the identifier associated with the clinic health record system database is included in the list of identifiers.

According to a seventy-second aspect, the system of the seventy-first aspect or any other aspect, wherein the cloud-based micro-services system initially receives the list of identifiers from a sponsor organization's analytics system.

According to a seventy-third aspect, the system of the sixty-fifth aspect or any other aspect, wherein the at least one micro-services database stores the health records in a normalized canonical format.

According to a seventy-fourth aspect, the system of the sixty-fifth aspect or any other aspect, wherein the at least one micro-services database is a NoSQL Key-Value database.

According to a seventy-fifth aspect, computer-implemented method for surfacing healthcare gap information detected between disparate sources via a distributed computer architecture system, the computer-implemented method comprising the steps of: A) receiving, at a cloud-based micro-services system, from at least one sensor operatively connected to a clinic health record system database and in response to the at least one sensor detecting a particular trigger event associated with a particular accessed electronic health record, particular accessed electronic health record data associated with the particular accessed electronic health record and an identifier associated with the clinic health record system database, wherein the at least one sensor is configured to poll the clinic health record system database at preconfigured intervals to detect the particular trigger event and the particular trigger event comprises electronic access to the particular accessed electronic health record; B) in response to receiving the particular accessed electronic health record data and the identifier, retrieving, via the cloud-based micro-services system, one or more electronic health records matching at least portions of the particular accessed electronic health record data from at least one micro-services database operatively connected to the cloud-based micro-services system based at least in part on the identifier; C) comparing, via the cloud-based micro-services system, the particular accessed electronic health record data to the one or more electronic health records to identify healthcare gap information and storing the healthcare gap information in a context table accessible by a surfacing application operatively connected to the cloud-based micro-services system via a micro-services application programming interface, wherein the healthcare gap information comprises information other than the information included in the particular accessed electronic health record data; D) receiving, from the surfacing application at predetermined intervals, queries from the surfacing application for the healthcare gap information; and E) automatically transmitting the healthcare gap information to the surfacing application, wherein the surfacing application modifies a display of at least one computing system by surfacing the healthcare gap information, wherein surfacing the healthcare gap information comprises: i) surfacing an alert, the alert selectable by a user at the surfacing application and comprising a partial record of the healthcare gap information; and ii) in response to the user selecting the alert, surfacing a complete record of the healthcare gap information, wherein the complete record of the healthcare gap information replaces the alert on the display.

According to a seventy-sixth aspect, the computer-implemented method of the seventy-fifth aspect or any other aspect, wherein the particular trigger event comprises the particular accessed electronic health record being opened on the display.

According to a seventy-seventh aspect, the computer-implemented method of the seventy-fifth aspect or any other aspect, wherein the clinic health record system database and the cloud-based micro-services system are physically separated.

According to a seventy-eight aspect, the computer-implemented method of the seventy-fifth aspect or any other aspect, wherein the at least one sensor is configured to detect the particular trigger event by interacting with at least one event notification system application programming interface of the at least one computing system.

According to a seventy-ninth aspect, the computer-implemented method of the seventy-fifth aspect or any other aspect, wherein the at least one sensor is configured to detect the particular trigger event by at least one of the group comprising accessing data included in the clinic health record system database, intercepting an application programming interface call for the particular electronic health record, and screen scraping the electronic health record data from the display.

According to an eighth aspect, the computer-implemented method of the seventy-fifth aspect or any other aspect, wherein the at least one sensor receives a list of identifiers from the cloud-based micro-services system prior to detecting the particular trigger event.

According to an eighty-first aspect, the computer-implemented method of the eightieth aspect or any other aspect, wherein the particular accessed electronic health record is associated with an identifier included in the list of identifiers.

According to an eighty-second aspect, the computer-implemented method of the eighty-first aspect or any other aspect, wherein the cloud-based micro-services system initially receives the list of identifiers from a sponsor organization's analytics system.

According to an eighty-third aspect, the computer-implemented method of the seventy-fifth aspect or any other aspect, wherein the at least one micro-services database stores the one or more electronic health records in a normalized canonical format.

According to an eighty-fourth aspect, the computer-implemented method of the seventy-fifth aspect or any other aspect, wherein the at least one micro-services database is a NoSQL Key-Value database.

According to an eighty-fifth aspect, a system for automatically executing workflows in a distributed architecture, comprising: A) at least one sensor operatively connected to a clinic health record system database, the at least one sensor configured to monitor the clinic health record system database at preconfigured intervals to detect a trigger event, the trigger event corresponding to electronic access to an electronic health record; and B) a cloud-based micro-services system operatively connected to the at least one sensor and comprising at least one micro-services database including electronic health records received from at least one third-party system, and a set of predetermined instructions for responding to the trigger event, wherein: i) the cloud-based micro-services system receives a request from the at least one sensor requesting the set of predetermined instructions for responding to the trigger event; ii) the cloud-based micro-services system transmits the set of predetermined instructions to the sensor; and iii) the cloud-based micro-services system receives, in response to the at least one sensor detecting a particular trigger event associated with a particular accessed electronic health record, particular accessed electronic health record data and an identifier associated with the clinic health record system database from the at least one sensor for executing the set of predetermined instructions to automate a workflow.

According to an eighty-sixth aspect, the system of the eighty-fifth aspect or any other aspect, wherein the set of predetermined instructions comprise instructions for transmitting at least a portion of the particular accessed electronic health record data to a sponsor organization.

According to an eighty-seventh aspect, the system of the eighty-fifth aspect or any other aspect, wherein the clinic health record system database and the cloud-based micro-services system are physically separated.

According to an eighty-eighth aspect, the system of the eighty-fifth aspect or any other aspect, wherein the set of predetermined instructions are initially configured by a user at the at least one computing system.

According to an eighty-ninth aspect, the system of the eighty-fifth aspect or any other aspect, wherein the workflow comprises transmitting a medical prescription to a pharmacy.

According to a ninetieth aspect, the system of the eighty-fifth aspect or any other aspect, wherein the workflow comprises transmitting, to a sponsor organization, a form populated with at least a portion of the particular accessed electronic health record data based on the predetermined instructions for automatically documenting a claim with the sponsor organization According to a ninety-first aspect, the system of the ninetieth aspect or any other aspect, wherein automatically documenting a claim comprises completing a risk adjustment form.

According to a ninety-second aspect, the system of the ninetieth aspect or any other aspect, wherein automatically documenting a claim comprises completing an insurance claim.

According to a ninety-third aspect, a computer-implemented method for automating tasks in a workflow, comprising the steps of: A) in response to at least one sensor monitoring a clinic health record system database at preconfigured intervals for detecting a trigger even corresponding to electronic access to an electronic health record, receiving a request from the at least one sensor at a cloud-based micro-services system, the cloud-based micro-services system operatively connected to the at least one sensor and comprising at least one micro-services database including electronic health records received from at least one third-party system, and a set of predetermined instructions for responding to the trigger event, the request requesting the set of predetermined instructions for responding to the trigger event; B) transmitting the set of predetermined instructions to the at least one sensor; and C) receiving, in response to the at least one sensor detecting a particular trigger event associated with a particular accessed electronic health record, particular accessed electronic health record data and an identifier associated with the clinic health record system database from the at least one sensor for executing the set of predetermined instructions to automate a workflow.

According to a ninety-fourth aspect, the computer-implemented method of the ninety-third aspect or any other aspect, wherein the set of predetermined instructions comprise instructions for transmitting at least a portion of the particular accessed electronic health record data to a sponsor organization.

According to a ninety-fifth aspect, the computer-implemented method of the ninety-third aspect or any other aspect, wherein the clinic health record system database and the cloud-based micro-services system are physically separated.

According to a ninety-sixth aspect, the computer-implemented method of the ninety-third aspect or any other aspect, wherein the set of predetermined instructions are initially configured by a user at the at least one computing system.

According to a ninety-seventh aspect, the computer-implemented method of the ninety-third aspect or any other aspect, wherein the workflow comprises transmitting a medical prescription to a pharmacy.

According to a ninety-eight aspect, the computer-implemented method of the ninety-third aspect or any other aspect, wherein the workflow comprises transmitting, to a sponsor organization, a form populated with at least a portion of the particular accessed electronic health record data based on the predetermined instructions for automatically documenting a claim with the sponsor organization According to a ninety-ninth aspect, the computer-implemented method of the ninety-eighth aspect or any other aspect, wherein automatically documenting a claim comprises completing a risk adjustment form.

According to a hundredth aspect, the computer-implemented method of the ninety-eighth aspect or any other aspect, wherein automatically documenting a claim comprises completing an insurance claim.

CONCLUSION

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

What is claimed is:

1. A system for reconciling healthcare information between disparate sources, comprising:
 a surfacing application for presenting health record related alerts on a display in conjunction with electronic health records, the surfacing application operatively connected to at least one computing system at a healthcare clinic including the display;
 at least one software-defined patient context sensor operatively connected to a health record database, wherein the at least one software-defined patient context sensor is a software configuration operatively configured to monitor interactions with the health record database to detect a data access trigger event indicative of accessed patient data, the accessed patient data accessed at the healthcare clinic and rendered on the display;
 at least one software-defined third-party context sensor, wherein the at least one software-defined third-party context sensor is a software configuration operatively connected to a remote data repository and configured to receive third-party analytic data from a sponsor system, the third-party analytic data comprising healthcare information corresponding to a particular set of patients; and
 a remote micro-services system operatively connected to the at least one software-defined third-party context sensor and the at least one software-defined patient context sensor, the remote micro-services system comprising at least one micro-services database configured to store the healthcare information in a first particular format, and one or more processors configured to:
  receive the third-party analytic data comprising the healthcare information in the first particular format from the at least one software-defined third-party context sensor;
  associate an identification number with each patient included in the particular set of patients;
  in response to the at least one software-defined patient context sensor detecting a particular data access trigger event corresponding to the at least one computing system electronically accessing at least one patient's electronic health record stored at the health record database, receive patient data from the at least one software-defined patient context sensor, wherein the received patient data is received in a second particular format and corresponds to the at least one patient's electronic health record;
  transform the healthcare information received in the first particular format into the second particular format;
  identify healthcare gap information between the received patient data and the healthcare information with a corresponding identification number; and
  transmit the healthcare gap information to the surfacing application, wherein the surfacing application modifies the display of the at least one computing system by surfacing the healthcare gap information.

2. The system of claim 1, wherein:
 the accessed patient data is received by the healthcare clinic from the health record database; and
 the health record database is physically separate from the healthcare clinic.

3. The system of claim 1, wherein:
the accessed patient data is received by the healthcare clinic from the health record database; and
the health record database is local to the healthcare clinic.

4. The system of claim 1, wherein the received patient data is derived from screen scraping the display while the accessed patient data is rendered on the display.

5. The system of claim 4, wherein the received patient data comprises a name and a date of birth corresponding to the accessed patient data rendered on the display.

6. The system of claim 1, wherein the at least one software-defined patient context sensor is configured to monitor the accessed patient data by interacting with at least one event notification system application programming interface of the at least one computing system.

7. The system of claim 1, wherein the accessed patient data comprises a name and date of birth corresponding to the at least one patient's electronic health record.

8. The system of claim 1, wherein the received patient data is derived from screen scraping a separate display in conjunction with the electronic health records, wherein the separate display is operatively connected to a computing system at a separate healthcare clinic.

9. The system of claim 1, wherein the received patient data is derived from screen scraping a separate display in conjunction with the electronic health records, wherein the separate display is operatively connected to a particular computing system of the at least one computing system at the healthcare clinic.

10. A method for reconciling healthcare information between disparate sources via one or more processors configured to execute instructions encoded onto one or more non-transitory computer-readable mediums, wherein the one or more processors executing the instructions encoded onto the one or more non-transitory computer-readable mediums causes the one or more processors to perform the steps of:
monitoring, via at least one software-defined patient context sensor at a computing system and operatively connected to a health record database, interactions with the health record database to detect a data access trigger event indicative of accessed patient data, wherein the software-defined patient context sensor is a software configuration, and wherein the accessed patient data is accessed at a healthcare clinic and rendered on a display associated with the computing system;
receiving, via at least one software-defined third-party context sensor, third-party analytic data from a sponsor system, wherein the at least one software-defined third-party context sensor is a software configuration, and wherein the third-party analytic data comprises healthcare information corresponding to a particular set of patients;
receiving, at a remote micro-services system, the third-party analytic data comprising the healthcare information in a first particular format from the at least one software-defined third-party context sensor, wherein the remote micro-services system is operatively connected to the at least one software-defined third-party context sensor and the at least one software-defined patient context sensor;
associating, at the remote micro-services system, an identification number with each patient included in the particular set of patients;
in response to the at least one software-defined patient context sensor detecting a particular data access trigger event corresponding to the at least one computing system electronically accessing at least one patient's electronic health record stored at the health record database, receiving, at the remote micro-services system, patient data from the at least one software-defined patient context sensor, wherein the received patient data is received in a second particular format and corresponds to at least one patient's electronic health record;
transforming the healthcare information received in the first particular format into the second particular format;
identifying healthcare gap information between the received patient data and the healthcare information with a corresponding identification number; and
transmitting the healthcare gap information to a surfacing application installed on the computing system, wherein the surfacing application modifies the display of the computing system by surfacing the healthcare gap information.

11. The method of claim 10, wherein:
the accessed patient data is received by the healthcare clinic from the health record database; and
the health record database is physically separate from the healthcare clinic.

12. The method of claim 10, wherein:
the accessed patient data is received by the healthcare clinic from the health record database; and
the health record database is local to the healthcare clinic.

13. The method of claim 10, wherein the received patient data is derived from screen scraping the display while the accessed patient data is rendered on the display.

14. The method of claim 13, wherein the received patient data comprises a name and a date of birth corresponding to the accessed patient data rendered on the display.

15. The method of claim 10, wherein the at least one software-defined patient context sensor is configured to monitor the accessed patient data by interacting with at least one event notification system application programming interface of the computing system.

16. The method of claim 10, wherein the accessed patient data comprises a name and date of birth corresponding to the at least one patient's electronic health record.

17. The method of claim 10, wherein the received patient data is derived from screen scraping a separate display in conjunction with the electronic health records, wherein the separate display is operatively connected to at least one computing system at a separate healthcare clinic.

18. The method of claim 10, wherein the received patient data is derived from screen scraping a separate display in conjunction with the electronic health records, wherein the separate display is operatively connected to a particular computing system of the at least one computing system at the healthcare clinic.

* * * * *